United States Patent
Smith

(10) Patent No.: US 11,311,560 B2
(45) Date of Patent: Apr. 26, 2022

(54) CYCLIC PLASMENYLETHANOLAMINES

(71) Applicant: MED-LIFE DISCOVERIES LP, Saskatoon (CA)

(72) Inventor: Tara Smith, Saskatoon (CA)

(73) Assignee: Med-Life Discoveries LP, Saskatoon (CA)

( * ) Notice: Subject to any disclaimer, the term of this patent is extended or adjusted under 35 U.S.C. 154(b) by 12 days.

(21) Appl. No.: 16/605,757

(22) PCT Filed: Mar. 12, 2018

(86) PCT No.: PCT/CA2018/050291
§ 371 (c)(1),
(2) Date: Oct. 16, 2019

(87) PCT Pub. No.: WO2018/191812
PCT Pub. Date: Oct. 25, 2018

(65) Prior Publication Data
US 2021/0128590 A1    May 6, 2021

Related U.S. Application Data

(60) Provisional application No. 62/486,037, filed on Apr. 17, 2017.

(51) Int. Cl.
A61K 31/675    (2006.01)

(52) U.S. Cl.
CPC .................................. A61K 31/675 (2013.01)

(58) Field of Classification Search
None
See application file for complete search history.

(56) References Cited

FOREIGN PATENT DOCUMENTS

| CN | 105646587 A | 6/2016 |
|---|---|---|
| WO | 2013071412 | 5/2012 |
| WO | WO-2013/071412 A1 | 5/2013 |
| WO | WO-2013/071418 A1 | 5/2013 |

OTHER PUBLICATIONS

Le Roux et al., "Decomposition of N-Phosphorylated Nitrogen Mustards: A Mechanistic Investigation," J. Org. Chem, vol. 60(12):3832-3839, Jun. 1995.
Extended European Search Report issued on corresponding European Patent Application No. 18786953.2, dated Nov. 20, 2020.
International Preliminary Report on Patentability issued on International Patent Application No. PCT/CA2018/050291, dated Oct. 31, 2019.
Braverman et al., Mutation analysis of PEX7 in 60 probands with rhizomelic chondrodysplasia punctate and functional correlations of genotype with phenotype, Human Mutat., vol. 20(4):284-297, Oct. 2002.
Itzkovitz et al., Functional characterization of novel mutations in GNPAT and AGPS, causing rhizomelic chondrodysplasia punctate (RCDP) types 2 and 3, Human Mutat., vol. 33(1):189-97, Jan. 2012.
International Search Report, dated Jun. 11, 2018, issued on International Patent Application No. PCT/CA2018/050291.
Jun. 11, 2018, WO, PCT/CA2018/050291.
Braverman, Human Mutat., Mutation analysis of PEX7 in 60 probands with rhizomelic chondrodysplasia punctate and functional correlations of genotype with phenotype, vol. 20(4):284-297, Oct. 2002.
Fallatah W, Smith T, Cui W, et al. Oral administration of a synthetic vinyl-ether plasmalogen normalizes open field activity in a mouse model of Rhizomelic chondrodysplasia punctata. *Disease models & mechanisms*. Jan. 2020.
Han X, Holtzman DM, McKeel DW, Jr. Plasmalogen deficiency in early Alzheimer's disease subjects and in animal models: molecular characterization using electrospray ionization mass spectrometry. *Journal of neurochemistry*. Dec. 2001 ;77(4):1168-1180.
Guan Z, Wang Y, Cairns NJ, Lantos PL, Dallner G, Sindelar PJ. Decrease and structural modifications of phosphatidylethanolamine plasmalogen in the brain with Alzheimer disease. *Journal of neuropathology and experimental neurology*. Jul. 1999;58(7):740-747.
Goodenowe DB, Cook LL, Liu J, et al. Peripheral ethanolamine plasmalogen deficiency: a logical causative factor in Alzheimer's disease and dementia. J Lipid Res. Jul. 2007;48(11):2485-2498.
Wood PL, Khan AM, Mankidy R, Smith T, Goodenowe D. Plasmalogen Deficit: A New and Testable Hypothesis for the Etiology of Alzheimer's Disease. In: De La Monte S, ed. *Alzheimer's Disease Pathogenesis-Core Concepts, Shifting Paradigms and Therapeutic Targets*. InTech; Sep. 2011.
Wood PL, Mankidy R, Ritchie S, et al. Circulating plasmalogen levels and Alzheimer Disease Assessment Scale-Cognitive scores in Alzheimer patients. *J Psychiatry Neurosci*. Jan. 2010;35(1):59-62.

(Continued)

*Primary Examiner* — Zinna Northington Davis
(74) *Attorney, Agent, or Firm* — Howson & Howson LLP; Colleen M. Schaller

(57) ABSTRACT

Provided herein are cyclic plasmenylethanolamines and plasmalogen precursors of formula A, wherein $R_1$ and $R_2$ are each, independently, a saturated, unsaturated, or polyunsaturated hydrocarbon group. Methods and uses thereof in the treatment of plasmalogen deficiency are also described. Cyclic plasmenylethanolamines described herein may act as plasmalogen precursors which, following administration, may be converted to at least one plasmalogen species, thereby elevating the plasmalogen level in a subject.

(Formula A)

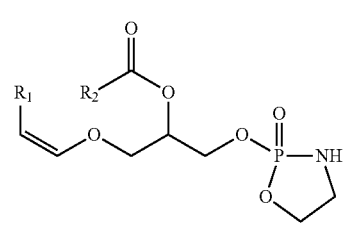

9 Claims, 22 Drawing Sheets

(56) References Cited

OTHER PUBLICATIONS

Dragonas C, Bertsch T, Sieber CC, Brosche T. Plasmalogens as a marker of elevated systemic oxidative stress in Parkinson's disease. *Clinical chemistry and laboratory medicine*: CCLM/ FESCC. Jul. 2009;47(7):894-897.

Fabelo N, Martin V, Santpere G, et al. Severe alterations in lipid composition of frontal cortex lipid rafts from Parkinson's disease and incidental Parkinson's disease. *Mol Med*. Jun. 2011;17(9-10):1107-1118.

Marin R, Fabelo N, Martin V, et al. Anomalies occurring in lipid profiles and protein distribution in frontal cortex lipid rafts in dementia with Lewy bodies disclose neurochemical traits partially shared by Alzheimer's and Parkinson's diseases. *Neurobiology of aging*. Sep. 2016;49:52-59.

Braverman NE, Moser AB. Functions of plasmalogen lipids in health and disease. *Biochim Biophys Acta*. May 2012; 1822(9):1442-1452.

Rog T, Koivuniemi A. The biophysical properties of ethanolamine plasmalogens revealed by atomistic molecular dynamics simulations. *Biochim Biophys Acta*. Oct. 2015;1858(1):97-103.

Kobayashi H, Yamagiwa N, et al. Identification of plasmalogen species as effective bioactive lipids to ameliorate the neurotoxic effects of arachidonic acid The 140th Annual Meeting of the Pharmaceutical Society of Japan (Kyoto) 27Q-am001S, Mar. 2020, with unofficial English translation.

Office Action issued in counterpart Japanese Patent Application No. 2019-554776, dated Jan. 5, 2022, with unofficial English translation.

PPI-1011

PPI-1040

PPI-1050

A)

B)

C)

A) 16:0/22:6

B) 16:0/18:1     16:0/18:2     16:0/18:3

16:0/20:4     16:0/20:5     16:0/22:4

Mean ± SEM, n=3.

Mean ± SEM, n=3.

Mean ± SEM, n=3

N=3. The endogenous unlabeled 16:0/22:6 VAG is showing for reference.

All plasmalogen species were significantly below baseline in the vehicle and PPI-1011. Mean ± SD, n=6 *-p<0.05 vs vehicle

CYCLIC PLASMENYLETHANOLAMINES

CROSS-REFERENCE TO RELATED APPLICATIONS

This is a National Stage Entry under 35 U.S.C. 371 of International Patent Application No. PCT/CA2018/050291, filed Mar. 12, 2018, which claims priority to U.S. Provisional Patent Application No. 62/486,037, filed Apr. 17, 2017. These applications are incorporated by reference herein.

FIELD OF INVENTION

The present invention relates generally to plasmalogens. More specifically, the present invention relates to plasmalogen precursors and cyclic plasmenylethanolamines.

BACKGROUND

Peroxisomes are intracellular membrane-bound organelles present in virtually every cell of the body. Several critical metabolic reactions are carried out exclusively in peroxisomes. One of the most critical reactions performed in peroxisomes is the biosynthesis of plasmalogens. Plasmalogens are a class of glycerophospholipids, characterized by a vinyl-ether-linked alkyl chain at the sn-1 position, an ester-linked long-chain fatty acid at the sn-2 position, and a head group attached to the sn-3 position by a phosphodiester linkage. The general formula for these molecules is represented by formula (I):

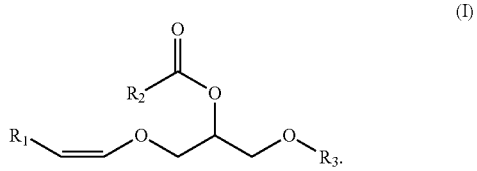

(I)

In humans, the sn-1 position (which incorporates the $R_1$ group) is most commonly derived from C16:0, C18:0 or C18:1 fatty alcohols. The sn-2 (which incorporates the $R_2$ group) position may be derived from saturated, monounsaturated or polyunsaturated fatty acids, while sn-3 is a head group, most commonly a phosphoethanolamine or phosphocholine.

Plasmalogens are present in tissues throughout the human body and represent approximately 15-20% of the total phospholipid content of cell membranes. This proportion varies widely by tissue type, with the brain, heart, neutrophils and eosinophils having the highest levels. Plasmalogens play a role in a number of diverse physiological functions including: structural component of cell membranes, secondary messengers, membrane fusion, ion transport, cholesterol efflux and as antioxidants [1,2]. Altered plasmalogen levels have been reported in different human diseases including peroxisomal biogenesis disorders, Zellweger spectrum disorder (Braverman, Raymond et al. 2016), Rhizomelic chondrodysplasia punctata [3,4], Alzheimer's disease [5-7], Parkinson's disease [8,9], Down syndrome [10] and Gaucher disease [11].

Biosynthesis of plasmalogens is initiated in the peroxisome by a series of non-redundant peroxisomal specific enzymes that create the ether bond which is reduced to the vinyl-ether within the endoplasmic reticulum. Peroxisomal biogenesis disorders (PBDs) represent a group of related, but heterogeneous, genetically-based medical conditions resulting from deficient peroxisomal function. These defects may either exist in a single enzyme involved in a peroxisomal—based function or in one of the genes critical for the assembly and biogenesis of the peroxisome. The clinical presentation and severity of these conditions is wide-ranging depending on the underlying genetic cause. Decreased levels of plasmalogens are central in the majority of peroxisomal biogenesis disorders, and are believed to be the main cause of morbidity. In general, plasmalogen levels directly correlate with severity of symptoms and prognosis.

Rhizomelic chondrodysplasia punctata (RCDP) is a subgroup of peroxisomal biogenesis disorders characterized by shortening of the bones, intellectual disability, significant developmental delays, distinctive facial features and/or respiratory problems. Diagnosis usually occurs shortly after birth due to the presence of cataracts and other clinical features, but is confirmed by genetic testing. There are 5 reported subtypes of RCDP, all have indistinguishable clinical features but result from mutations in different genes; Pex7 (RCDP1) [12-14], GNPAT (RCDP2) [15],AGPS (RCDP3) [16], FAR1 (RCDP4) (Buchert, Tawamie, et al., 2014, The American Journal of Human Genetics, 95, 602-610) and Pex5 (RCDP5)(Baroy, Koster et al., 2015, Human Molecular Genetics, 24(20):5845-5854). GNPAT and AGPS are enzymes involved in the biosynthesis of plasmalogens, FAR1 is involved in the biosynthesis of the fatty alcohol precursor of plasmalogen synthesis and Pex7 and Pex5 are involved in the biosynthesis of peroxisomes. All 5 types have depleted plasmalogen levels, with prognosis positively correlated with increasing plasmalogen levels [3,4]. Prevalence is estimated at 1 per 100,000 live births. In patients who survive the first few months of life, only 50% survive until age 5 and nearly all will succumb to the disease by adolescence. Recurrent respiratory infections are common with 80% of deaths in patients who survive past 6 months being reported as secondary to respiratory problems [17]. There are less than 100 cases reported currently in the US, although it is believed that the disorder is under-reported.

There are currently no disease modifying therapies available for RCDP. Attempts to increase plasmalogen levels with dietary plasmalogen precursors have shown modest efficacy, however have ultimately failed in the clinic due to the very high dose and lengthy time-course required to elevate plasmalogen levels [18-21].

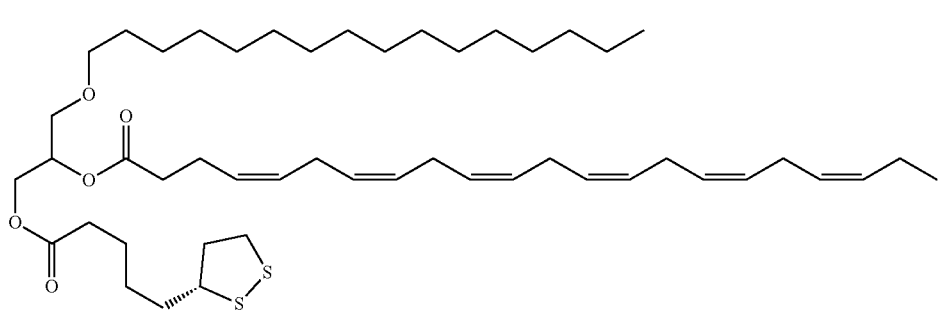

(PPI-1011)

Historical studies with other plasmalogen precursors (batyl alcohol and PPI-1011) have suggested that individuals or animals with PBD or RCDP do not effectively metabolize these precursors into the desired plasmalogen species. It is unclear why this process does not function effectively, but the effect of severely reduced or absent plasmalogen levels throughout development is likely leading to this impaired function.

An alternative, additional, and/or improved plasmalogen precursor is desirable.

SUMMARY OF INVENTION

It is an object of the invention to provide plasmalogen precursors for elevating the level of at least one plasmalogen in a cell or subject in need thereof.

In one embodiment, there is provided a method of elevating at least one plasmalogen level in a subject. The method comprises:

administering to the subject a pharmaceutically effective amount of at least one cyclic plasmenylethanolamine having formula A:

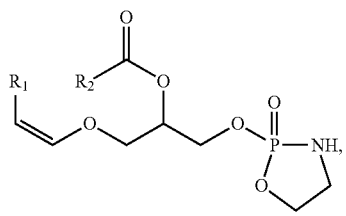

(A)

or a pharmaceutically acceptable salt or solvate thereof, wherein $R_1$ and $R_2$ are each, independently, a saturated, unsaturated, or polyunsaturated, optionally substituted hydrocarbon group, wherein following administration, the cyclic plasmenylethanolamine is converted to at least one plasmalogen species, thereby elevating the plasmalogen level in the subject.

In certain embodiments, $R_1$ may be selected (in chain length and saturation level) to provide a hydrocarbon chain of a desired fatty alcohol group for the sn-1 position, and $R_2$ may be selected (in chain length and saturation level) to provide a hydrocarbon chain of a desired fatty acid group for the sn-2 position. In certain embodiments, the fatty acid, fatty alcohol, or both, may be an endogenously occurring fatty acid and/or fatty alcohol.

In certain embodiments, $R_1$, $R_2$, or both, may be an optionally substituted $C_1$-$C_{28}$ hydrocarbon group which may be an alkane, alkene, or alkyne hydrocarbon group. In certain embodiments, $R_1$, $R_2$, or both, may each independently have up to 6 double bonds. In certain embodiments, $R_1$, $R_2$, or both, may be a $C_1$-$C_{28}$ hydrocarbon group which is, optionally, hydroxylated (i.e. which features one or more

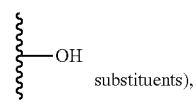 [SMILES: *O]

substituents), which comprises one or more alkene and/or alkyne functional groups, which comprises one or more ketone functional groups, which comprises one or more lower alkyl ($C_1$-$C_6$) hydrocarbon groups, or any combination thereof.

In certain embodiments, $R_1$, $R_2$, or both, may be an optionally substituted $C_8$-$C_{26}$ hydrocarbon group.

Typically, $R_1$ will be selected (in chain length and saturation level) to provide the hydrocarbon chain of a desired fatty alcohol group for the sn-1 position, and $R_2$ will be selected (in chain length and saturation level) to provide the hydrocarbon chain of a desired fatty acid group for the sn-2 position. The fatty alcohol or fatty acid may be naturally derived or synthetically produced.

In other embodiments of the described method, the subject may suffer from a plasmalogen deficiency, a peroxisomal biogenesis disorder, or both. For example, the subject may suffer from rhizomelic chondrodysplasia punctata (RCDP), Zellweger spectrum disorder or other plasmalogen deficiency disorder. In still another embodiment, the subject may be a subject having Alzheimer's disease (AD), or Parkinson's disease (PD).

In particular embodiments, the cyclic plasmenylethanolamine may be:

PPI-1040

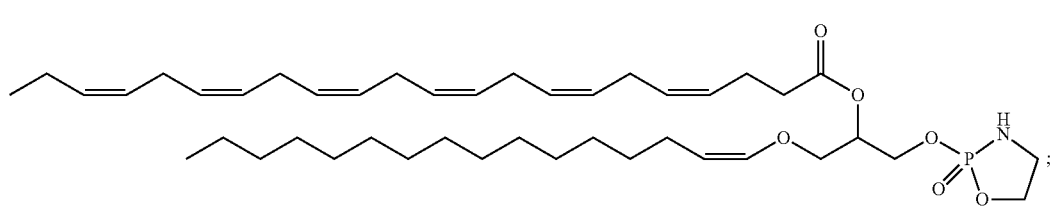

;

PPI-1054

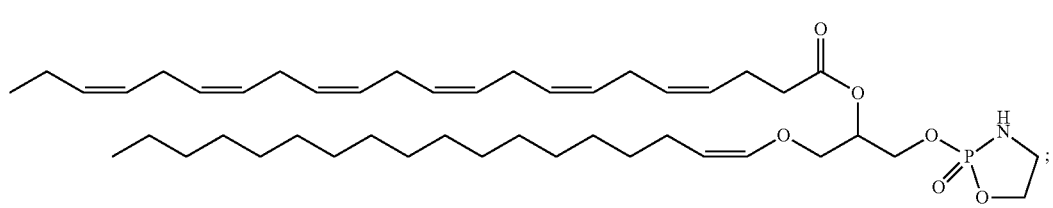

;

PPI-1056

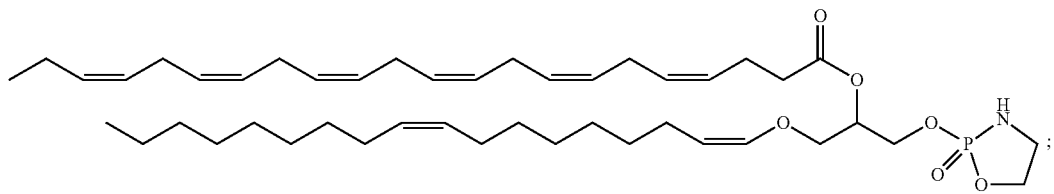

PPI-1063

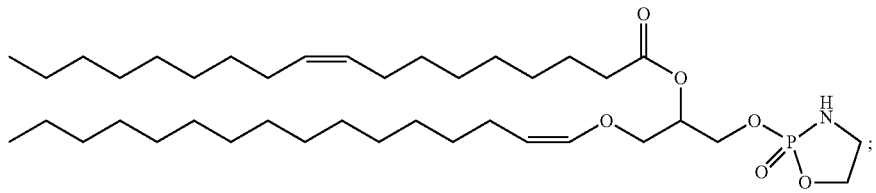

PPI-1045

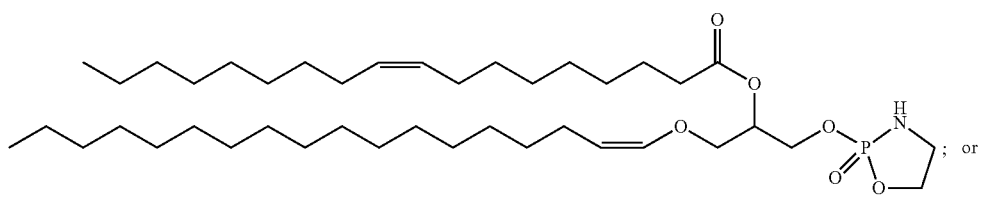
; or

PPI-1046

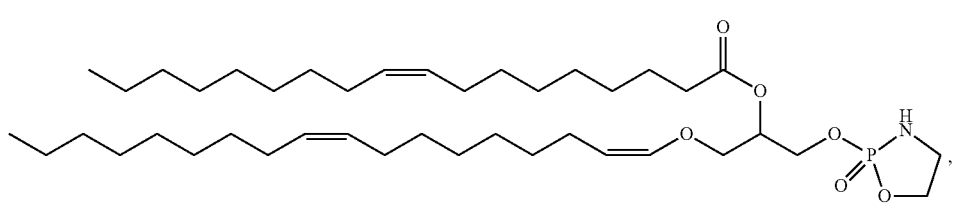

or a pharmaceutically acceptable salt and/or solvate thereof;

or any combination thereof.

Also described herein is the use of at least one cyclic plasmenylethanolamine having formula A as described above for elevating at least one plasmalogen level in a subject in need thereof, wherein the cyclic plasmenylethanolamine is for administration to the subject followed by conversion to at least one plasmalogen species, thereby elevating the plasmalogen level in the subject. The cyclic plasmenylethanolamines of formula A may also be used in the manufacture of a medicament for elevating plasmalogen levels, as described.

In further embodiments there is also provided a plasmalogen precursor having formula A:

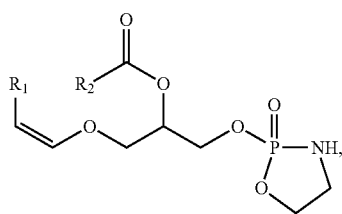

(A)

or a pharmaceutically acceptable salt or solvate thereof, wherein $R_1$ and $R_2$ are as described above.

There is also provided a pharmaceutical composition comprising the plasmalogen precursor, and at least one pharmaceutically acceptable carrier, diluent, or excipient. Kits are also described, which include the described plasmalogen precursor, in which the kit is for elevating a plasmalogen level in a cell, or in a subject in need thereof. Such kits may, in certain embodiments, include instructions for formulating and/or administering the plasmalogen precursor to the cell or subject and/or may include a container for the plasmalogen precursor.

In another embodiment, there is provided herein a method of increasing long term potentiation (LTP) between neurons, said method comprising:

treating the neurons with at least one cyclic plasmenylethanolamine having formula A:

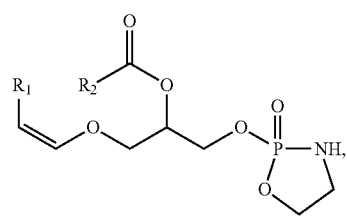

(A)

or a pharmaceutically acceptable salt or solvate thereof, wherein $R_1$ and $R_2$ are each, independently, a saturated, unsaturated, or polyunsaturated, optionally substituted hydrocarbon group.

In another embodiment, there is provided herein a method of increasing long term potentiation (LTP) in a subject in need thereof, said method comprising:

administering to said subject at least one cyclic plasmenylethanolamine having formula A:

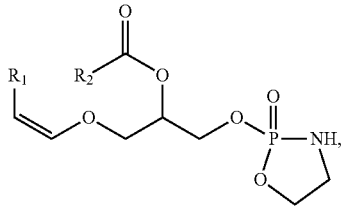

(A)

or a pharmaceutically acceptable salt or solvate thereof, wherein $R_1$ and $R_2$ are each, independently, a saturated, unsaturated, or polyunsaturated, optionally substituted, hydrocarbon group.

In certain embodiments, the subject may have Alzheimer's disease or Parkinson's disease.

In another embodiment, there is provided herein a method of treating or preventing Alzheimer's disease or Parkinson's disease in a subject in need thereof, said method comprising:
administering to said subject at least one cyclic plasmenylethanolamine having formula A:

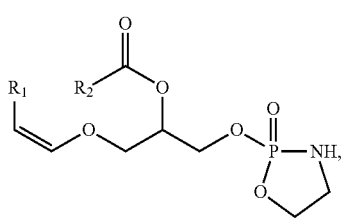

(A)

or a pharmaceutically acceptable salt or solvate thereof, wherein $R_1$ and $R_2$ are each, independently, a saturated, unsaturated, or polyunsaturated, optionally substituted hydrocarbon group.

In still another embodiment, there is provided herein a method of treating or preventing a plasmalogen deficient neurodegenerative disease in a subject in need thereof, said method comprising:
administering to said subject at least one cyclic plasmenylethanolamine having formula A:

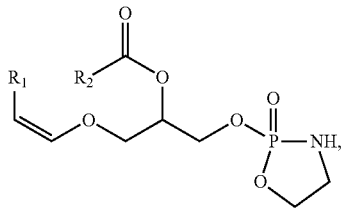

(A)

or a pharmaceutically acceptable salt or solvate thereof, wherein $R_1$ and $R_2$ are each, independently, a saturated, unsaturated, or polyunsaturated, optionally substituted hydrocarbon group.

In another embodiment, the plasmalogen deficient neurodegenerative disease may be Alzheimer's disease or Parkinson's disease.

In yet another embodiment, there is provided herein a method of elevating at least one plasmalogen level in a subject in need thereof, said method comprising:
administering to said subject at least one compound of formula A':

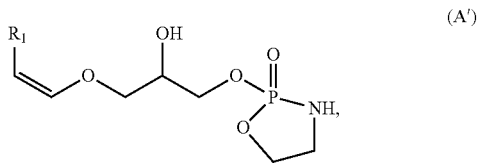

(A')

or a pharmaceutically acceptable salt or solvate thereof, wherein $R_1$ is a saturated, unsaturated, or polyunsaturated, optionally substituted hydrocarbon group,
wherein following administration, said compound is converted to at least one plasmalogen species, thereby elevating the plasmalogen level in the subject.

In yet another embodiment, $R_1$ may be an optionally substituted $C_1$-$C_{28}$ hydrocarbon group. In still another embodiment, $R_1$ may comprise up to 6 double bonds. In another embodiment, $R_1$ may be a hydrocarbon chain of a fatty alcohol or fatty acid.

In still another embodiment, the subject may be a subject suffering from a plasmalogen deficiency. In another embodiment, the subject may be a subject having a peroxisomal biogenesis disorder. In still another embodiment, the subject may be a subject having rhizomelic chondrodysplasia punctata (RCDP) or Zellweger spectrum disorder. In still another embodiment, the subject may be a subject having Alzheimer's disease or Parkinson's disease In another embodiment, there is provided herein a use of a compound of formula A', or a pharmaceutically acceptable salt or solvate thereof, for elevating at least one plasmalogen level in a subject in need thereof, wherein said compound is for administration to the subject followed by conversion to at least one plasmalogen species, thereby elevating the plasmalogen level in the subject.

In another embodiment, there is provided herein a use of at least one compound of formula A', or a pharmaceutically acceptable salt or solvate thereof, in the manufacture of a medicament for elevating at least one plasmalogen level in a subject in need thereof, wherein said compound is for administration to the subject followed by conversion to at least one plasmalogen species, thereby elevating the plasmalogen level in the subject.

In yet another embodiment, there is provided herein a compound of formula A':

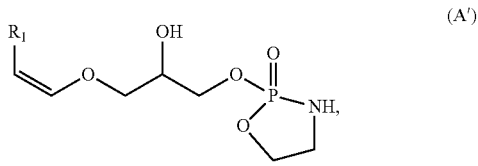

(A')

or a pharmaceutically acceptable salt or solvate thereof, wherein $R_1$ is a saturated, unsaturated, or polyunsaturated, optionally substituted hydrocarbon group,
for use in elevating at least one plasmalogen level in a subject in need thereof, wherein said compound is for administration to the subject followed by conversion to at least one plasmalogen species, thereby elevating the plasmalogen level in the subject.

In still another embodiment, there is provided herein a plasmalogen precursor having formula A':

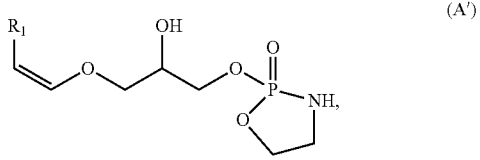

or a pharmaceutically acceptable salt or solvate thereof,
wherein $R_1$ is a saturated, unsaturated, or polyunsaturated, optionally substituted hydrocarbon group.

In another embodiment, there is provided herein a pharmaceutical composition comprising at least one compound, cyclic plasmenylethanolamine, or plasmalogen precursor as defined herein, and, optionally, at least one pharmaceutically acceptable carrier, diluent, or excipient.

In another embodiment, there is provided herein a kit for elevating a plasmalogen level in a cell, or in a subject in need thereof, the kit comprising:

at least one plasmalogen precursor having formula A':

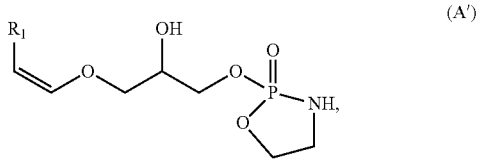

or a pharmaceutically acceptable salt or solvate thereof,
wherein $R_1$ is a saturated, unsaturated, or polyunsaturated, optionally substituted hydrocarbon group; and instructions for administering the plasmalogen precursor to the cell or subject.

In yet another embodiment, there is provided herein a compound of formula A':

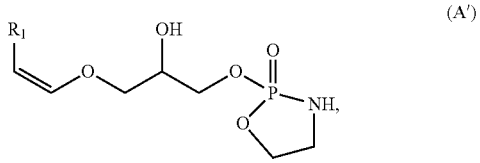

or a pharmaceutically acceptable salt or solvate thereof,
wherein $R_1$ is a saturated, unsaturated, or polyunsaturated, optionally substituted hydrocarbon group.

In another embodiment, there is provided herein a method of increasing long term potentiation (LTP) between neurons, said method comprising:

treating the neurons with at least one compound of formula A':

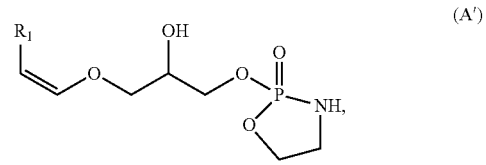

or a pharmaceutically acceptable salt or solvate thereof,
wherein $R_1$ is a saturated, unsaturated, or polyunsaturated, optionally substituted hydrocarbon group.

In still another embodiment, there is provided herein a method of increasing long term potentiation (LTP) in a subject in need thereof, said method comprising:

administering to said subject at least one compound of formula A':

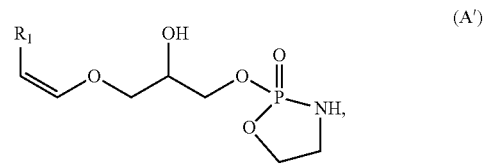

or a pharmaceutically acceptable salt or solvate thereof,
wherein $R_1$ is a saturated, unsaturated, or polyunsaturated, optionally substituted, hydrocarbon group.

In another embodiment, the subject may be a subject having Alzheimer's disease or Parkinson's disease.

In yet another embodiment, there is provided herein a method of treating or preventing Alzheimer's disease or Parkinson's disease in a subject in need thereof, said method comprising:

administering to said subject at least one compound of formula A':

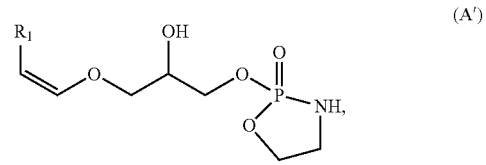

or a pharmaceutically acceptable salt or solvate thereof,
wherein $R_1$ is a saturated, unsaturated, or polyunsaturated, optionally substituted hydrocarbon group.

In still another embodiment, there is provided herein a method of treating or preventing a plasmalogen deficient neurodegenerative disease in a subject in need thereof, said method comprising:

administering to said subject at least one compound of formula A':

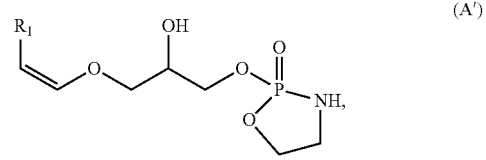

or a pharmaceutically acceptable salt or solvate thereof, wherein $R_1$ is a saturated, unsaturated, or polyunsaturated, optionally substituted hydrocarbon group.

In yet another embodiment, the plasmalogen deficient neurodegenerative disease may be Alzheimer's disease or Parkinson's disease.

In another embodiment, there is provided herein a pharmaceutical composition comprising two or more compounds selected from:

formula (A) as described herein;
formula (A') as described herein; and/or
formula (B) as described herein,
or pharmaceutically acceptable salts or solvates thereof.

BRIEF DESCRIPTION OF DRAWINGS

These and other features will become more apparent from the following description in which reference is made to the appended drawings, wherein.

DETAILED DESCRIPTION

Described herein are cyclic plasmenylethanolamines and plasmalogen precursors. Methods and uses thereof in the treatment of plasmalogen deficiency are also described. It will be appreciated that embodiments and examples are provided for illustrative purposes intended for those skilled in the art, and are not meant to be limiting in any way.

One or more currently preferred embodiments have been described by way of example. It will be apparent to persons skilled in the art that a number of variations and modifications can be made without departing from the scope of the invention as defined in the claims.

As described in detail herein, cyclic plasmenylethanolamines have been developed as a class of plasmalogen precursors which may be converted to an endogenous plasmalogen species, or a mimic thereof. Cyclic plasmenylethanolamines feature a cyclic ethanolamine functional group at position sn-3 (see Formula A) which may, in certain embodiments, improve the stability of the vinyl-ether bond.

Formula A

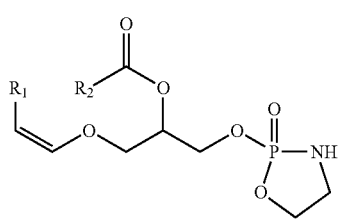

Figure 1:
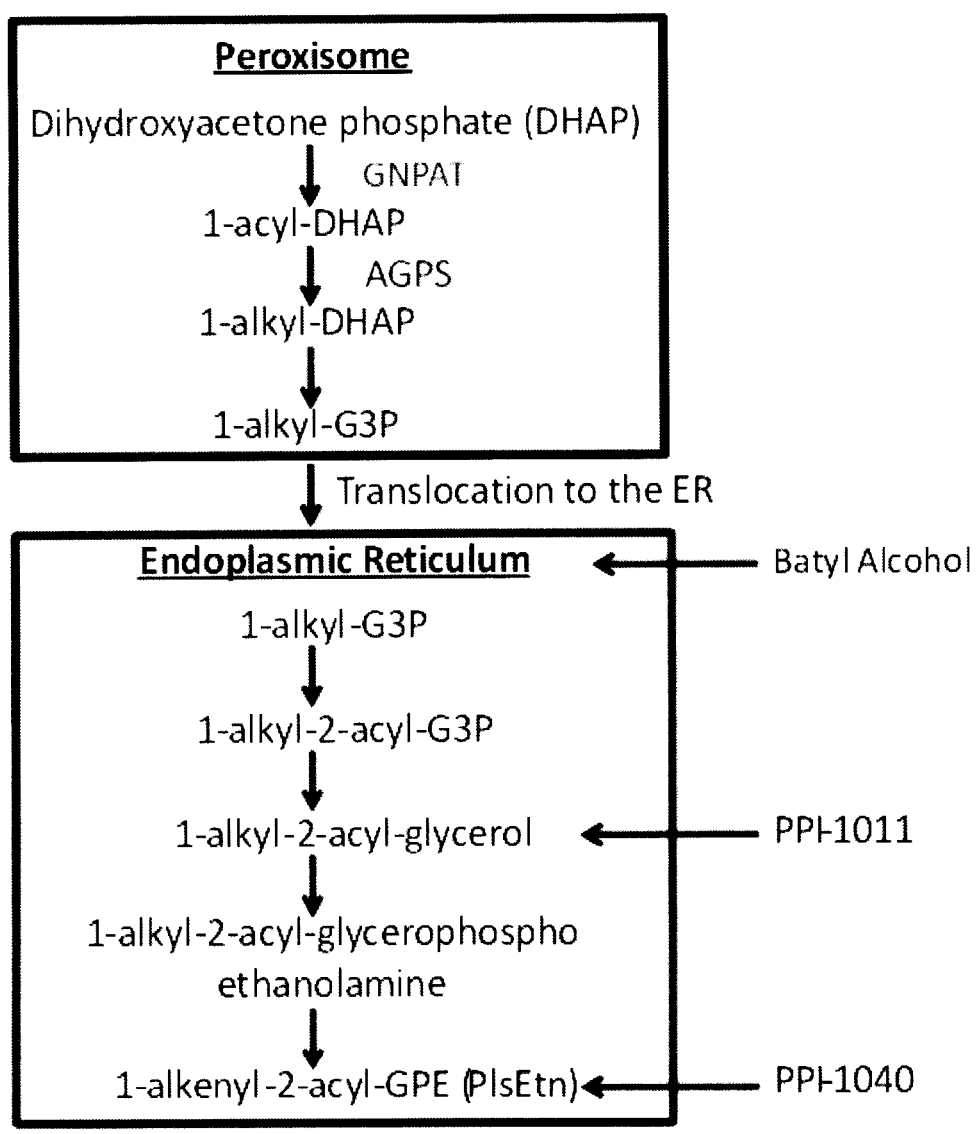
FIG. 1 shows the ethanolamine plasmalogen biosynthetic pathway, outlining the metabolic steps and organelles involved. Plasmalogen replacement examples, including PPI-1040, are listed on the right side along with an arrow indicating the point at which each precursor enters the metabolic pathway.

Experimental examples provided in the following sections indicate that cyclic plasmenylethanolamines provided endogenously available plasmalogen, and compared favorably to plasmalogen precursor PPI-1011. As well, cyclic plasmenylethanolamines may enter the ethanolamine plasmalogen biosynthetic pathway at a very late stage, which may be desirable in comparison to alkyl glycerols including batyl and chimyl alcohol (see FIG. 1) which involve additional enzymatic processing.

The synthesis of cyclic-plasmenylethanolamines has been described in Canadian Patent No. 2,812,178, which is herein incorporated by reference in its entirety.

In certain embodiments, there is provided herein a method of elevating at least one plasmalogen level in a subject in need thereof, said method comprising:

administering to said subject at least one cyclic plasmenylethanolamine having formula A:

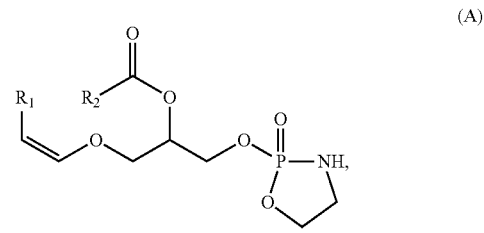

or a pharmaceutically acceptable salt or solvate thereof,
wherein $R_1$ and $R_2$ are each, independently, a saturated, unsaturated, or polyunsaturated, optionally substituted hydrocarbon group,
wherein following administration, said cyclic plasmenylethanolamine is converted to at least one plasmalogen species, thereby elevating the plasmalogen level in the subject.

Also provided herein is the use of at least one cyclic plasmenylethanolamine having formula A:

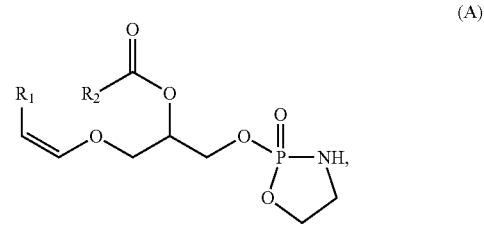

or a pharmaceutically acceptable salt or solvate thereof,
wherein $R_1$ and $R_2$ are each, independently, a saturated, unsaturated, or polyunsaturated, optionally substituted hydrocarbon group,
for elevating a plasmalogen level in a subject in need thereof, wherein said cyclic plasmenylethanolamine is for administration to the subject followed by conversion to at least one plasmalogen species, thereby elevating the plasmalogen level in the subject.

In certain embodiments, $R_1$ may be selected (in chain length and saturation level) to provide a hydrocarbon chain of a desired fatty alcohol group for the sn-1 position, and $R_2$ may be selected (in chain length and saturation level) to provide a hydrocarbon chain of a desired fatty acid group for the sn-2 position. In certain embodiments, the fatty acid, fatty alcohol, or both, may be an endogenously occurring fatty acid and/or fatty alcohol. Examples of endogenous and/or naturally occurring fatty acids/fatty alcohols may be found, for example, at the LipidWeb website:

http://lipidhome.co.uk/lipids/fa-eic/fa-sat/index.htm, http://aocs.files.cms-plus.com/LipidsLibrary/images/Importedfiles/lipidlibrary/Lipids/fa_mono/file.pdf, and http://www.lipidhome.co.uk/lipids/fa-eic/fa-poly/index.htm;

in The Lipid Handbook, Second Edition, Gunstone et al. (1994), Chapman & Hall;

in "The Nomenclature of Lipids" published in the Journal of Lipid Research, volume 19, 1978, pages 114-128; and in Food Lipids: Chemistry, Nutrition, and Biotechnology, 2nd Edition, Marcel Dekker, Inc., CRC, 2002, Chapter 1, by O'Keefe;

each of which are herein incorporated by reference in their entireties.

In certain embodiments, $R_1$, $R_2$, or both, may be an optionally substituted $C_1$-$C_{28}$ hydrocarbon group which may be an alkane, alkene, or alkyne hydrocarbon group. In certain embodiments, $R_1$, $R_2$, or both, may each independently have up to 6 double bonds. In certain embodiments, $R_1$, $R_2$, or both, may be a $C_1$-$C_{28}$ hydrocarbon group which is hydroxylated (i.e. which features one or more

substituents), which comprises one or more alkene and/or alkyne functional groups, which comprises one or more ketone functional groups, which comprises one or more lower alkyl ($C_1$-$C_6$) hydrocarbon groups, or any combination thereof.

In certain embodiments, $R_1$, $R_2$, or both, may be an optionally substituted $C_8$-$C_{26}$ hydrocarbon group.

In certain embodiments, cyclic plasmenylethanolamines of formula (A) may include those in which $R_1$, $R_2$, or both, are optionally substituted $C_1$-$C_{28}$ hydrocarbon groups. In certain embodiments, $R_1$, $R_2$, or both, may each independently comprise up to 6 double bonds. In certain embodiments, $R_1$, $R_2$, or both, may comprise hydrocarbon chains of a fatty alcohol or fatty acid, such as an endogenous fatty alcohol or fatty acid, as described in further detail herein.

In another embodiment of the methods and uses described herein, the subject may be a subject suffering from a plasmalogen deficiency. By way of example, the subject may suffer from a peroxisomal biogenesis disorder such as rhizomelic chondrodysplasia punctata (RCDP) or Zellweger spectrum disorder.

In certain embodiments, the cyclic plasmenylethanolamine may be:

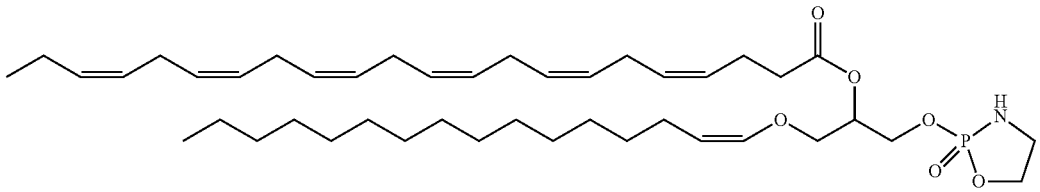 [SMILES: CC/C=C\C/C=C\C/C=C\C/C=C\C/C=C\C/C=C\CCC(=O)OC(CO/C=C\CCCCCCCCCCCCCC)COP1(=O)NCCO1]

1-(((Z)-hexadec-1-en-1-yl)oxy)-3-((2-oxido-1,3,2-oxazaphospholidin-2-yl)oxy)propan-2-yl (4Z,7Z,10Z,13Z,16Z,19Z)-docosa-4,7,10,13,16,19-hexaenoate (PPI-1040)

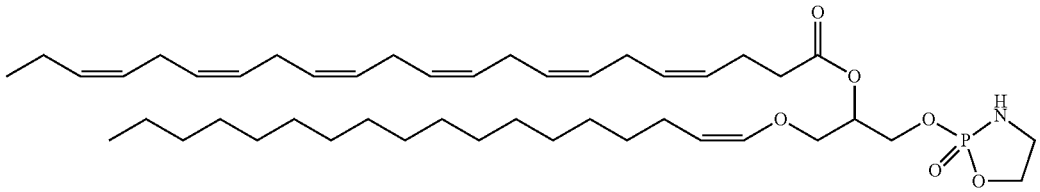 [SMILES: CC/C=C\C/C=C\C/C=C\C/C=C\C/C=C\C/C=C\CCC(=O)OC(CO/C=C\CCCCCCCCCCCCCCCC)COP1(=O)NCCO1]

1-(((Z)-octadec-1-en-1-yl)oxy)-3-((2-oxido-1,3,2-oxazaphospholidin-2-yl)oxy)propan-2-yl (4Z,7Z,10Z,13Z,16Z,19Z)-docosa-4,7,10,13,16,19-hexaenoate (PPI-1054)

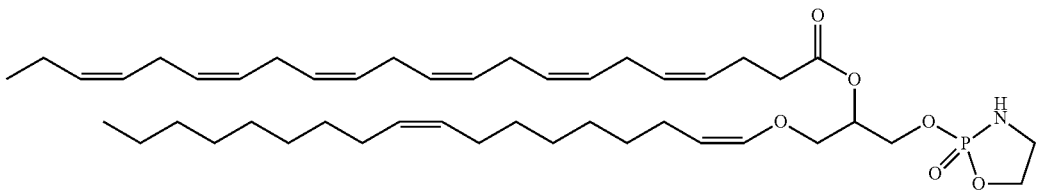 [SMILES: CC/C=C\C/C=C\C/C=C\C/C=C\C/C=C\C/C=C\CCC(=O)OC(CO/C=C\CCCCCC/C=C\CCCCCCCC)COP1(=O)NCCO1]

1-(((1Z,9Z)-octadeca-1,9-dien-1-yl)oxy)-3-((2-oxido-1,3,2-oxazaphospholidin-2-yl)oxy)propan-2-yl (4Z,7Z,10Z,13Z,16Z,19Z)-docosa-4,7,10,13,16,19-hexaenoate (PPI-1056)

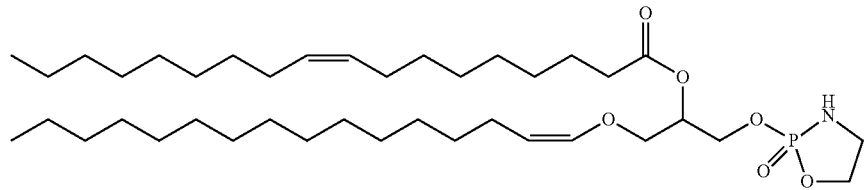 [SMILES: CCCCCCCC/C=C\CCCCCCCC(=O)OC(CO/C=C\CCCCCCCCCCCCCC)COP1(=O)NCCO1]

1-(((1Z,9Z)-octadeca-1,9-dien-1-yl)oxy)-3-((2-oxido-1,3,2-oxazaphospholidin-2-yl)oxy)propan-2-yl palmitate (PPI-1063)

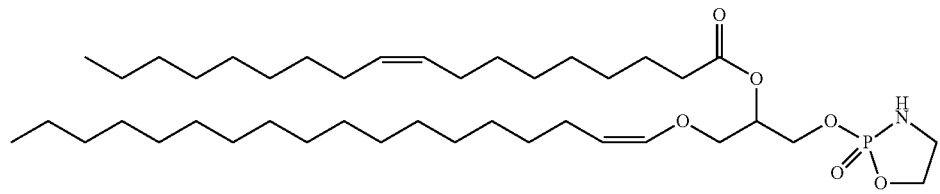 [SMILES: CCCCCCCC/C=C\CCCCCCCC(=O)OC(CO/C=C\CCCCCCCCCCCCCCCC)COP1(=O)NCCO1]

1-(((Z)-hexadec-1-en-1-yl)oxy)-3-((2-oxido-1,3,2-oxazaphospholidin-2-yl)oxy)propan-2-yl oleate (PPI-1045); or

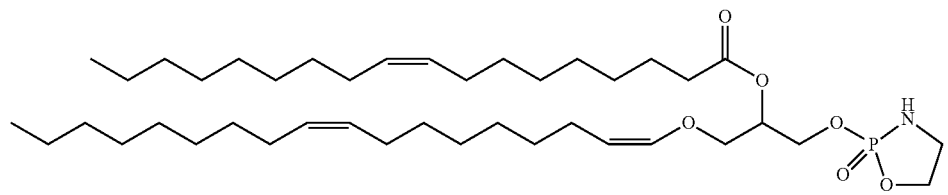 [SMILES: CCCCCCCC/C=C\CCCCCC/C=C\OCC(COP1(=O)NCCO1)OC(=O)CCCCCCC/C=C\CCCCCCCC]

1-(((Z)-octadec-1-en-1-yl)oxy)-3-((2-oxido-1,3,2-oxazaphospholidin-2-yl)oxy)propan-2-yl oleate (PPI-1046)

or a pharmaceutically acceptable salt or solvate thereof, or any combination thereof.

As will be understood, in certain embodiments, the $R_1$ and/or $R_2$ groups of the cyclic plasmenylethanolamine may be selected so as to favor elevation of a particular plasmalogen of interest in the subject such as, for example, an endogenous plasmalogen. Where, for example, the plasmalogen of interest is 16:0/22:6 ethanolamine plasmalogen (PlsEtn), the $R_1$ and $R_2$ groups may be selected accordingly as:

PPI-1040

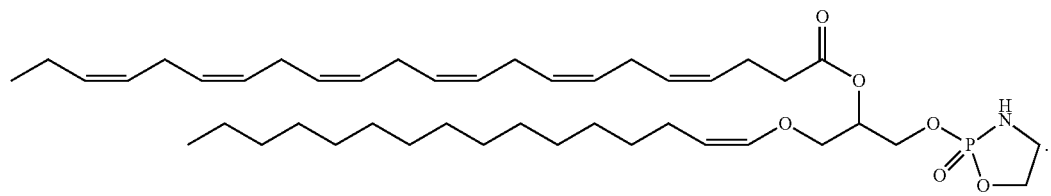

It will be appreciated by those of ordinary skill in the art that the vinyl-ether double bond present in the general plasmalogen structure, as represented by formula (A), is encompassed in the term "plasmalogen" and therefore is not included in the terminology used for the substituent included at the sn-1 position. It is a general naming convention to not include this double bond. Thus, for example, in the PPI-1040 embodiment illustrated above the 16:0 sidechain at the sn-1 position includes a total of 16 carbons and no further double bonds in addition to the double bond present in the vinyl-ether moiety.

The groups chosen for the $R_1$ and $R_2$ positions can be selected based on what is most desirable to elevate in a subject. This can, therefore, be tailored based on what plasmalogens are most severely decreased in an individual, or what functional effect is needed in an individual. For example, in one embodiment of the invention a molecule with 18:0/18:1 at sn-1 and sn-2 could be selected to increase levels of myelin, since that is the endogenous plasmalogen most commonly incorporated into the myelin structure. A polyunsaturated sn-2 substituent such as DHA, on the other hand, can be selected in further embodiments to improve vesicular fusion and membrane protein function.

The groups chosen for the $R_1$ and/or $R_2$ positions may be selected based on what is desirable to elevate in a subject. In certain embodiments, compositions described herein may be tailored for a particular subject, subject group, or disease or condition, based on which plasmalogens are depleted or desirable to elevate and/or based on which plasmalogens are likely to be beneficial in the particular application. In certain embodiments, compositions described herein may comprise two or more different compounds as described herein, the compounds being selected to provide a tailored treatment. In certain embodiments, compounds may be selected from any of formulas (A), (A'), and (B). In certain embodiments, the two or more compounds may be for administration together or separately. In certain embodiments, the two or more compounds may be for administration simultaneously (either as a combined mixture, or as separate formulations administered at substantially the same time), or sequentially.

In certain embodiments, pharmaceutical compositions described herein may comprise two or more compounds selected from: formula (A); formula (A'); and/or formula (B); or pharmaceutically acceptable salts or solvates thereof.

As will be understood, and without wishing to be limited by theory, upon exposure to an aqueous or acidic environment, including but not limited to that found in human circulation or digestive tract, the cyclized ethanolamine ring found in compounds of formula A may be hydrolyzed into an open ring phosphoethanolamine head group (formula B). In certain embodiments, such open ring phosphoethanolamines may be endogenous open ring phosphoethanolamines. Compounds of formula B may then act as endogenous plasmalogen species in vivo or in vitro, for example.

(formula B)

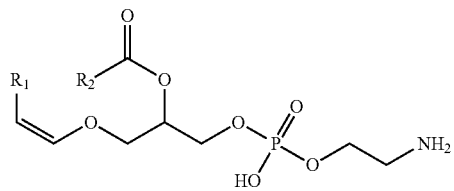

As will also be understood, references herein to compounds of formula B, and references to a cyclic plasmenylethanolamine or plasmalogen precursor of formula (A), references to compounds of formula A', and references to examples such as PPI-1040, PPI-1054, PPI-1056, PPI-1063, PPI-1045, and PPI-1046, will be understood as also encompassing pharmaceutically acceptable salts and solvates thereof. In certain embodiments, salts may include any suitable alkali metal salt such as a sodium or potassium salt, for example. In certain embodiments, salts may include a chloride salt or other suitable halogen salt, for example. In certain embodiments, solvates may include oils or emulsions such as, for example, Neobee vehicle.

As will be understood, in certain non-limiting embodiments, compounds as described herein may contain one or more chiral centers. Typically, such compounds may be prepared as a racemic mixture. If desired, however, such compounds may be prepared or isolated as pure stereoisomers, i.e., as individual enantiomers or diastereomers, or as stereoisomer-enriched mixtures. All such stereoisomers (and enriched mixtures) of the compounds of formula A, A', and B are included within the scope of this description. Pure stereoisomers (or enriched mixtures) may be prepared using, for example, optically active starting material or stereoselective reagents known in the art. Alternatively, racemic mixtures of such compounds may be separated using, for example, chiral column chromatography, chiral resolving agents, and the like. Chemical compounds described herein may include both the (+) and (−) stereoisomers, or either the (+) or (−) stereoisomer. In certain preferred embodiments, which are not intended to be limiting in any way, the described compounds may be prepared or isolated as pure Cis or R stereoisomers.

In certain embodiments, the central carbon the glycerol moiety in formula (A), (A'), and/or (B) may be enantiomerically pure R, enantiomerically pure S, may be enantiomerically enriched R, enantiomerically enriched S, or may be racemic.

As will be understood, in certain embodiments, one or both of the $R_1$ and $R_2$ groups of formula (A) may be each, independently, a saturated, unsaturated, or polyunsaturated, optionally substituted hydrocarbon-based group. Where $R_1$ and $R_2$ groups contain one or more double bonds, the double bonds may be all cis, all trans, or a mix of cis and trans. In certain embodiments, for example, all double bonds present in $R_1$ and $R_2$ groups may be cis. Preparations of cyclic plasmenylethanolamines or plasmalogen precursors described herein may be provided as pure preparations, enriched preparations, or as mixtures in which the stereochemistry of the $R_1$ and $R_2$ groups within the preparation is varied.

It will further be understood that in certain embodiments, there is also provided herein cyclic plasmenylethanolamines or plasmalogen precursors of formula (A), such as PPI-1040, PPI-1054, PPI-1056, PPI-1063, PPI-1045, and PPI-1046, as well as compounds of formula (A') and/or (B), which are radiolabelled, isotopically labelled, or otherwise labelled. Such labelled compounds may be used, for example, to study or trace distribution post-administration. By way of example, in certain embodiments, cyclic plasmenylethanolamines or plasmalogen precursors of formula (A) as described herein may comprise one or more deuterium or tritium labels. In certain embodiments, for example, cyclic plasmenylethanolamines or plasmalogen precursors of formula (A) or compounds of formuala (A') or (B) as described herein may comprise one or more $^{13}C$ labels or $^{14}C$ labels. In certain embodiments, a label may be included at the sn-3 position, such as a $^{32}$P label for example. As will be understood, in certain embodiments, labels may be positioned so as to allow for tracing of individual portions of the cyclic plasmenylethanolamines or plasmalogen precursors, for example by incorporating one or more labels at the sn-1 and/or sn-2 and/or glycerol portions. As will be understood, in certain embodiments, labels may be introduced during synthesis of the cyclic plasmenylethanolamines or plasmalogen precursors by, for example, using appropriate commercially labelled starting materials and/or reagents.

In the experiments described herein below, it has been identified that the substituent at sn-2 of the cyclic plasmenylethanolamine of formula (A) may be modified following introduction into the cell and/or subject. Accordingly, results indicate that processing may occur to install different groups on the sn-2 glycerol hydroxyl moiety. As such, it is contemplated herein that in certain embodiments, a compound of formula A' may be used in place of, or in combination with, a compound of formula A:

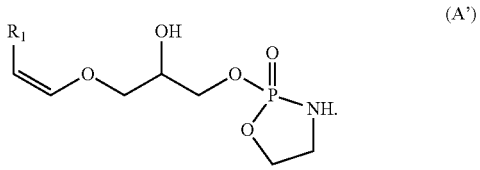

(A')

As well, in certain embodiments, it is contemplated that compounds of formula A and/or formula A' may be used in combination with each other, and/or in combination with one or more compounds of formula (B).

As also described herein, the cyclic plasmenylethanolamine ring of compounds of formula (A) may open, thus generating compounds of formula (B). In certain embodiments, preparations of compounds of formula (A) may thus accumulate an amount of compounds of formula B over time, and so in certain embodiments compounds of formula (A) may be used in combination with compounds of formula (B) in the methods described herein.

When describing the alkyl/acyl fatty acids and fatty alcohols and biologically active compounds, pharmaceutical compositions and methods, the following terms have the following meanings unless otherwise specified.

Fatty acids include aliphatic monocarboxylic acids, derived from, or contained in esterified form in an animal or vegetable fat oil or wax. Natural fatty acids commonly have a chain of 4 to 28 carbons (usually unbranched and even numbered), which may be saturated or unsaturated. These are known as acyclic aliphatic carboxylic acids.

Within the meaning of saturated fatty acids, the term "saturated" refers to carbons (apart from the initial carboxylic [—COOH] group) containing as many hydrogens as possible. In other words, the omega (ω) end containing 3 hydrogen atoms ($CH_3$—), and carbon within the chain containing 2 hydrogen atoms.

Unsaturated fatty acids are of similar form to saturated fatty acids, except that one or more alkenyl functional groups exist along the chain, with each alkene substituting a single bonded —$CH_2$—$CH_2$— part of the chain with a double-bonded —CH=CH— portion (that is, a carbon double-bonded to another carbon). These are named as CIS/TRANS and C:D where C represents number of carbon atoms and D represents double bonds.

Fatty alcohols may range from 4-28 carbons, and are typically derived from natural fats and oils. The precise chain length varies with the source. They are usually high-molecular-weight, straight-chain primary alcohols, but can also be branched. Fatty alcohols usually have an even number of carbon atoms and a single alcohol group (—OH) attached to the terminal carbon. They may be saturated or unsaturated as described further herein. Some commercially important fatty alcohols are lauryl, stearyl, and oleyl alcohols. They are colourless oily liquids (for smaller carbon numbers) or waxy solids, although impure samples may appear yellow.

A pharmaceutical agent or drug refers to a chemical compound or composition capable of inducing a desired therapeutic or prophylactic effect when properly administered to a subject.

The term effective amount means an amount of drug or pharmaceutical agent which will elicit the biological or medical response of a tissue, system, animal or human that is being sought, for instance, by a researcher or clinician. Furthermore, the term therapeutically effective amount means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope an amount effective to enhance normal physiological function.

Other chemistry terms herein are used according to conventional usage in the art, as exemplified by The McGraw-Hill Dictionary of Chemical Terms (1985) and the Condensed Chemical Dictionary (1981).

When employed as pharmaceuticals, compounds as described herein are typically administered in the form of a pharmaceutical composition. Such compositions may be prepared using procedures well known in the pharmaceutical art and comprise at least one active compound.

Generally, compounds may be administered in a pharmaceutically effective amount. The amount of the compound actually administered may typically be determined in the light of the relevant circumstances, including the condition to be treated, the chosen route of administration, the actual compound administered, the age, weight, and response of the individual patient, the severity of the patient's symptoms, and the like.

The compounds and compositions described herein may be administered to a subject, preferably a mammal, more preferably a human, to treat and/or prevent disease by any suitable routes including, by way of illustration, oral, topical, rectal, transdermal, subcutaneous, intravenous, intramuscular, intranasal, and the like. Depending on the intended route of delivery, compounds may preferably be formulated as either oral, topical or injectable compositions.

Pharmaceutical compositions for oral administration may take the form of bulk liquid solutions or suspensions, or bulk powders. More commonly, however, such compositions may be presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid composition or pills, tablets, capsules or the like in the case of solid compositions.

Liquid forms suitable for oral administration may include a suitable aqueous or non-aqueous vehicle with buffers, suspending or dispensing agents, colorants, flavors and the like. Sole forms may include, for example, any of the following ingredients, or compounds of a similar nature: a binder such as microcrystalline cellulose, gum tragacanth or gelatin; an excipient such as starch or lactose; a disintegrating agent such as alginic acid, primogel, or corn starch; a lubricant such as magnesium stearate; a glidant such as colloidal silicon dioxide a sweetening agent such as sucrose or saccharin; and/or a flavoring agent such as peppermint, methyl salicylate or orange flavoring.

Topical compositions may be typically formulated as a topical ointment or cream containing the active ingredient(s), generally in an amount ranging from about 0.01 to 20% by weight, preferably from about 0.1 to about 10% by weight, and more preferably from about 0.5 to about 15% by weight. When formulated as an ointment, the active ingredient(s) may typically be combined with either a paraffinic or water-miscible ointment base. Alternatively, the active ingredient(s) may be formulated in a cream with, for example, an oil-in-water cream base. Such topical formulations may generally include additional ingredients to enhance to dermal penetration or stability of the active ingredient(s) or the formulation. All such known topical formulations and ingredients are included herein.

Compounds may also be administered by a transdermal device. Accordingly, topical administration may be accomplished using a patch either of the reservoir or porous membrane type or a solid matrix variety.

Injectable compositions may be typically based upon injectable sterile saline or phosphate-buffered saline or other injectable carriers known in the art.

The above-described components for orally and topically administrable or injectable compositions are merely representative. Other materials as well as processing techniques and the like are set forth in Part 8 of Remington's Pharmaceutical Sciences 18th edition, 1990, Mack Publishing Company, Easton Pa., 18042, which is incorporated herein by reference.

The compounds of this invention may also be administered in sustained release forms or from sustained release drug delivery systems. A description of representative sustained release materials may be found in the incorporated materials in Remington's Pharmaceutical Sciences.

As will be understood, pharmaceutical compositions as described herein may include one or more pharmaceutically acceptable carriers, excipients, and/or diluents as described in, for example, Remington's Pharmaceutical Sciences which is herein incorporated by reference in its entirety.

Pharmaceutical compositions may be formulated into tablets, capsules, liquid, injectable formulations, or an ointment. The present subject-matter, however, is not limited to the following pharmaceutical compositions. For example, yet without wishing to be limiting in any way, compounds of Formula A may be dissolved in a buffered sterile saline injectable aqueous medium to an appropriate concentration of approximately 5 mg/mL, for example.

Also provided herein are kits which may simplify the administration of a pharmaceutically active agent to an animal. A typical kit may comprise a unit dosage form of a pharmaceutical composition or compound as described herein. In one embodiment, the unit dosage form may be a container (such as a vial, a pouch, a tube, a syringe, or the like), which may advantageously be sterile, containing a pharmaceutical composition as described herein. The kit may further comprise a label or printed instructions instructing the use of the pharmaceutically active agent to treat or prevent a condition. In another embodiment, the kit may comprise a unit dosage form of a pharmaceutical composition as described herein and a dropper, syringe, or other application for administering the pharmaceutical composition. Typically, components of the kit, for example, the unit dosage form and instructions, may be contained within a suitable packaging material.

In the experimental examples provided herein, it is shown that the cyclic plasmenylethanolamine with palmitic acid (16:0) substituted at sn-1 and docosahexaenoic acid (22:6) substituted at sn-2 (i.e. PPI-1040) is a bioavailable plasmalogen precursor in the Pex7 hypomorphic animal model of rhizomelic chondrodysplasia punctata. Accordingly, administration of compounds as described herein to the Pex7 hypomorphic animal model of rhizomelic chondrodysplasia punctata increased tissue concentrations of the target endogenous ethanolamine plasmalogen. These compounds were designed to bypass the plasmalogen biosynthesis pathway. Other plasmalogen precursors have been tested which at least partially bypass the peroxisomal biosynthesis steps (see FIG. 1), but with limited therapeutic success.

Without wishing to be bound by theory, it is believed that the compounds described herein may be capable of bypassing the peroxisomal ether lipid biosynthesis pathways, and may allow for restoration of plasmalogen levels in plasmalogen deficient subjects. Accordingly, compounds as described herein may be used to treat or prevent diseases associated with decreased levels of plasmalogens, including but not limited to peroxisomal biogenesis disorders such as Rhizomelic chondrodysplasia punctata and/or Zellweger spectrum disorders.

It is also observed herein that the vinyl-ether bond at sn-1 may be relatively stable in vivo; the cyclic ethanolamine head group of compounds of formula A may be hydrolyzed in vivo, resulting in the endogenous target ethanolamine plasmalogen; and that the fatty acid substituent at sn-2 may be able to undergo deacylation and reacylation to other fatty acids in vivo.

The compounds of Formula A described herein may be converted to the ethanolamine plasmalogen species in an animal model with impaired plasmalogen biosynthesis capacity. Evidence indicates that such compounds may be able to effectively elevate tissue levels in animals with impaired plasmalogen biosynthetic capacity to levels at or above levels found in animals with unimpaired plasmalogen biosynthesis capacity.

These results represent a significant improvement over the prior art regarding plasmalogen precursors. 1-alkyl, 2-hydroxy glycerols (chimyl, batyl, salachyl alcohols) and 1-alkyl, 2-acyl glycerols (i.e. PPI-1011) have been shown to modestly increase plasmalogen levels in plasmalogen deficient animal models, but involved long time courses and high dosages; further, despite such increased time and dosage, levels in tissues were still not elevated in the plasmalogen deficient animals to control levels.

As will be understood, methods, compounds, compositions, and kits are provided herein for use in elevating a plasmalogen level in a subject in need thereof. In Examples 1-3, a mouse model is treated with PPI-1040, the mouse model being a model of rhizomelic chondrodysplasia punctata (RCDP) as an example of a subject suffering from a plasmalogen deficiency as described herein. RCDP is but one example, and it will further be understood that reductions in plasmalogen levels have been reported in a number of conditions such as neurodegenerative diseases including Alzheimer's disease [59-62], Parkinson's disease [63,64], Schizophrenia [65], Down syndrome [66] and Gaucher disease [67]. Plasmalogen deficits in one or more of these diseases may be directly involved in disease onset and progression. Accordingly, it is hypothesized that therapeutic agents which augment plasmalogen levels in deficient individuals may be used for treating, preventing, and/or ameliorating such diseases. Studies performed herein, such as those described in Example 4 investigating long term potentiation (LTP) and plasticity in brain slices, support such a hypothesis.

Indeed, a number of models of Alzheimer's disease and Parkinson's disease have been generated, however they are either created using neurotoxins, with numerous potential off-target effects, or genetically inducing the expression of proteins known to accumulate over the course of the disease. This presents a major challenge as the available animal models for neurodegenerative disease do not recapitulate the plasmalogen deficiency phenotype, preventing them from being suitable models for testing the viability of plasmalogen augmentation. This also prevents a clear understanding of the functional consequences of plasmalogen precursor treatment in the central nervous system. To address this issue, it is contemplated herein that a genetically plasmalogen deficient model system (Pex7 hypomorphic/null model) may be used in lieu of a disease specific model to assess the functional consequence of normalizing plasmalogen levels. Thus, the experimental findings described in Examples 1-3 below, while being primarily concerned with RCDP, may be extended beyond RCDP to other diseases or conditions relating to plasmalogen deficiency. By way of example, the hyperactive phenotype of the Pex7 hypomorphic/null animal model supports the importance of plasmalogens in the normal functioning of the central nervous system. As described in Example 3, using this plasmalogen deficient animal model, studies described herein were able to demonstrate not only that normalization of plasmalogen levels was possible using an oral plasmalogen replacement therapy (PPI-1040), but that normalization of plasmalogen levels also normalized a CNS-based behavioral phenotype. This data supports that plasmalogen augmentation may represent a treatment option in neurodegenerative diseases demonstrating plasmalogen deficiencies, such as (but not limited to) Alzheimer's and/or Parkinson's.

In certain embodiments, there is provided herein a method of increasing long term potentiation (LTP) between neurons, said method comprising:
 treating the neurons with a pharmaceutically effective amount of at least one cyclic plasmenylethanolamine having formula A:

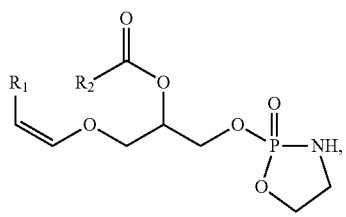

(A)

or a pharmaceutically acceptable salt or solvate thereof,
 wherein $R_1$ and $R_2$ are each, independently, a saturated, unsaturated, or polyunsaturated, optionally substituted hydrocarbon group.

In still another embodiment, there is provided herein a method of increasing long term potentiation (LTP) in a subject in need thereof, said method comprising:
 administering to said subject at least one cyclic plasmenylethanolamine having formula A:

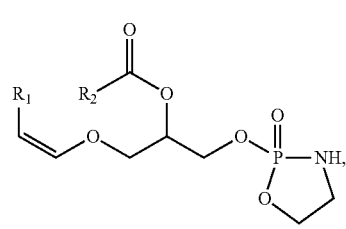

(A)

or a pharmaceutically acceptable salt or solvate thereof,
 wherein $R_1$ and $R_2$ are each, independently, a saturated, unsaturated, or polyunsaturated, optionally substituted, hydrocarbon group.

In still another embodiment, there is provided herein a method of treating or preventing Alzheimer's disease or Parkinson's disease in a subject in need thereof, said method comprising:
 administering to said subject at least one cyclic plasmenylethanolamine having formula A:

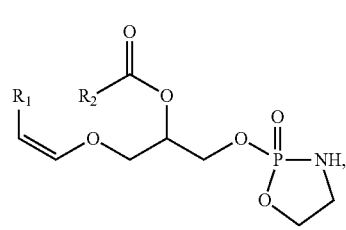

(A)

or a pharmaceutically acceptable salt or solvate thereof,
 wherein $R_1$ and $R_2$ are each, independently, a saturated, unsaturated, or polyunsaturated, optionally substituted hydrocarbon group.

In yet another embodiment, there is provided herein a method of treating or preventing a plasmalogen deficient neurodegenerative disease in a subject in need thereof, said method comprising:
 administering to said subject at least one cyclic plasmenylethanolamine having formula A:

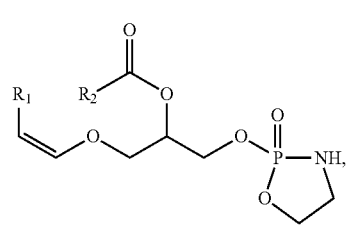

(A)

or a pharmaceutically acceptable salt or solvate thereof,
 wherein $R_1$ and $R_2$ are each, independently, a saturated, unsaturated, or polyunsaturated, optionally substituted hydrocarbon group.

In certain embodiments, the plasmalogen deficient neurodegenerative disease may be Alzheimer's disease or Parkinson's disease.

The following examples are provided for illustrative purposes intended for the person of skill in the art, and are not intended to be limiting in any way.

EXAMPLES

Animal Studies

Example 1: 2 Week Comparison of Plasmalogen Precursor

Pex7 homozygous hypomorphic animals (Pex7$^{neo/neo}$) were used as a model of rhizomelic chondrodysplasia punctata (RCDP). Mice were dosed with either PPI-1011 or PPI-1040 at equimolar concentrations of 100 mg/Kg and 89.7 mg/Kg respectively. PPI-1011 was formulated in Neobee M-5, at a concentration of 12.5 mg/mL and stored at −20° C. until the first treatment day after which point the remaining formulation was stored at 4° C. Oral gavage volumes were adjusted by mouse weight to ensure a 100 mg/kg dose. PPI-1040 was stored in a sealed ampoule in solution with dichloromethane under argon gas until immediately before use. At time of treatment the ampoule was opened and dichloromethane was evaporated off under nitrogen gas for 10 minutes. Neobee M-5 was then added and the solution and vortexed to generate a 22.4 mg/mL formulation. Animals were dosed via intraperitoneal injections with doses adjusted by weight to ensure an 89.7 mg/Kg dose to each animal. Animals were sacrificed 24 hours after the ninth treatment (week 1-Monday to Friday and week 2-Monday to Thursday). Blood samples were collected in EDTA tubes and then spun down in a clinical centrifuge. Plasma samples were stored at −80° C. until thawed for analysis. Tissue samples were harvested and flash frozen in liquid nitrogen and then stored at −80° C. All tissue samples were homogenized using liquid nitrogen, generating a fine powder.

Plasma aliquots of 20 μL were analyzed, while tissues were aliquoted with anti-static polypropylene disposable milligram scoops prior to analysis. Water (200 μL) was added and samples were ice bath sonicated for 30 mins prior to the addition of 600 μL of ethyl acetate. Samples were mixed at 2000 rpm for 15 mins followed by a 10 min centrifugation at 3500 rpm. Tissue samples were diluted into an ethyl acetate (1:4) containing labeled internal standards [$^{13}$C-PlsEtn (C$_{37}$$^{13}$C$_6$H$_{74}$NO$_7$P) and $^{13}$C-PtdEtn (C$_{24}$$^{13}$C$_{19}$H$_{74}$NO$_8$P)]. Water (80 μL) was added and samples were again stirred at 2000 rpm for 15 mins followed by a 2 min centrifugation at 3500 rpm. High-throughput analysis method was based on multiple reaction monitoring of one parent/fragment transition for the ion pairs, performed using liquid chromatography-mass spectrometry.

Figure 2:
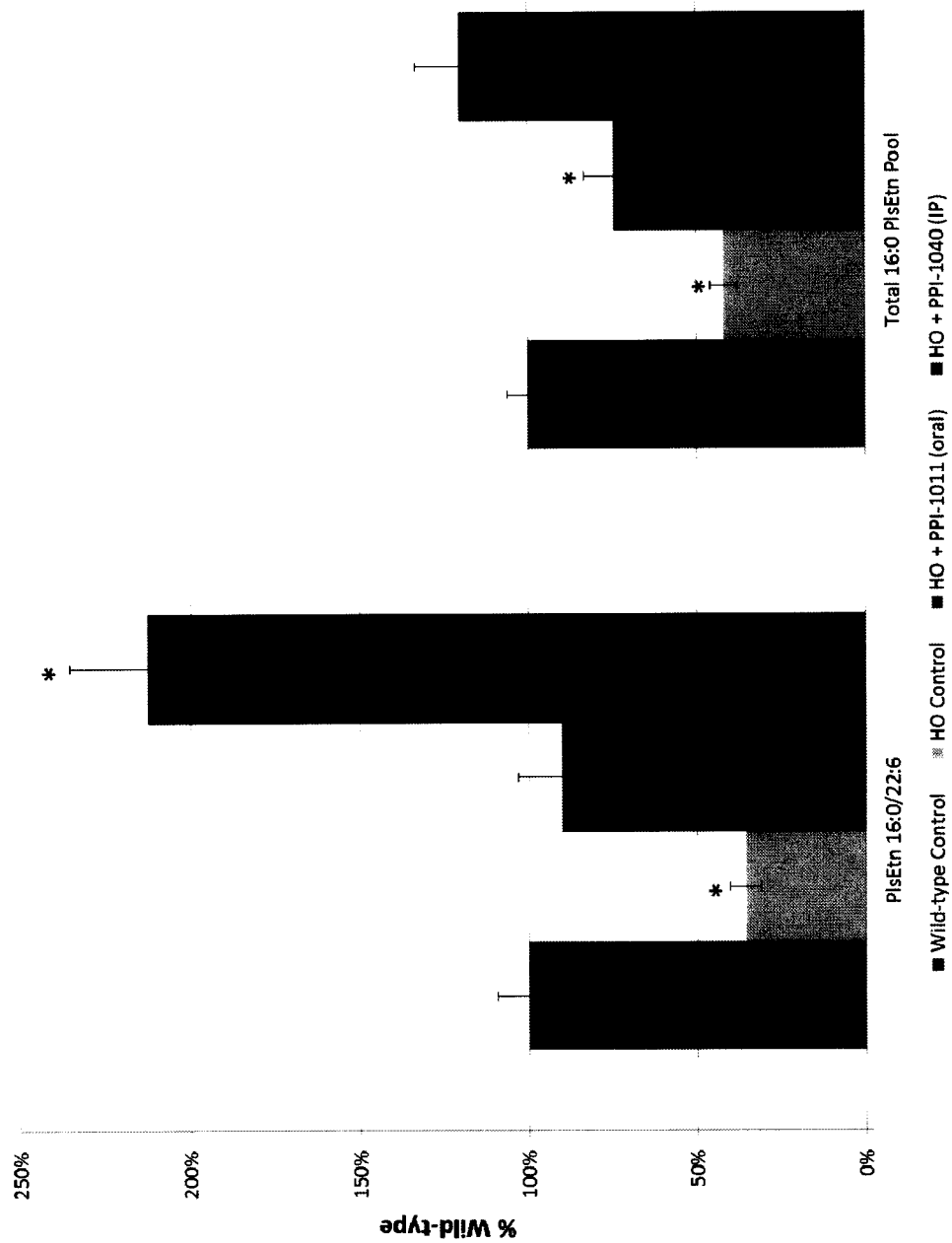
FIG. 2 shows plasmalogen augmentation in plasma, comparing control and Pex7 hypomorphic (HO) mice treated for 2 weeks with either PPI-1011 (oral) or PPI-1040 (intraperitoneal). Target plasmalogen of both therapeutics is 16:0/22:6 ethanolamine plasmalogen (PlsEtn). The sum of all 16:0 plasmalogen species is represented in the total 16:0 PlsEtn pool. Data is presented as mean±SEM n=3-6, *p<0.05 vs wild-type control.
Figure 3:
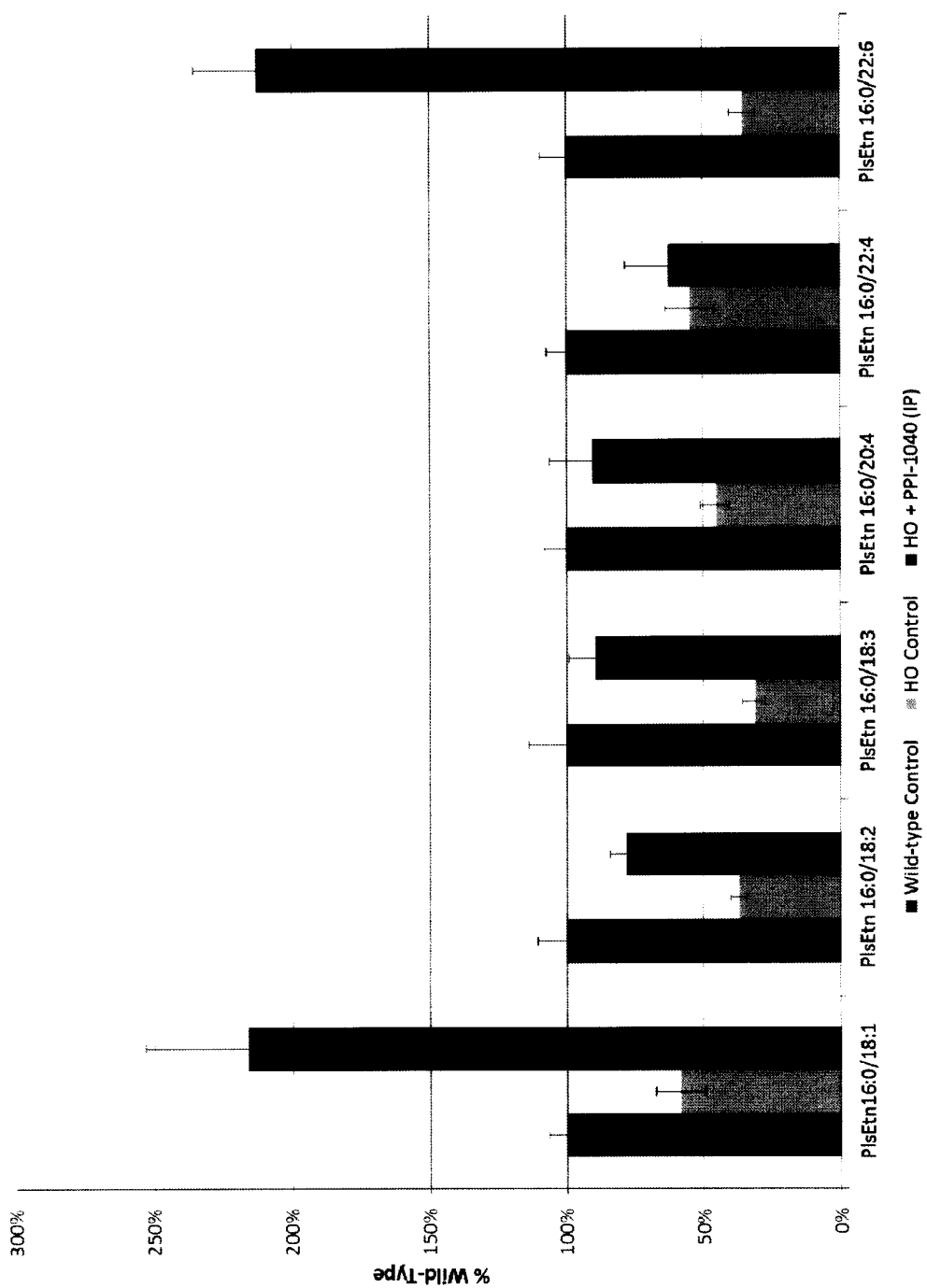
FIG. 3 shows re-organization at the sn-2 position following plasmalogen (PlsEtn) augmentation using PPI-1040 (intraperitoneal) in the plasma of Pex7 hypomorphic (HO) mice treated for 2 weeks. Data is presented as mean±SEM n=3-6, *p<0.05 vs wild-type control.

As seen in FIG. 2, treatment with PPI-1040 increased the levels of the target plasmalogen (16:0/22:6) in the plasma to a level 2× above control. This augmentation surpassed the increase observed from treatment with an equimolar dose of PPI-1011. Additionally, both precursors underwent remodeling at sn-2 by a deacylation/reacylation reaction, resulting in augmentation of numerous plasmalogen species with a palmitic acid substitution at sn-1 (FIG. 3), however only PPI-1040 augmented the total 16:0 plasmalogen to control levels (FIG. 2).

Figure 4:
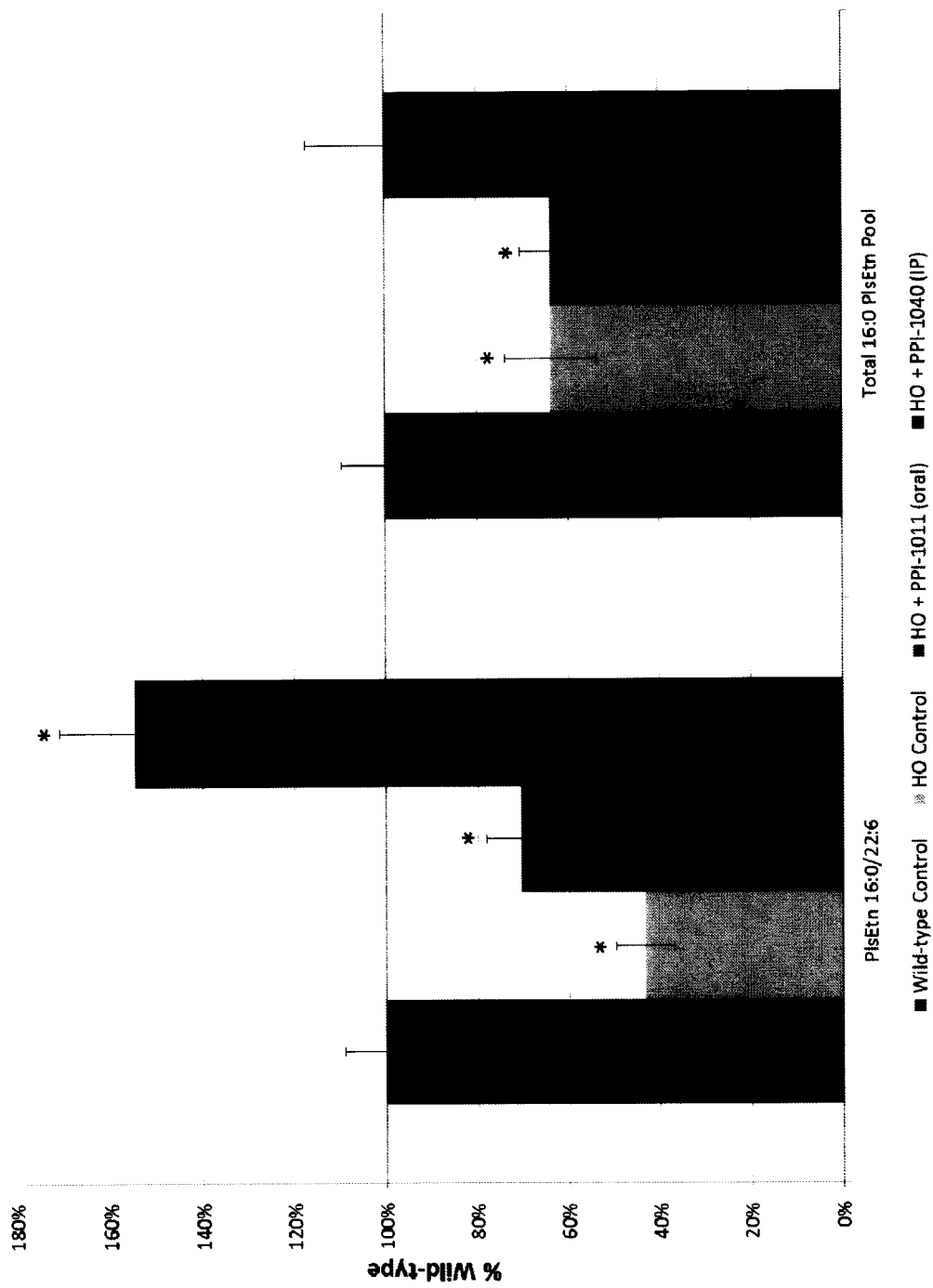
FIG. 4 shows plasmalogen augmentation in the liver, comparing control and Pex7 hypomorphic (HO) mice treated for 2 weeks with either PPI-1011 (oral) or PPI-1040 (intraperitoneal). Target plasmalogen of both therapeutics is 16:0/22:6 ethanolamine plasmalogen (PlsEtn). The sum of all 16:0 plasmalogen species is represented in the total 16:0 PlsEtn pool. Data is presented as mean±SEM n=4-6, *p<0.05 vs wild-type control.

Analysis of the liver tissue (FIG. 4) clearly illustrated that PPI-1040 treatment augmented the target plasmalogen levels in the plasmalogen deficient animals to levels above control within the 2 weeks of treatment. Contrary to the plasma results, PPI-1011 treatment was unable to augment levels to control levels. Further, PPI-1040 augmented the 16:0 plasmalogen pool in the liver to control levels, while no increase in this pool was observed following PPI-1011 treatment.

These results indicate that under the conditions tested PPI-1040 is bioavailable in the mouse and is converted to the endogenous ethanolamine plasmalogen in vivo. They also demonstrate the ability of PPI-1040 to augment plasmalogen levels in the tissue of plasmalogen deficient animals.

Example 2: Sub-Chronic Dosing with PPI-1040

Pex7 homozygous hypomorphic animals)(Pex7$^{neo/neo}$) were used as a model of rhizomelic chondrodysplasia punctata to further test the ability of PPI-1040 to augment plasmalogen levels in a deficient system, following 9 weeks of sub-chronic dosing. PPI-1040 was stored in a sealed ampoule in solution with dichloromethane under argon gas until immediately before use. At time of treatment the ampoule was opened and dichloromethane was evaporated off under nitrogen gas for 10 minutes. Neobee M-5 was then added and the solution vortexed to generate a 22.4 mg/mL formulation. Animals were dosed via intraperitoneal injections with doses adjusted by weight to ensure an 89.7 mg/Kg dose to each animal. Animals were sacrificed following 9 weeks of treatment with 3 doses administered per week (Monday, Wednesday and Friday). Blood samples were collected in EDTA tubes and then spun down in a clinical centrifuge. Plasma samples were stored at −80° C. until thawed for analysis. Tissue samples were harvested and flash frozen in liquid nitrogen and then stored at −80° C. All tissue samples were homogenized using liquid nitrogen, generating a fine powder. Extraction and plasmalogen analysis by LC-MS/MS was carried out as described above.

Figure 5:
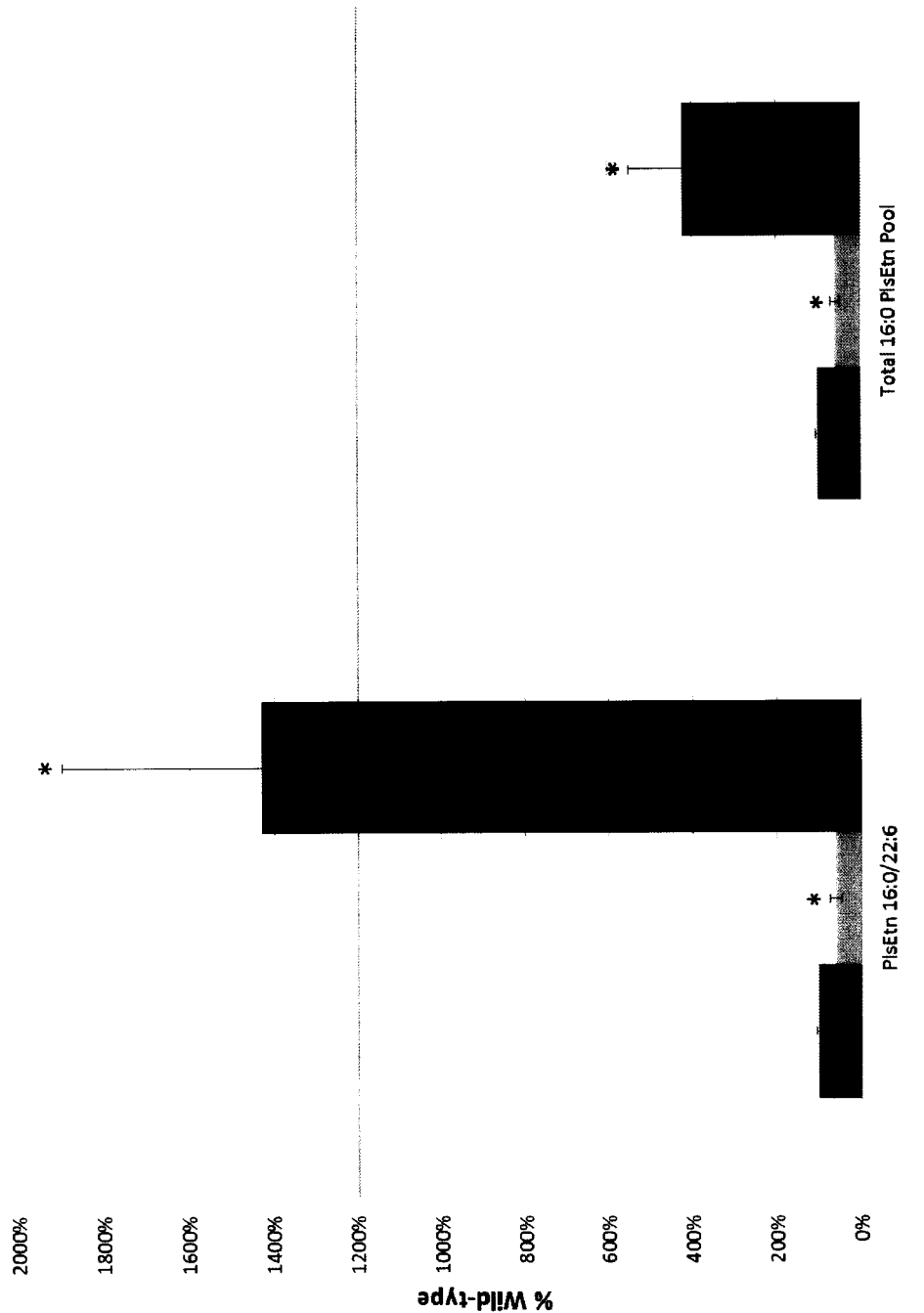
FIG. 5 shows plasmalogen augmentation in plasma, following 9 weeks of intraperitoneal PPI-1040 treatment (3 doses per week). Target plasmalogen of PPI-1040 treatment is 16:0/22:6 ethanolamine plasmalogen (PlsEtn). The sum of all 16:0 plasmalogen species is represented in the total 16:0 PlsEtn pool. Data is presented as mean±SEM n=3-6, *p<0.05 vs wild-type control.

The results demonstrated the ability of PPI-1040 to augment tissue and plasma plasmalogen levels in a model of plasmalogen deficiency. Plasmalogen levels of the target 16:0/22:6 ethanolamine plasmalogen in serum were elevated to levels significantly higher than control (FIG. 5). In addition, the 16:0 plasmalogen pool was also elevated to levels significantly above control.

Figure 6:
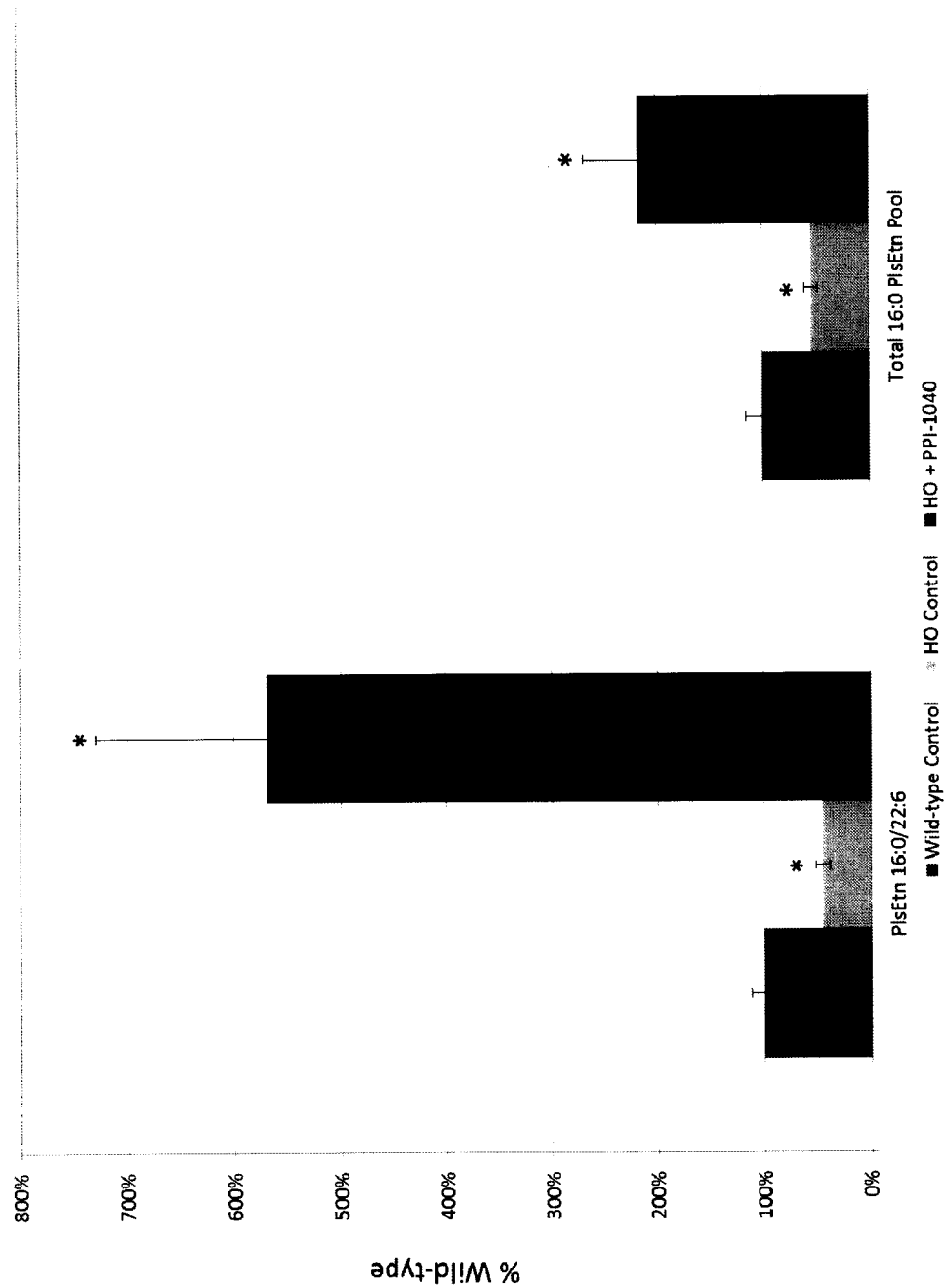
FIG. 6 shows plasmalogen augmentation in the liver, following 9 weeks of intraperitoneal PPI-1040 treatment (3 doses per week). Target plasmalogen of PPI-1040 treatment is 16:0/22:6 ethanolamine plasmalogen (PlsEtn). The sum of all 16:0 plasmalogen species is represented in the total 16:0 PlsEtn pool. Data is presented as mean±SEM n=4-6, *p<0.05 vs wild-type control.

Liver levels of the target plasmalogen (16:0/22:6) and the total 16:0 plasmalogen pool were both elevated to above control levels following 9 weeks of PPI-1040 treatment (FIG. 6).

Figure 7:
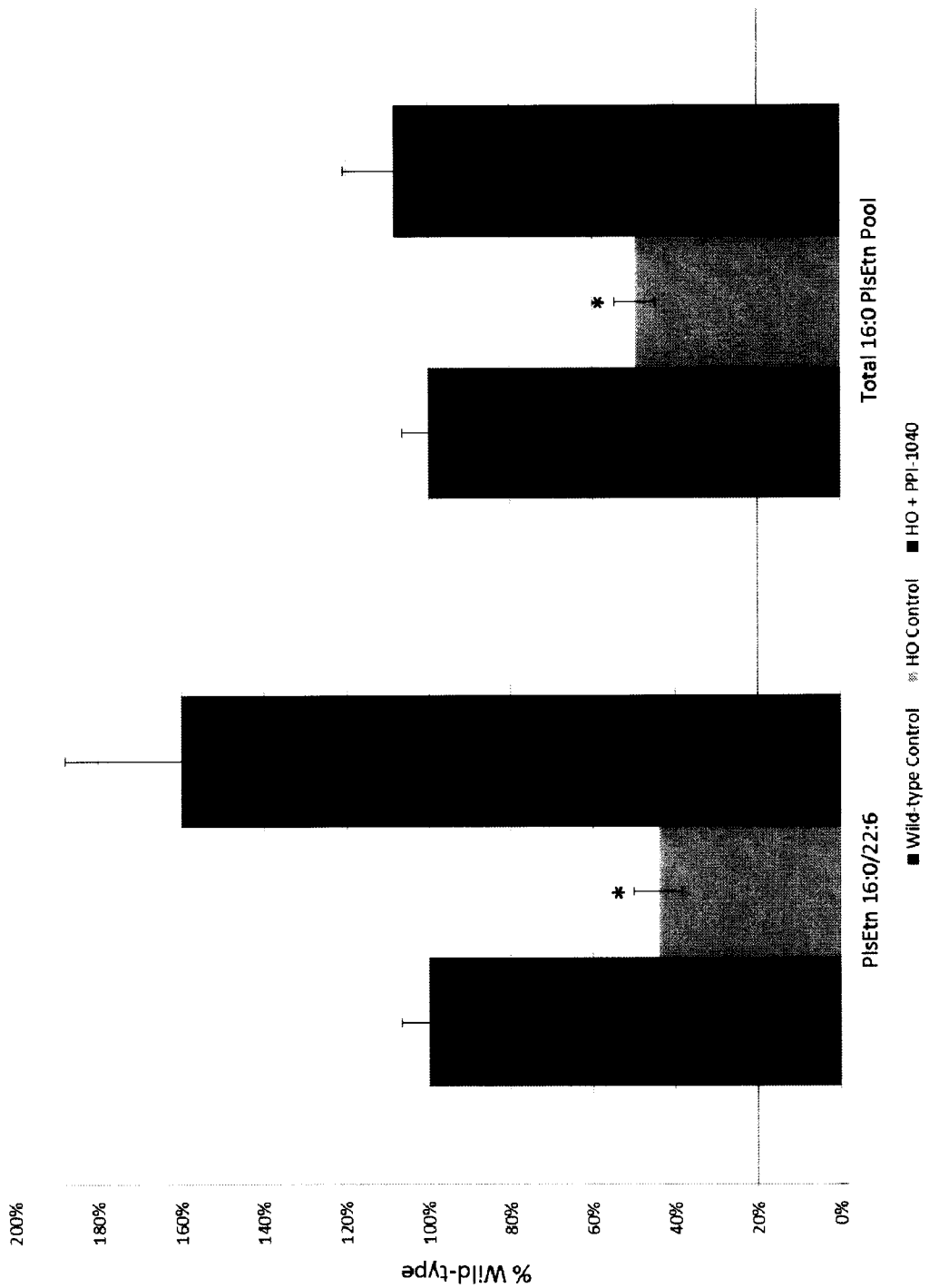
FIG. 7 shows plasmalogen augmentation in the lung, following 9 weeks of intraperitoneal PPI-1040 treatment (3 doses per week). Target plasmalogen of PPI-1040 treatment is 16:0/22:6 ethanolamine plasmalogen (PlsEtn). The sum of all 16:0 plasmalogen species is represented in the total 16:0 PlsEtn pool. Data is presented as mean±SEM n=4-6, *p<0.05 vs wild-type control.

Lung levels of the target plasmalogen (16:0/22:6) and the total 16:0 plasmalogen pool were both elevated to control levels following 9 weeks of PPI-1040 treatment (FIG. 7).

These results indicate the ability of PPI-1040 to effectively augment plasmalogen levels within the tissue of an animal model of rhizomelic chondrodysplasia punctate under the conditions tested.

The ability to augment lung plasmalogen levels in a plasmalogen deficient animal model may be of particular interest in certain embodiments, due to the observation that lung function is negatively impacted in patients with rhizomelic chondrodyplasia punctata either by frequent respiratory infections or chronic reactive airway disease [17,22]. In fact, the majority of deaths in RCDP patients (80%) are secondary to respiratory compromise [1].

Statistical analysis of the data was performed using Microsoft™ Office Excel 2010. Student t-tests were used to analyze the differences between treatment and controls.

Example 3: Oral Bioavailability of PPI-1040, and Restoration of Plasmalogen Levels and Reduction in Hyperactivity in a Pex7 Hypomorphic Mouse Model of RCDP1

As discussed herein, rhizomelic chondrodysplasia punctata (RCDP) is a devastating rare genetic disorder caused by mutations in peroxisomal genes essential for plasmalogen biosynthesis. Plasmalogens are a class of glycerophospholipids characterized by a vinyl-ether linked fatty alcohol at the sn-1 position. The vinyl-ether bond gives plasmalogens unique physiochemical properties such that they are obligate to normal membrane-mediated functions such as vesicular transport, membrane protein function and free radical scavenging. In the following studies, the oral bioavailability of a cyclic phosphoethanolamine vinyl-ether plasmalogen precursor intermediate, PPI-1040, was studied to investigate its ability to augment plasmalogen levels and normalize the behavioral phenotype in the Pex7 hypomorphic model of RCDP1.

As discussed in detail below, oral bioavailability of PPI-1040 was confirmed following treatment of control animals with a $C^{13}$-labelled version of the molecule. In addition, PPI-1040 normalized plasmalogen levels in the plasma and increased target plasmalogen levels to varying degrees in peripheral organs including the liver, small intestine and skeletal muscle of the Pex7 hypomorphic mouse. Although augmentation was not observed in cortical brain tissue, PPI-1040 treated mice showed a significant improvement ($p<0.05$) in the hyperactivity phenotype typical of the model, and a strong correlation between behavior and plasma plasmalogen levels was observed ($R_{2=0.37}$).

The present studies indicate that PPI-1040 may represent an interesting therapeutic option for augmenting plasmalogen levels in deficient individuals, including those with RCDP. The behavioral normalization observed following treatment supports that normalizing plasmalogen levels may result in functional improvements in vivo in these studies. RCDP is a class of genetic disorders with a prevalence estimated at less than 1 per 100,000 [23]. RCDP is clinically characterized by skeletal dysplasia, congenital cataracts, and profound growth and developmental delays. The skeletal dysplasia involves the proximal shortening of the long bones (rhizomelia) and abnormal, premature or delayed mineralization at the growth plates (chondrodysplasia punctata) which results in limited mobility of joints. Dramatically reduced life expectancy is common to RCDP patients; however survival varies widely with severity of the symptoms. Of the individuals who survive past the first month of life only 50% will survive beyond 5 years of age and nearly all succumb to the disease prior to adolescence. The vast majority of these deaths (80%) have been reported as secondary to respiratory problems [24]. Absent or severely decreased levels of ethanolamine plasmalogens (PlsEtn) is hallmark to all RCDP cases. There are 5 reported subtypes of RCDP, all have indistinguishable clinical features but result from mutations in different genes; Pex7 (RCDP1) [12-14], GNPAT (RCDP2) [15],AGPS (RCDP3) [16], FAR1 (RCDP4) (Buchert, Tawamie, et al., 2014, The American Journal of Human Genetics, 95, 602-610) and Pex5 (RCDP5)(Baroy, Koster, et al., 2015, Human Molecular Genetics, 24(20):5845-5854). GNPAT and AGPS are enzymes involved in the biosynthesis of plasmalogens, FAR1 is involved in the biosynthesis of the fatty alcohol precursor of plasmalogen synthesis and Pex7 and Pex5 are involved in the biosynthesis of peroxisomes. The 5 types of RCDP have indistinguishable phenotypes, and in all cases there is a direct correlation between phenotypic severity and residual plasmalogen levels [30,31].

Plasmalogens are a class of glycerophospholipids, characterized by a vinyl ether bond at the sn-1 position. Biosynthesis begins in the peroxisome by a series of non-redundant peroxisomal specific enzymes that create the ether bond which is reduced to the vinyl ether within the endoplasmic reticulum (ER). Plasmalogens are essential components of lipid membranes where they have been shown to play roles in vesicular transport, membrane protein activity and have antioxidant properties (reviewed [32]). Reductions in plasmalogen levels have also been reported in other neurodegenerative diseases including Alzheimer's disease [33-36], Parkinson's disease [37,38], Schizophrenia [39], Down syndrome [40] and Gaucher disease [41].

A number of Pex7 mutant mouse models have been developed to characterize the effects of plasmalogen deficiency and test potential therapeutic agents for RCDP [42-45]. The recently generated Pex7 hypomorphic/null mouse was utilized, which displays severe impairment of plasmalogen synthesis resulting in decreased growth and increased activity.

Plasmalogen precursors including batyl alcohol and the alkyl-glycerol PPI-1011 have been tested in other Pex7 mutant animals with modest results. Batyl alcohol (1-O-octadecyl-rac glycerol) is a C18:0 alkylglycerol, the presence of the ether bond allows it to bypass the peroxisomal-specific metabolic reactions required for plasmalogen synthesis. Treatment of Pex7 hypomorphic animals with 50 mg/kg/day for 2 months resulted in a partial increase in plasmalogen content in red blood cells but was not associated with clinical improvement [43]. A separate study supplemented Pex7 null animals with very high doses of batyl alcohol (over 3000 mg/kg) and found augmentation of plasmalogen levels in erythrocytes and peripheral tissues but very limited increases in brain and nervous system tissues [44]. These studies demonstrate the ability of therapeutic interventions to elevate plasmalogen levels, but faced difficulties due to the high doses and long treatment courses required to induce these changes.

Figure 8:
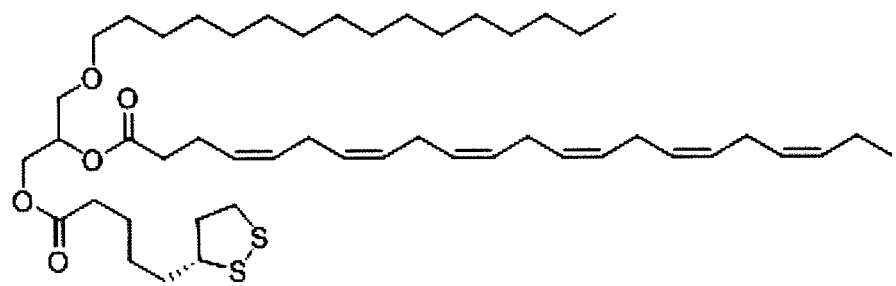
FIG. 8 shows chemical structures of plasmalogen precursors designed to augment plasmalogen levels in vivo. Stars denote the locations of $^{13}C$ molecules in the labelled compound.
Figure 8:
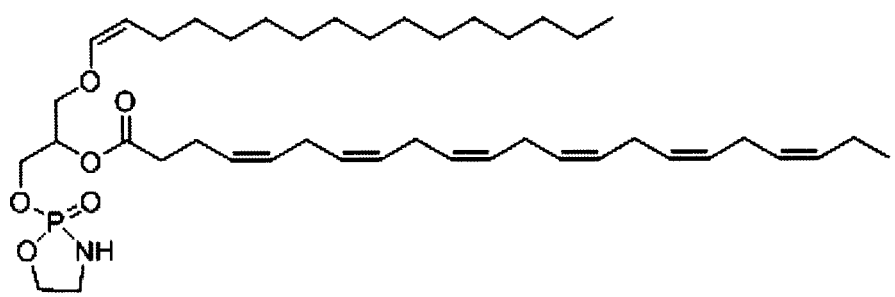
Figure 8:
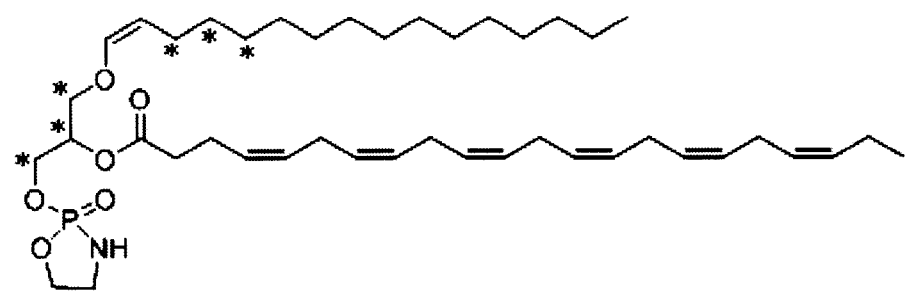

As discussed above, PPI-1011 is an alkyl-diacyl plasmalogen precursor, composed of palmitic acid, DHA and lipoic acid at sn-1, sn-2 and sn-3, respectively (FIG. 8). It has been shown to be orally bioavailable and capable of augmenting plasma and tissue PlsEtn levels in healthy animals [45,46]. Pex7 hypomorphic mice treated with a $^{13}$C-labeled version of PPI-1011 demonstrated that labeled plasmalogen wwas incorporated into peripheral tissues, as well as the neocortex and eye [45]. Incorporation into the nervous system tissue was low, suggesting a slower turnover rate of plasmalogen than in peripheral tissue. While these results were encouraging incorporation was lower than desired. This data taken together with the historical batyl alcohol results suggested a potential issue with the ability of RCDP animals to effectively metabolize these oral precursors into the intact plasmalogen species. Effects of severe plasmalogen deficiency on the structure and function of the ER have been reported [47,48], which is required to convert these precursor into the final plasmalogen species.

PPI-1040, on the other hand, is a direct plasmalogen precursor designed negating the requirement for enzymatic metabolism in vivo. PPI-1040 contains the vinyl-ether group at the sn-1 and a cyclic phosphoethanolamine group as the sn-3 constituent (FIG. 8). Upon exposure to an aqueous environment such as during circulation or in the stomach, the ring structure opens resulting in a fully intact 16:0/22:6 ethanolamine plasmalogen, indistinguishable from the endogenous species. The following studies demonstrate the stability, oral bioavailability and functional effects of treatment with PPI-1040.

Methods

Drugs:

PPI-1011, PPI-1040 and PPI-1050 were formulated in Neobee M-5 (Stepan Liquid Nutrition) with 0.1% thioglycerol (99%, Sigma) at a concentration of 10 mg/mL or 25 mg/kg (PPI-1050). PPI-1011 was stored at −4° C., while PPI-1040 and PPI-1050 were stored at −80° C. due to reduced stability. PPI-1050 is a $^{13}$C-labelled version of PPI-1040, with $^{13}$C labelling at the positioned indicated with a "*" in FIG. 8. Drug formulations were allowed to equilibrate to room temperature before treatment. Oral gavage volumes were adjusted by mouse weight to ensure the indicated mg/kg dose.

In Vitro Acid Stability:

To test the ability of the vinyl ether in PPI-1040 to withstand the acidic nature of the stomach the compound was exposed to a range of acid strengths (pH 1-5). The stability of the vinyl bond was tested by exposing PPI-1040 (formulated as indicated above) to a pH range from 1-5. The pH solutions were made by serial 10-fold dilutions of 1M HCL in HPLC grade water until pH 4 is reached. Pure HPLC grade water was used as the control solution. The final dilution was completed by added a 20 µl aliquot to 200 µl of the PPI-1040 formulation resulting in a pH range from 1-5 (each condition was tested in triplicate). The mixture was vortexed at room temperature for one hour. Following the one hour incubation each solution was re-suspended in ethyl acetate to obtain 10 µl/ml solution which was analyzed using flow injection tandem mass spectrometry (FI-MS/MS) on a API4000™ mass spectrometer (Applied Biosystems) coupled with Agilent 1100 HPLC pump and auto sampler.

Oral Bioavailability Study:

A $^{13}$C-labeled version of PPI-1040, called PPI-1050, was generated to evaluate the ability of the intact compound to cross the gut boundary and enter the bloodstream intact. PPI-1050 contains carbon-13 labels on the three glycerol carbons and 3 carbons of the sn-1 palmitic acid. Wild-type C57/Bl6 mice were treated with a single oral dose of 100 mg/kg PPI-1050 (formulated in Neobee-M5 with 0.1% thioglycerol) or vehicle. Animals were then sacrificed and blood harvested by cardiac puncture at 1, 3 and 6 hours post-treatment (n=3). Serum was then analyzed for presence of incorporation of the label into glycerolipids. Serum extraction was performed on 20 µL aliquots in 1.4 ml Thermo matrix tubes. Lipids were extracted by adding HPLC grade water (50 µl) and ethyl acetate (500 µL) to each serum sample and then mixing at 1750 rpm for 1 hr followed by a 2 min centrifugation at 3500 rpm for phase separation. A 100 µL aliquot of the ethyl acetate layer was analyzed using FI-MS/MS on a API4000™ mass spectrometer (Applied Biosystems) coupled with Agilent 1100 HPLC pump and auto sampler. Each transition was scanned for 50 ms with a total acquisition time per sample of 2 min. ethyl acetate:methanol:water ratio of 80:15:5 at a flow rate of 600 µL/min was used as the mobile phase. The parent PlsEtn mass was determined by incorporating the intact number of 13C labels in the predicted parent together with the corresponding daughter ion (sn2 fatty acid loss) to obtain the quantitative MS/MS transition pair. To confirm the ethanolamine group remained intact upon absorption we also analyzed serum for the presence of labeled alkyl-acyl and vinyl-acyl glycerols using FI-MS/MS analysis in positive mode. All transitions measured can be found in Table 1 below.

TABLE 1

List of labelled glycerolipids measured.

| Lipid Type | Sn1 | Sn2 | Glycerol | MRM Transition |
|---|---|---|---|---|
| PlsEtn | 16:0 (L) | 22:6 | Labeled | 752.5/327.2 |
| PlsEtn | 16:0 (L) | 18:0 | Labeled | 708.6/283.3 |
| PlsEtn | 16:0 (L) | 18:1 | Labeled | 706.6/281.3 |
| PlsEtn | 16:0 (L) | 18:2 | Labeled | 704.5/279.2 |
| PlsEtn | 16:0 (L) | 18:3 | Labeled | 702.5/277.2 |
| PlsEtn | 16:0 (L) | 20:4 | Labeled | 728.5/303.2 |
| PlsEtn | 16:0 (L) | 20:5 | Labeled | 726.5/301.2 |
| PlsEtn | 16:0 (L) | 22:4 | Labeled | 756.6/331.3 |
| PlsEtn | 16:0 | 18:0 | Labeled | 705.6/283.3 |
| PlsEtn | 16:0 | 18:1 | Labeled | 703.5/281.3 |
| PlsEtn | 16:0 | 18:2 | Labeled | 701.5/279.2 |
| PlsEtn | 16:0 | 18:3 | Labeled | 699.5/277.2 |
| PlsEtn | 16:0 | 20:4 | Labeled | 725.5/303.2 |
| PlsEtn | 16:0 | 20:5 | Labeled | 723.5/301.2 |
| PlsEtn | 16:0 | 22:4 | Labeled | 753.6/331.3 |
| PlsEtn | 16:0 | 22:6 | Labeled | 749.5/327.2 |
| PlsEtn | 18:0 | 18:0 | Labeled | 733.6/283.3 |
| PlsEtn | 18:0 | 18:1 | Labeled | 731.6/281.3 |
| PlsEtn | 18:0 | 18:2 | Labeled | 729.5/279.2 |
| PlsEtn | 18:0 | 18:3 | Labeled | 727.5/277.2 |
| PlsEtn | 18:0 | 20:4 | Labeled | 753.6/303.2 |
| PlsEtn | 18:0 | 20:5 | Labeled | 751.5/301.2 |
| PlsEtn | 18:0 | 22:4 | Labeled | 781.6/331.3 |
| PlsEtn | 18:0 | 22:6 | Labeled | 777.6/327.2 |
| VAG | 16:0 (L) | 18:1 | Labeled | 585.6/242.3 |
| VAG | 16:0 (L) | 18:2 | Labeled | 583.5/242.3 |
| VAG | 16:0 (L) | 20:4 | Labeled | 607.5/242.3 |
| VAG | 16:0 (L) | 20:5 | Labeled | 605.5/242.3 |
| VAG | 16:0 (L) | 22:4 | Labeled | 635.7/242.3 |
| VAG | 16:0 (L) | 22:6 | Labeled | 631.5/242.3 |
| VAG | 16:0 | 18:1 | Labeled | 582.5/239.2 |
| VAG | 16:0 | 18:2 | Labeled | 580.5/239.2 |
| VAG | 16:0 | 20:4 | Labeled | 604.5/239.2 |
| VAG | 16:0 | 20:5 | Labeled | 602.5/239.2 |
| VAG | 16:0 | 22:4 | Labeled | 632.6/239.2 |
| VAG | 16:0 | 22:6 | Labeled | 628.5/239.2 |
| VAG | 16:0 | 18:1 | Unlabelled | 579.5/239.2 |
| VAG | 16:0 | 18:2 | Unlabelled | 577.5/239.2 |
| VAG | 16:0 | 20:4 | Unlabelled | 601.5/239.2 |
| VAG | 16:0 | 20:5 | Unlabelled | 599.5/239.2 |
| VAG | 16:0 | 22:4 | Unlabelled | 629.5/239.2 |
| VAG | 16:0 | 22:6 | Unlabelled | 625.5/239.2 |
| AAG | 16:0 (L) | 18:1 | Labeled | 587.6/244.3 |
| AAG | 16:0 (L) | 18:2 | Labeled | 585.5/244.3 |
| AAG | 16:0 (L) | 20:4 | Labeled | 609.5/244.3 |
| AAG | 16:0 (L) | 20:5 | Labeled | 607.5/244.3 |
| AAG | 16:0 (L) | 22:4 | Labeled | 637.7/244.3 |
| AAG | 16:0 (L) | 22:6 | Labeled | 633.5/244.3 |
| AAG | 16:0 | 18:1 | Labeled | 584.6/241.3 |
| AAG | 16:0 | 18:2 | Labeled | 582.5/241.3 |
| AAG | 16:0 | 20:4 | Labeled | 606.5/241.3 |
| AAG | 16:0 | 20:5 | Labeled | 604.5/241.3 |
| AAG | 16:0 | 22:4 | Labeled | 634.6/241.3 |
| AAG | 16:0 | 22:6 | Labeled | 630.5/241.3 |

Treatment of Pex7 hypomorph/null animals:

The Pex7 hypomorph/null model is a hypomorphic (B6; 129S6-Pex7$^{tm2.3Brav}$/s9) mouse model on a mixed background (C57BL/6NCrl and 129S6/SvEvTac). The hypomorphic allele in Pex7 hypomorph/null was generated by inserting an inverse neo cassette into intron 2 and lox P sites surrounding exon 3. The Pex7 null allele was generated using (B6.C-Tg(cmv-cre)1Cgn/J) mouse. The Pex7 hypomorph/null mouse model has 90% survival, 0.016-0.257% of wild type Pex7 mRNA levels and 20-30% plasmalogen levels Pex7 hypomoprh/null mice (3-4 months); and wild-type animals, males and females included in treatments and behavioral tests. Pex7 hypomorph/null mice were randomly assigned, after a baseline open field test, into 3 treatment groups: PPI-1040, PPI-1011, and vehicle controls, n=6 mice per group). PPI-1011 or PPI-1040 at 50 mg/kg was given by oral gavage 5 days per week (Monday-Friday) for 4 weeks. During the treatment period, animals were weighed weekly and observed for signs of distress. The open field test was performed at the end of treatment. To avoid selection bias, data analysis was performed only at the study end. Animals were sacrificed after a 24-hour post the last dose.

Tissues were harvested for LC/MSMS analysis.

Open Field Testing:

The open field test is a behavioral test used to evaluate the general locomotor activity, exploratory and anxiety-like behaviour of mice in response to a novel environment. The animal is placed inside a custom made square, gray acrylic box measuring 40×40×40 cm and allowed to move freely for 5 minutes while being recorded by an overhead camera (camera model). The footage was analyzed by an automated tracking system (Any-maze Video Tracking Software, Stoelting Co, Wood Dale, Ill., USA), for total distance traveled (meters) & activity (mobility in seconds) time. The total distance traveled is the total distance that animal traveled during the test and the activity measures the amount of time the animal was active during the test.

Plasma extraction was performed on 20 μL aliquots in 1.4 ml Thermo matrix tubes. Lipids were extracted by adding HPLC grade water (50 μl) and ethyl acetate containing labeled internal standard [$^{13}$C-PlsEtn ($C_{37}$$^{13}C_6H_{74}NO_7P$)] at 0.2 μg/mL (500 μL) to each plasma sample and then mixing at 1750 rpm for 1 hr followed by a 2 min centrifugation at 3500 rpm for phase separation.

A 100 μL aliquot of the ethyl acetate layer was analyzed using FI-MS/MS on a API4000™ mass spectrometer (Applied Biosystems) coupled with Agilent 1100 HPLC pump and auto sampler. Each transition was scanned for 50 ms with a total acquisition time per sample of 2 min. ethyl acetate:methanol:water ratio of 80:15:5 at a flow rate of 600 μL/min was used as the mobile phase. All standards and stable isotopes used were >95% pure and manufactured by Med-Life Discoveries LP. All the solvents used above were HPLC grade. All samples were analyzed in triplicate to control for any variation resulting from instrument variability. Stable isotope ratios for each analyte were calculated for all tissue and plasma samples (Table 2).

TABLE 2

List of phosphoethanolamine analytes measured.

| Analyte | Molecular Formula | MRM transition | Analyte | Molecular Formula | MRM transition |
|---|---|---|---|---|---|
| $^{13}$C-PtdEtn 16:0/22:6 | $C_{24}$$^{13}C_{19}H_{74}NO_8P$ | 781.5/327.2 | $^{13}$C-PlsEtn 16:0/22:6 | $C_{37}$$^{13}C_6H_{74}NO_7P$ | 752.5/327.2 |
| PtdEtn 16:0/18:0 | $C_{39}H_{78}NO_8P$ | 718.5/255.2 | PlsEtn 16:0/18:1 | $C_{39}H_{76}NO_7P$ | 700.5/281.2 |
| PtdEtn 16:0/18:1 | $C_{39}H_{76}NO_8P$ | 716.5/255.2 | PlsEtn 16:0/18:2 | $C_{39}H_{74}NO_7P$ | 698.5/279.2 |
| PtdEtn 16:0/18:2 | $C_{39}H_{74}NO_8P$ | 714.5/255.2 | PlsEtn 16:0/20:4 | $C_{41}H_{74}NO_7P$ | 722.5/303.2 |
| PtdEtn 16:0/18:3 | $C_{39}H_{72}NO_8P$ | 712.5/255.2 | PlsEtn 16:0/20:5 | $C_{41}H_{72}NO_7P$ | 720.5/301.2 |
| PtdEtn 16:0/20:4 | $C_{41}H_{74}NO_8P$ | 738.5/255.2 | PlsEtn 16:0/22:4 | $C_{43}H_{78}NO_7P$ | 750.5/331.2 |
| PtdEtn 16:0/20:5 | $C_{41}H_{72}NO_8P$ | 736.5/255.2 | PlsEtn 16:0/22:6 | $C_{43}H_{74}NO_7P$ | 746.5/327.2 |
| PtdEtn 16:0/22:4 | $C_{43}H_{78}NO_8P$ | 766.5/255.5 | PlsEtn 18:0/18:1 | $C_{41}H_{80}NO_7P$ | 728.5/281.2 |
| PtdEtn 16:0/22:6 | $C_{43}H_{74}NO_8P$ | 762.5/255.2 | PlsEtn 18:0/18:2 | $C_{41}H_{78}NO_7P$ | 726.5/279.2 |
| PtdEtn 16:0/24:6 | $C_{45}H_{78}NO_8P$ | 790.5/255.2 | PlsEtn 18:0/20:4 | $C_{43}H_{78}NO_7P$ | 750.6/303.2 |
| PtdEtn 18:0/18:1 | $C_{41}H_{80}NO_8P$ | 744.5/283.2 | PlsEtn 18:0/20:5 | $C_{43}H_{76}NO_7P$ | 748.5/301.3 |
| PtdEtn 18:0/18:2 | $C_{41}H_{78}NO_8P$ | 742.5/283.2 | PlsEtn 18:0/22:4 | $C_{45}H_{82}NO_7P$ | 778.5/331.2 |
| PtdEtn 18:0/20:4 | $C_{43}H_{78}NO_8P$ | 766.5/283.2 | PlsEtn 18:0/22:6 | $C_{45}H_{78}NO_7P$ | 774.5/327.2 |
| PtdEtn 18:0/20:5 | $C_{43}H_{76}NO_8P$ | 764.5/283.2 | | | |
| PtdEtn 18:0/22:4 | $C_{45}H_{82}NO_8P$ | 794.5/283.2 | | | |
| PtdEtn 18:0/22:6 | $C_{45}H_{78}NO_8P$ | 790.5/283.2 | | | |
| PtdEtn 18:0/24:6 | $C_{47}H_{82}NO_8P$ | 818.5/283.2 | | | |

Quantification of plasmalogens and metabolites in Pex7 hypomorphic tissue and plasma samples:

Tissue samples frozen by submersion in liquid nitrogen were homogenized using the Covaris Cryoprep resulting in a fine powder. The powder was then aliquoted using antistatic polypropylene disposable milligram scoops (TWD Tradewinds) resulting in 4-6 mg of tissue per 1.4 ml Thermo matrix tubes. Weights were recorded and metabolite levels were normalized per mg of tissue. HPLC grade water (50 μl) was added into each tube and samples were snap frozen in liquid nitrogen and then stored at −80° C. until extraction. On the day of the extraction, tissue samples were thawed to room temperate and sonicated for 15 mins in an ice bath before mixing at 2000 rpm for a 5 minute and then adding 600 μL of ethyl acetate. Lipids were extracted into ethyl acetate by mixing at 1750 rpm for 1 hr followed by a 10 min centrifugation at 3500 rpm to obtain a clear ethyl acetate layer. Tissue lipid extracts were diluted into an ethyl acetate stock (brain regions diluted 1:10, peripheral tissues 1:5) containing labeled internal standard [$^{13}$C-PlsEtn ($C_{37}$$^{13}C_6H_{74}NO_7P$)]. Water (40 μL) was added to the diluted extracts and samples were stirred at 1500 rpm for 1 hr followed by a 2 min centrifugation at 3500 rpm.

Statistical Analysis:

Data are presented as mean±SD. One-way analysis of variance (ANOVA) using a Tukey post-hoc test was used to analyze plasmalogen levels and behavioral data. Basic linear regression was used to compare plasmalogen levels to behavioral scores. A p-value less than 0.05 was considered statistically significant.

Results

Figure 9:
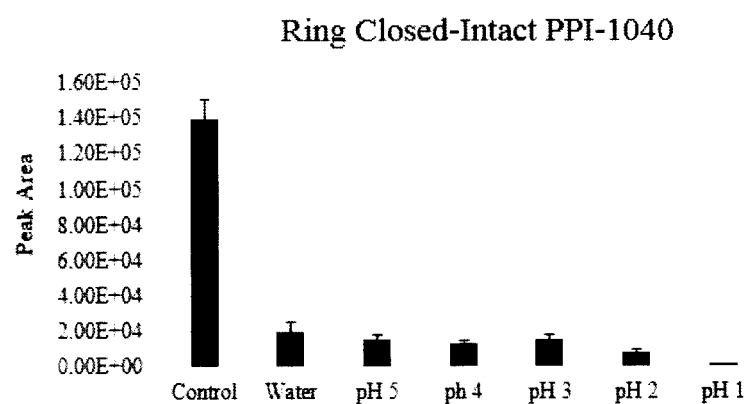
FIG. 9 shows stability of PPI-1040 under increasing acidic conditions to test the acid-lability of the vinyl-ether bond. A) Opening of the cyclic-ethanolamine group readily occurs upon exposure to water or acid resulting in minimal intact PPI-1040 being observed. B) Following opening of the ring the resulting 16:0/22:6 ethanolamine plasmalogen remains stable up to a pH of 2. C) Loss of the sn-1 ether group which would result from cleavage of the vinyl-ether bond is observed beginning at pH2 and by pH1 the molecule appears to be largely degraded. Mean±SD, n=3.
Figure 9:
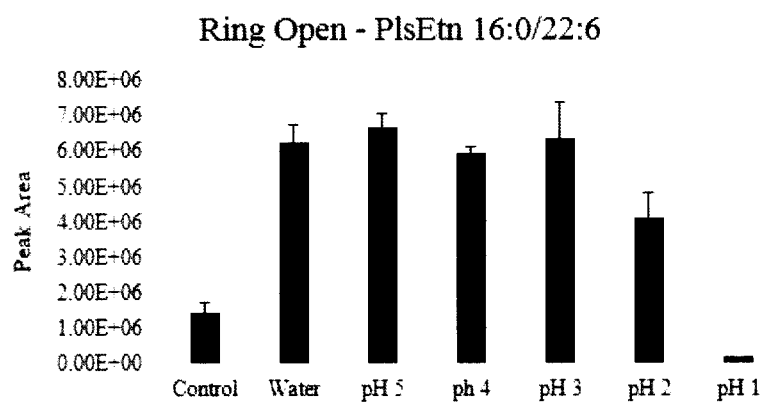
Figure 9:
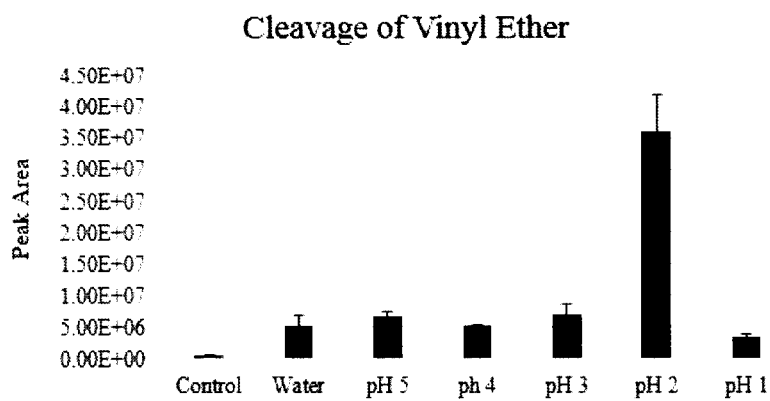

Acid Stability of PPI-1040:

To further investigate PPI-1040 as an oral therapy to augment plasmalogen levels, the acid stability of the vinyl ether bond under acidic conditions was studied. PPI-1040 was exposed to both aqueous (control) and acidic conditions (pH 1-5) for one hour to simulate the environment of the stomach. The cyclized ethanolamine group at the sn-3 position of PPI-1040 was shown to readily open upon exposure to an aqueous or acidic environment, with levels of the cyclized form being almost undetectable in all samples following incubation (FIG. 9A). The open ring version of PPI-1040 is identical to endogenous PlsEtn 16:0/22:6, and was stable up to pH 3 with a slight reduction observed at pH 2 and very little being detected at pH 1, suggesting degradation of the vinyl bond at low pH (FIG. 9B). By analyzing the level of open ring PPI-1040 which underwent cleavage of the sn-1 vinyl-ether bond it was confirmed that under control conditions and pH 3-5 there was minimal loss of the sn-1 group. However, cleavage of the vinyl group is prevalent beginning at pH 2 and by pH 1 there appears to be an overall degradation of the molecule (FIG. 9C).

Uptake of $^{13}$C-labeled PPI-1040:

Oral bioavailability was studied by dosing wild-type mice with a $^{13}$C-labeled version of PPI-1040 called PPI-1050, and evaluating serum for the intact labeled compound. In addition, the metabolism of the drug was traced by measuring PlsEtn with substituted sn-2 constituents. PPI-1040 with the closed ring intact was not detectable in any samples (data not shown), indicating that the ring spontaneously opened upon ingestion. A clear time-dependent increase was observed in the target $^{13}$C$_6$-labeled PlsEtn 16:0/22:6 (FIG. 9A). Remodeling of the sn-2 constituent has been reported to readily occur, and therefore $^{13}$C6-labeled PlsEtn with 16:0 at sn-1 and the five most commonly occurring sn-2 constituents were measured (FIG. 9B). All species mirrored the time-dependent increase seen with the target PlsEtn. To verify that the vinyl-ether bond was not hydrolyzed or subject to re-arrangement of the sn-1, the levels of the same PlsEtn species were measured but with a $^{13}$C$_3$-labeled which would be expected if the vinyl-ether broke and only the sn-1 palmitic or the glycerol remained labeled, but not both. No increases were observed in any of the species at any time point relative to vehicle controls, confirming the vinyl-ether bond remained intact. Finally, to confirm the sn-3 phosphoethanolamine group was not removed prior to absorption the presence of vinyl-acyl and alkyl-acyl 16:0/22:6 was tested for, neither of which was elevated relative to control. Together these data illustrate that PPI-1040 was orally bioavailable and crossed the gut lining intact, with only the expected sn-2 re-arrangement occurring.

Figure 10:
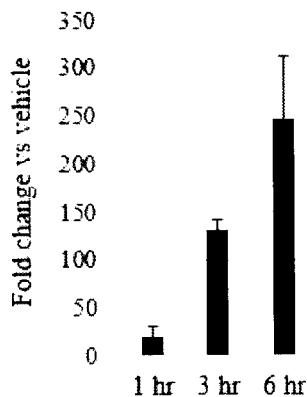
FIG. 10 shows incorporation of PPI-1050 in serum following a single oral treatment in wild-type animals. A) Target 16:0/22:6 plasmalogen representing the open cyclic-ethanolamine group of otherwise fully intact PPI-1050. B) Incorporation of the vinyl-ether sn-1 and glycerol backbone into the 16:0 plasmalogen pool following re-organization at the sn-2 location. Mean±SD, n=3.
Figure 10:
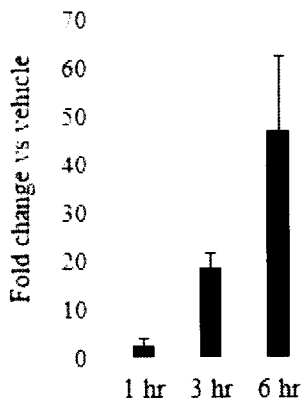
Figure 10:
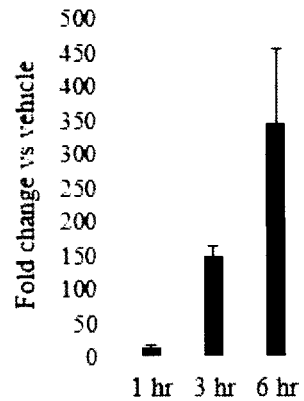
Figure 10:
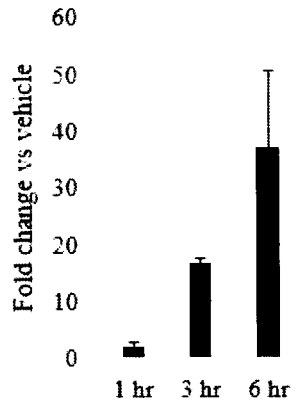
Figure 10:
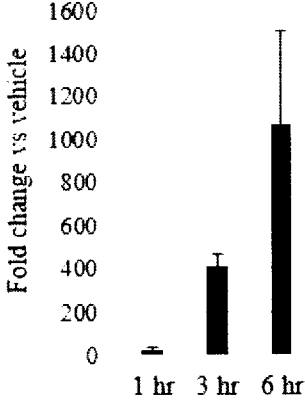
Figure 10:
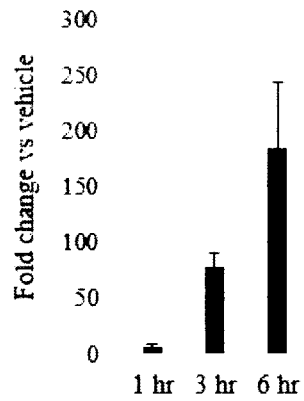
Figure 10:
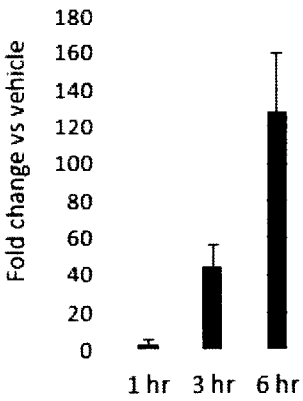

Augmentation of Plasmalogen Levels in PPI-1040 Treated Pex7 Hypomorph/Null Mice:

Following 4 weeks of oral administration of vehicle, PPI-1011 or PPI-1040, plasma and tissue levels were tested for plasmalogen levels. Pex7 hypomorphic/null animals had significantly decreased levels of all plasmalogens measured, averaging approximately 25% of wild-type control levels. Treatment with PPI-1011 at 50 mg/kg did not result in significant augmentation of any plasmalogen species measured. PPI-1040 treatment however was able to augment plasmalogen levels. In addition to normalizing the levels of the target 16:0/22:6 plasmalogen, re-organization at the sn-2 position occurred with increases in all measured 16:0 plasmalogens with the exception of 16:0/22:4, which represent a small proportion of the total 16:0 plasmalogen pool (FIG. 10). Plasmalogens containing 18:0 and 18:1 at sn-1 were also measured, but as anticipated no augmentation was observed in any of those species. In addition, samples were analyzed for levels of vinyl-acyl and alkyl-acyl glycerols, which would be expected to increase if the phosphoethanolamine group was removing. None of the alkyl-acyl or vinyl-acyl glycerol species were increased in treated animals.

A variety of peripheral tissues, as well as brain tissues, were also analyzed for plasmalogen levels. As seen in the plasma, PPI-1011 did not increase the levels of any plasmalogen species in any of the tissues tested (data not shown). PPI-1040 was able to augment tissues to varying degrees in peripheral tissues with augmentation observed in the liver, skeletal muscle and small intestine. In the liver the levels of all plasmalogen species (except 16:0/22:4) showed a trend towards increased levels, with the increases in 16:0/18:1, 16:0/18:2 and 16:0/22:6 species reaching statistical significance (FIG. 10A). Augmentation was also observed in skeletal muscle with the 16:0/20:5, 16:0/22:6 and total 16:0 plasmalogen pool levels statistically increased (FIG. 10B). Small intestine samples showed a high degree of inter-animal variation making interpretation difficult. The levels of the 16:0/20:5 species were below the level of quantitation and therefore are not presented. The levels of a number of species appear to trend toward augmentation, with 16:0/18:1 and 16:0/18:2 species reaching a statistically significant increase (FIG. 10C). As reported for the plasma, plasmalogens with 18:0 and 18:1 at sn-1 were not augmented. In contrast, lung and kidney did not display a clear augmentation in any plasmalogen species following treatment (FIG. 10D,E). Finally, cortical and cerebellum tissue were tested and did not show augmentation in PPI-1040 treated animals (FIG. 10F, G).

Figure 11:
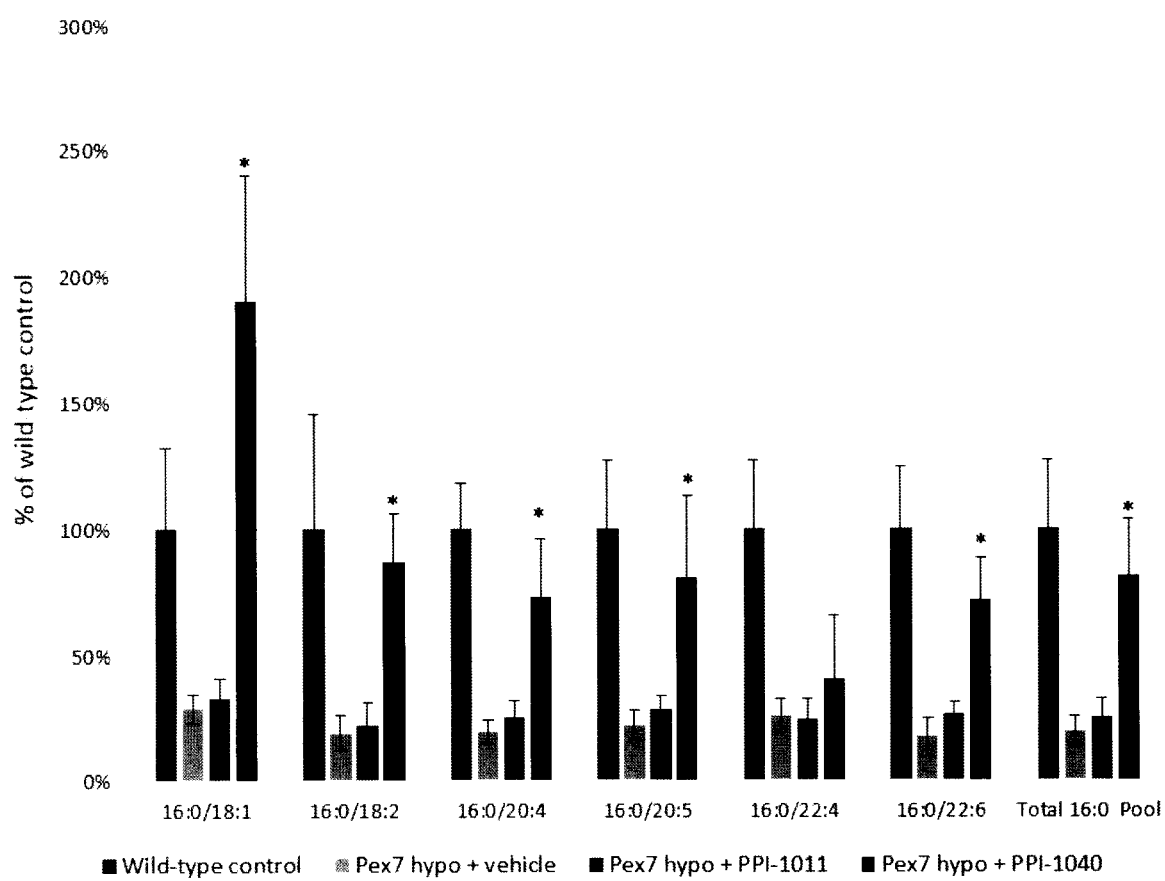
FIG. 11 shows plasmalogen levels in plasma from Pex7 hypomorphic/null mice treated with vehicle or PPI-1040. All plasmalogen species were significantly below baseline in the vehicle and PPI-1011. Mean±SD, n=4-6 *-p<0.05 vs vehicle. Moving from left to right in each set of 4 bars shows, in the following order, Wild-type control, Pex7 hypo+vehicle, Pex7 hypo+PPI-1011, Pex7 hypo+PPI-1040.

Behavioral Assessments of Pex7 Hypomorph/Null Mice:

Pex7 hypomorph/null mice were tracked within an open field to assess the level of activity as measured by total distance traveled (meters) and time active (seconds). Vehicle treated animals displayed a significant level of hyperactivity relative to wild-type controls as assessed by either measurement. Treatment with PPI-1040 resulted in normalization of the hyperactive phenotype as assessed by both time active and distance travelled (FIG. 11A). Representative tracking images for each treatment group are presented. In addition, plasma plasmalogen levels were shown to strongly correlate with behavioral phenotype. The plasma levels of the target 16:0/22:6 plasmalogen correlated with both distance traveled ($R^2$=0.36, F=7.93, p=0.014) and time active ($R^2$=0.54, F=16.37, p=0.0012) (FIG. 11C). Total 16:0 plasmalogen levels in the plasma allowed for an assessment of the total pool of plasmalogens augmented following treatment, and also correlated with both distance travelled ($R^2$=0.37, F=8.37, p=0.011) and time active ($R^2$=0.55, F=17.28, p=0.00096).

Figure 14:
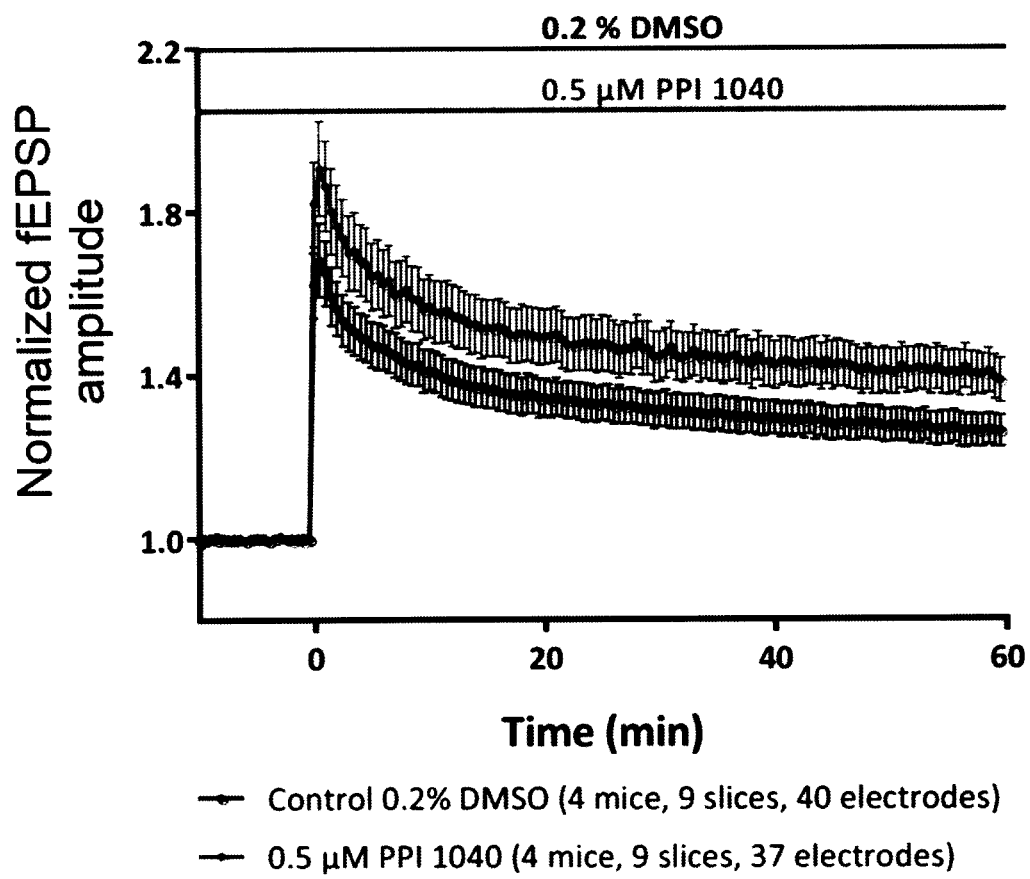
FIG. 14 shows results of Long Term Potentiation (LTP) performed on wild-type mouse hippocampal brain slices treated with either vehicle or PPI-1040. Blue (upper curve) indicates 0.5 μM PPI 1040 condition (4 mice, 9 slices, 37 electrodes); Black (lower curve) indicates control 0.2% DMSO condition (4 mice, 9 slices, 40 electrodes)

Discussion:

Based on the acid stability study and the $C^{13}$-labelled PPI-1050 oral treatment study it is clear that the vinyl-ether bond is stable in the acidic environment of the stomach, and is readily absorbed from the GI tract following oral administration. In addition, the $C^{13}$-labelled PPI-1050 data demonstrates that other than the desired opening of the cyclic phosphoethanolamine ring, the structure of the molecule is absorbed intact. Normalization of the plasmalogen levels in the plasma and increased plasmalogen levels, to varying degrees, in peripheral organs including the liver, small intestine and skeletal muscle of the Pex7 hypomorphic/null mice supports the hypothesis that augmenting plasmalogen levels in deficient individuals may be possible with PPI-1040 treatment. Despite not being able to detect augmentation of plasmalogen in cortical brain tissue, PPI-1040 treated mice showed a significant improvement (p<0.05) in the hyperactivity phenotype typical of the model, and a strong correlation between behavior and plasma plasmalogen levels was observed Example 4: Long Term Potentiation (LTP) Studies in Mouse Hippocampal Brain Slices It is hypothesized that brain plasmalogen levels affect neurotransmission. Accordingly, in this study, wild-type mouse hippocampal brain slices were incubated in artificial cerebro-spinal fluid containing either vehicle or PPI-1040. The slices were incubated on a multi-electrode array (MEA) with electrodes spaced 100 μm apart. A single electrode was selected to stimulate Schaffer collaterals cells which triggered field excitatory post-synaptic potential (fEPSP) in the stratum radiatum. After 10 minutes of control recording, in the presences of either PPI-1040 or vehicle, long term potentiation (LTP) was induced by a single train of 10 bursts composed of 4 stimuli at 100 Hz each with a 200 millisecond interval between. The potentiation of the evoked-responses was then monitored for 60 mins Slices treated with PPI-1040 (0.5 µM) had increased LTP compared to vehicle treated controls over the 60 min period, suggesting that increasing plasmalogen levels increased neural plasticity, and supporting the importance of plasmalogens in neurological function. Results are shown in FIG. 14.

Long term potentiation is known to be compromised in the brains (particularly the hippocampus) of human and animals with Alzheimer's disease (AD) [49] and animal models of Parkinson's disease (PD) (Costa et al., 2012, Brain, 135:1884-1899). The ability of PPI-1040 to improve baseline LTP in the mouse brain, along with the reported plasmalogen deficiency in the AD [50-54] and PD brain [55-58] suggests a role for plasmalogen augmentation in the treatment of plasmalogen deficient neurodegenerative diseases.

Example 5: Comparison of PPI-1011 and PPI-1040

Both PPI-1011 and PPI-1040 are plasmalogen precursors designed to be converted to endogenous 16:0/22:6 ethanolamine plasmalogen species. Both molecules are composed of a glycerol backbone with a palmityl alcohol (16:0) at the sn-1 position and a DHA (22:6) fatty acid at the sn-2 position.

stabilize the molecule and prevent migration of the sn-1 and sn-2 moieties. It has been shown that the lipoic acid is cleaved in the gut with only the alkyl-acyl glycerol molecule crossing the gut lining. In vivo the alkyl-acyl glycerol must undergo the addition of a phosphoethanolamine group, which again occurs by enzymes in the endoplasmic reticulum. In contrast, PPI-1040 has a cyclized phosphoethanolamine group at the sn-3 position. This group has been cyclized in an effort to protect the vinyl-ether bond from cleavage to allow for longer term stability. Upon exposure of the PPI-1040 drug product to an aqueous or acidic environment (such as the stomach) the cyclic phosphoethanolamine group undergoes a hydrolysis reaction to open into the naturally occurring phosphoethanolamine group found on ethanolamine plasmalogens. These differences result in the plasmalogen precursors entering the metabolic pathway at very different points. PPI-1011 enters early in the pathway after the 2 peroxisomal specific enzymatic reactions. PPI-1040 enters at the end of the pathway, with the end plasmalogen product being the molecule that is absorbed through the gut lining, following spontaneous hydrolysis of the cyclic phosphoethanolamine group.

Once PPI-1011 or PPI-1040 is converted to the 16:0/22:6 ethanolamine plasmalogen species it enters the natural metabolic pathway of the body. Phospholipase 2 enzymes are known to remove the fatty acid at the sn-2 position which can be replaced with any other fatty acid molecule in the body, most commonly 18:1, 18:2, 20:4, 205:5, 22:4. Therefore in addition to augmenting the target plasmalogen (16:0/22:6) treatment with PPI-1011 and PPI-1040 are known to augment the family of ethanolamine plasmalogens with a palmityl group at sn-1.

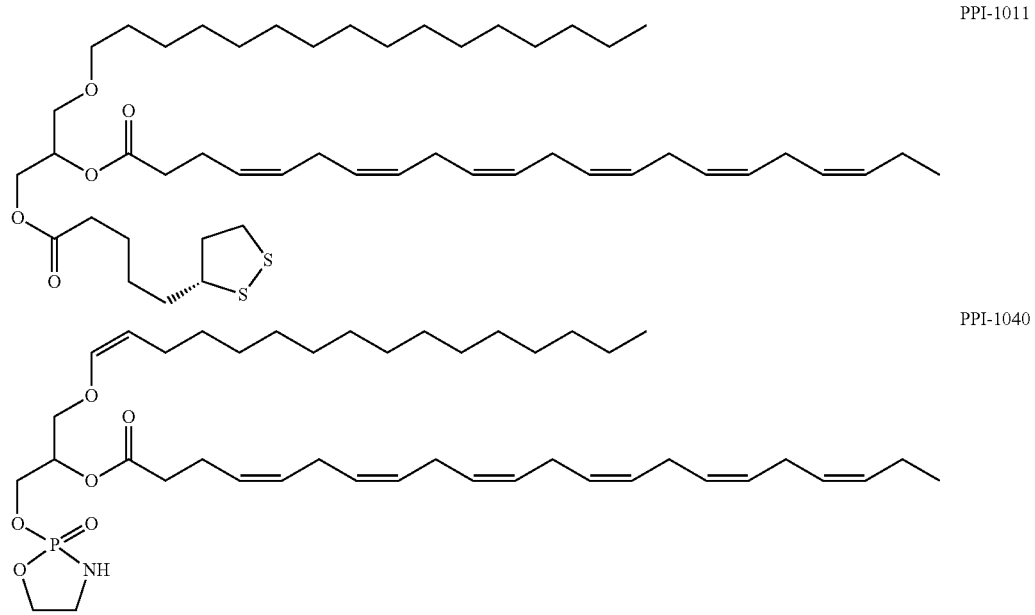

PPI-1011

PPI-1040

PPI-1011 has an ether bond at the sn-1 position connecting the glycerol backbone and the 16:0 fatty alcohol. In vivo this has to be enzymatically converted in the endoplasmic reticulum into the vinyl-ether bond characteristic of plasmalogens. PPI-1040 was designed with the vinyl-ether bond already intact at the sn-1 position, completely removing the requirement for in vivo metabolism. In addition, PPI-1011 has a lipoic acid at the sn-3 position. This is present to PPI-1040 PK Data To investigate the conversion of PPI-1040 in vivo and confirm that the generated PlsEtn can be detected in the serum, a $^{13}$C-labeled version of PPI-1040 was designed, designated PPI-1050. PPI-1050 is labeled with [$^{13}C_3$] palmityl acid and [$^{13}C_3$] glycerol.

Figure 15:
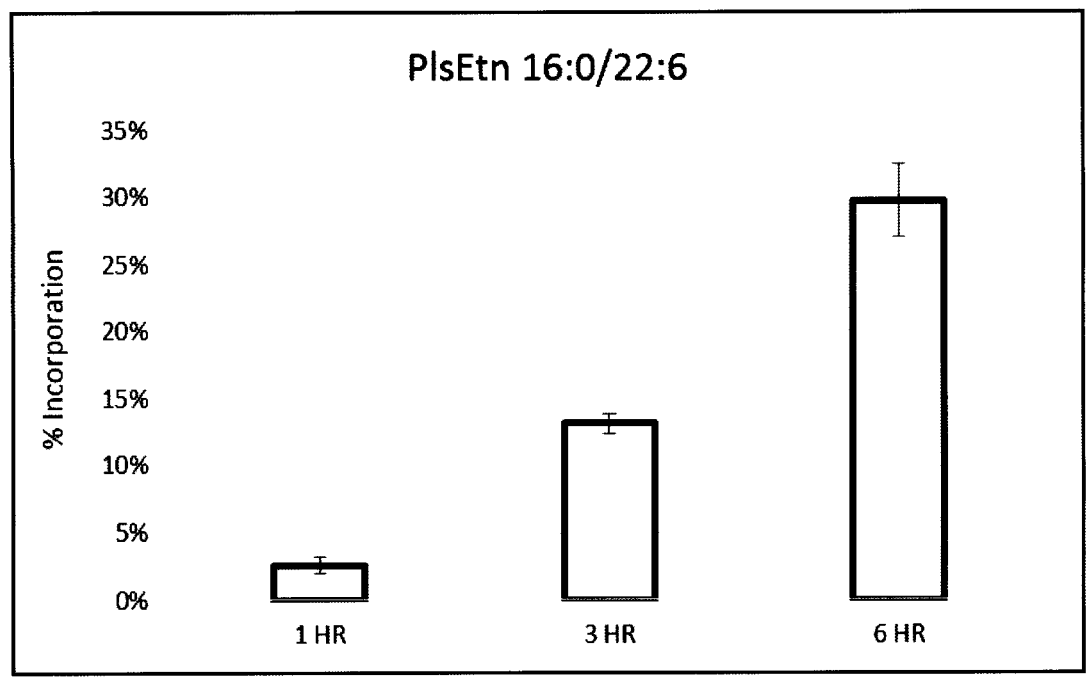
FIG. 15 shows time dependent increase in the % incorporation of the target 16:0/22:6 with [$^{13}C_3$]-palmitic at sn-1 and [$^{13}C_3$]-glycerol in plasma confirming the vinyl-ether bond remains intact following oral dosing of PPI-1050 (100 mg/kg), as highlighted from the data shown in FIG. 10.

C57Bl/6 mice were given a bolus dose of either vehicle (Neobee-M5 with 0.1% thioglycerol) or PPI-1050 orally at a concentration of 100 mg/kg. Animals were euthanized and serum was harvested after 1, 3 or 6 hours (n=3). Since there is a risk that providing an intact plasmalogen orally may result in cleavage of the vinyl-ether bond at the low pH present in the gut, resulting in the loss of the sn-1 fatty alcohol, studies were performed to confirm the feasibility of oral administration. The presence of $^{13}C$ label on the glycerol backbone and 16:0 fatty alcohol at sn-1 allowed for confirmation that the vinyl-ether bond remained intact through the gastrointestinal tract. Using flow injection tandem mass spectrometry, the target 16:0/22:6 plasmalogen labeled with $[^{13}C_3]$ palmitic acid and $[^{13}C_3]$ glycerol (parent/daughter transition—752.5/327.2) was detected in the serum of treated animals with levels increasing in a time-dependent manner (FIG. 15). The intact PPI-1050 molecule with the phosphoethanolamine ring closed (parent/daughter transition—736.5/613.5) was not detected in the serum of any of the animals treated, confirming that the ring readily opens following oral administration.

Figure 16:
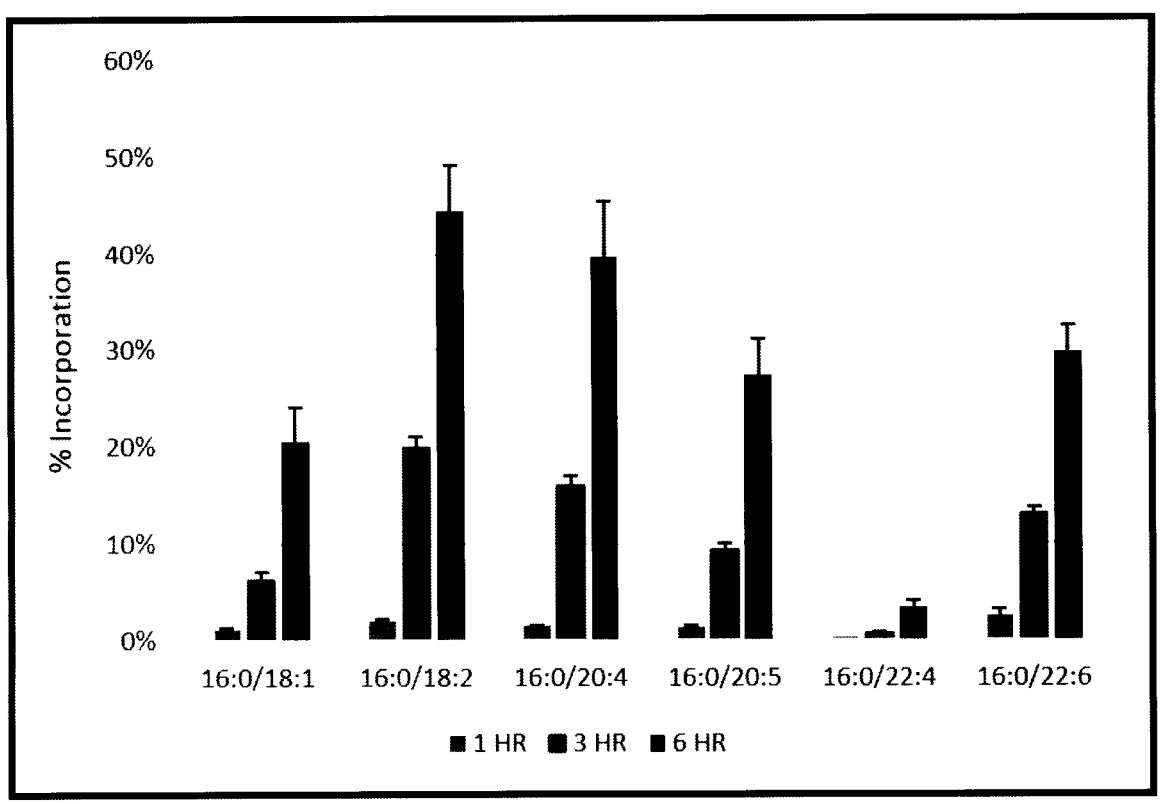
FIG. 16 shows time dependent increase in the % incorporation of 16:0 plasmalogen with the [$^{13}C_3$]-palmitic at sn-1 and [$^{13}C_3$]-glycerol in plasma confirming the vinyl-ether bond remains intact following oral dosing of PPI-1050 (100 mg/kg) while the sn-2 is readily remodeled, as highlighted from the data showing FIG. 10. Moving from left to right in each set of 3 bars, in the following order, shows 1 HR, 3 HR, and 6 HR.

Measuring the levels of plasmalogens with $[^{13}C_3]$ palmityl acid and $[^{13}C_3]$ glycerol with a variety of common fatty acids at sn-2 confirmed that while the vinyl-ether bond remained intact the sn-2 position was readily remodeled, with levels of all other 16:0 plasmalogens tested increasing in a time-dependent manner (FIG. 16).

Figure 17:
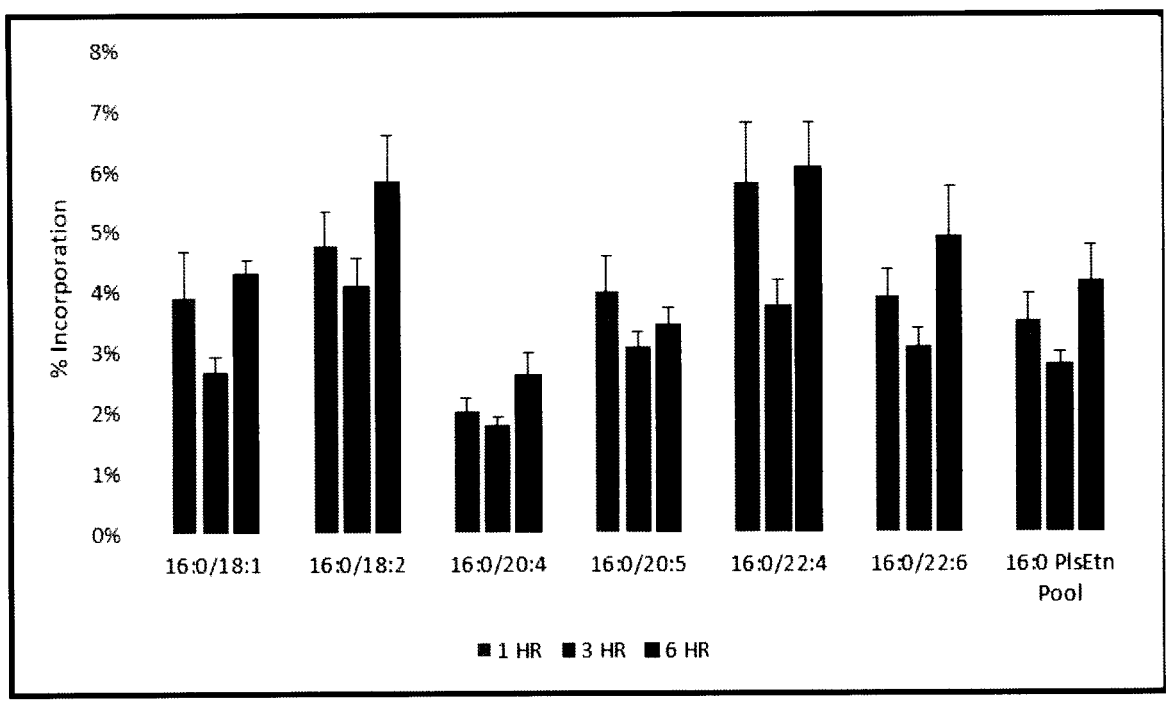
FIG. 17 shows incorporation of [$^{13}C_6$]-PPI-1050 into plasma 16:0 plasmalogen species with the [$^{13}C_3$]-palmitic sn-1 or [$^{13}C_3$]-glycerol, indicating that the vinyl ether-bond was not broken during re-substitution of the sn-2 position. PPI-1050 was dosed at 100 mg/kg by oral gavage. Moving from left to right in each set of 3 bars, in the following order, shows 1 HR, 3 HR, and 6 HR.

Measuring plasmalogen species with only the addition of $[^{13}C_3]$ allowed for further confirmation that the vinyl-ether bond remained intact. It was not possible to differentiate species with the glycerol-only labeled from those with the palmityl-only labeled, as both resulted in the same increase in mass. It was clear, however, that there was not an increase in 16:0 plasmalogen species with either the glycerol or palmitic labeled (FIG. 17). Without wishing to be bound by theory, the low levels observed are likely largely the result of interfering metabolites. In addition, no increases were observed in the unlabeled endogenous 16:0 plasmalogen levels following treatment (data not shown).

Figure 18:
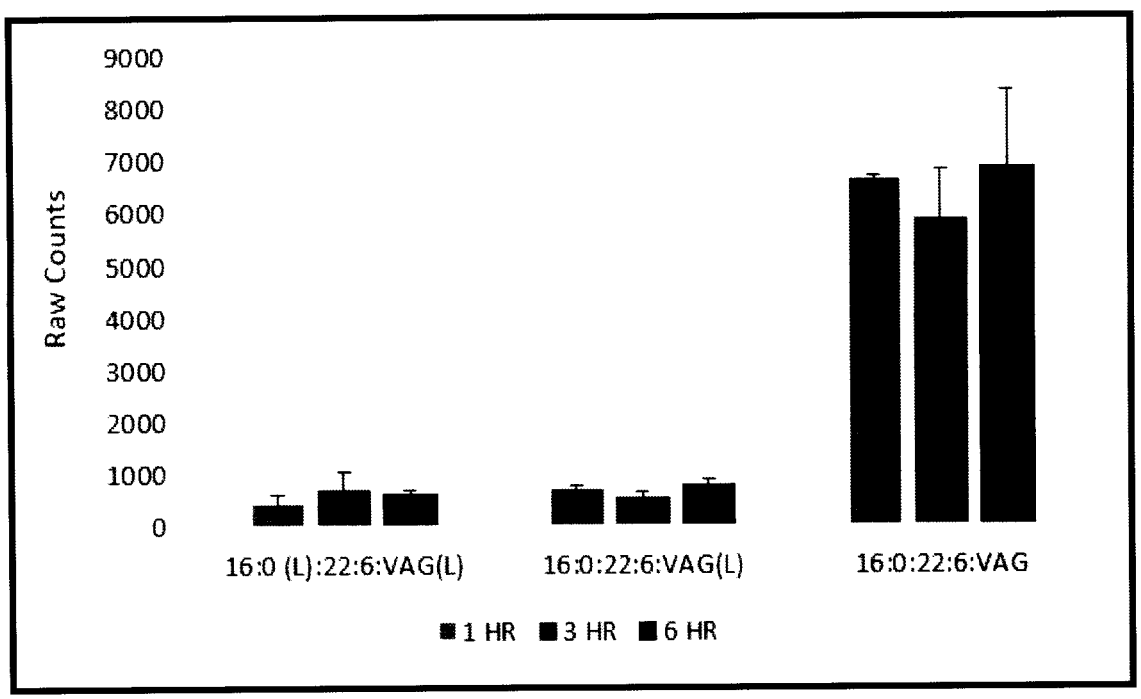
FIG. 18 shows levels of the [$^{13}C_6$] labeled (16:0(L): 22:6 VAG(L)) or the [$^{13}C_3$] labeled (16:0:22:6 VAG(L)) which did not show an increase following oral treatment with PPI-1050 at 100 mg/kg. Moving from left to right in each set of 3 bars, in the following order, shows 1 HR, 3 HR, and 6 HR.

To confirm that the phosphoethanolamine group was not lost from the sn-3 position following oral administration, levels of vinyl-acyl glycerols were also measured. Increases were not observed in the doubly labeled ($[^{13}C_3]$ palmitic acid and $[^{13}C_3]$ glycerol) or the singly labeled ($[^{13}C_3]$ palmitic acid or $[^{13}C_3]$ glycerol) 16:0/22:6 vinyl-acyl glycerols (FIG. 18). In addition, the $[^{13}C_3]$ palmitic acid and $[^{13}C_3]$ glycerol alkyl-acyl glycerol species were tested for, but were undetectable (data not shown).

Tracking the metabolic products of PPI-1050 confirmed the plasmalogen precursor was orally bioavailable in mice. The lack of detection of the closed ring form of PPI-1050 indicated that the ring was readily opened upon ingestion. The time-dependent increase in 16:0 plasmalogens with both the palmitic and glycerol labeled, but not the singly labeled versions, confirmed that the vinyl-ether bond remained intact. Failure to show an incorporation in either vinyl-acyl or alkyl-acyl glycerols supports a hypothesis that the ethanolamine group remained intact following oral administration. Together, this data provides support for oral administration of PPI-1040 as a therapeutic agent for plasmalogen deficiency.

PPI-1011 PK Data

To validate the conversion of PPI-1011 in vivo a $^{13}C$-labeled version of PPI-1011 was designed, designated as PPI-1038. PPI-1038 is labeled with $[^{13}C_3]$ palmityl acid and $[^{13}C_3]$ glycerol, the same as PPI-1050, but was additionally $[^{13}C_3]$ labeled on the sn-2 DHA. This addition allowed for tracing on the sn-2 group following administration which was not done in the PPI-1050 treated animals.

Figure 19:
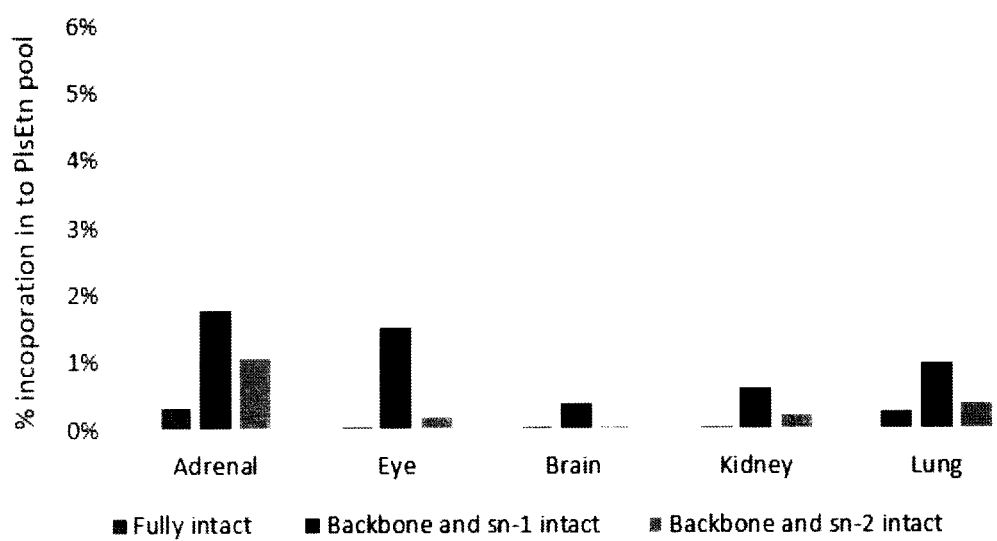
FIG. 19 shows percent incorporation into the target 16:0/22:6 plasmalogen with [$^{13}C_3$]-palmitic at sn-1, [$^{13}C_3$]-DHA at sn-2 and [$^{13}C_3$]glycerol, as well as other configurations of the labeled groups following oral dosing of PPI-1038 (100 mg/kg). Moving left to right in each set of 3 bars, in the following order, shows fully intact, backbone and sn-1 intact, and backbone and sn-2 intact.

C57Bl/6 mice were dosed with PPI-1038 formulated in Neobee-M5 orally at a concentration of 100 mg/kg once daily for 3 days. Animals were then euthanized and tissues were harvested (n=6). Using tandem mass spectrometry, the target 16:0/22:6 plasmalogen labeled with $[^{13}C_3]$ palmitic acid, $[^{13}C_3]$ glycerol and $[^{13}C_3]$ DHA (parent/daughter transition—768.5/330.2) was detected in various tissues of treated animals but levels were very low (fully intact group in FIG. 19). A higher degree of incorporation was seen for the 16:0/22:6 target plasmalogen when the sn-2 group was removed and the glycerol backbone and sn-1 group remained intact. There was also incorporation of the target plasmalogen into the tissue representing the glycerol backbone and the sn-2 containing label. Without wishing to be bound by theory, it is possible that this results from direct remodeling of the sn-1 position, although this may be contrary to other studies, which suggest sn-1 remodeling does not readily occur. It is more likely the results of recycling of the labeled DHA and glycerol group to synthesize de novo plasmalogens. PPI-1011 was not designed to be incorporated fully intact into tissue. The lipoic group at sn-3 was designed to be cleaved in the gut leading to absorption of an alkyl-acyl glycerol. This then requires endogenous enzymes to metabolize the precursor by adding a phosphoethanolamine group to the sn-3 position and creating the vinyl-ether bond at the sn-1.

Plasmalogen Augmentation in Deficient Animals

Figure 20:
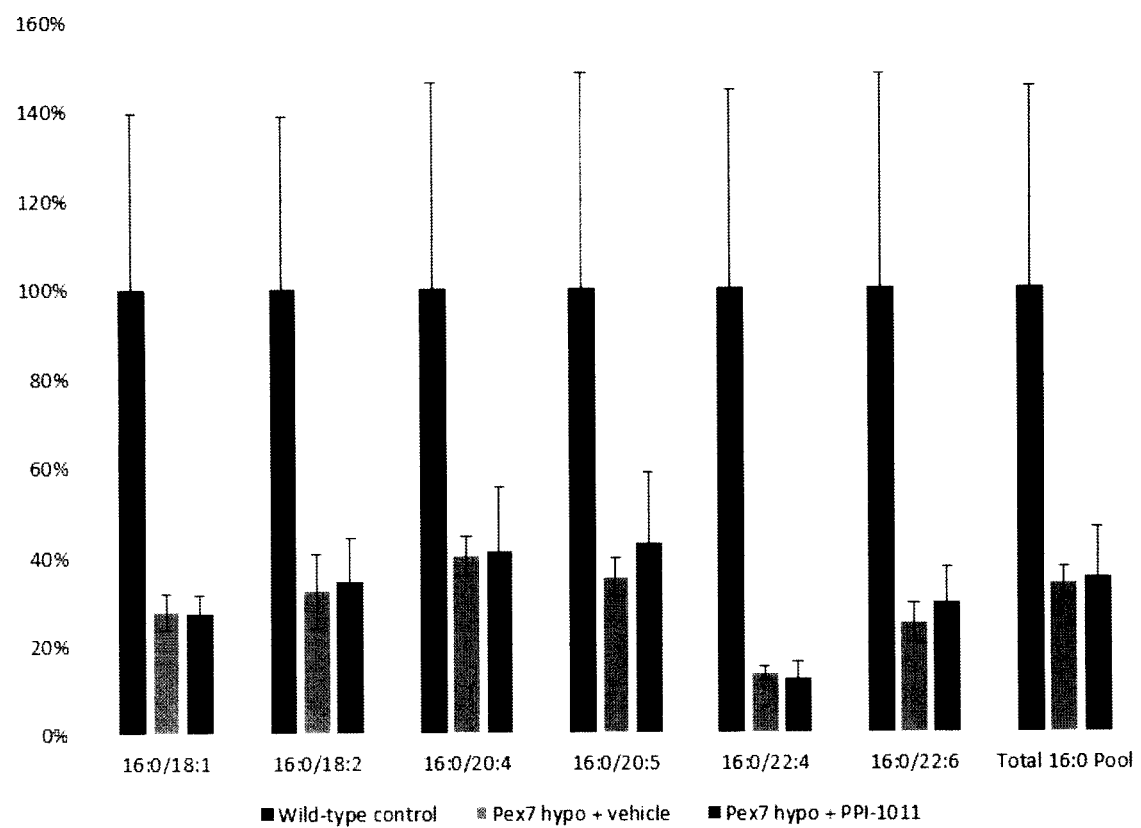
FIG. 20 shows liver plasmalogen levels comparing wild-type and Pex7 hypomorphic mice orally treated with vehicle or PPI-1011 for 4 weeks (5 doses per week). Moving left to right in each set of 3 bars, in the following order, shows wild-type control, Pex7 hypo+vehicle, and Pex7 hypo+PPI-1011.

In addition to the differences seen in the PK profiles of PPI-1040 and PPI-1011 as described above, the two molecules display different abilities to augment plasmalogen levels in a deficient animal model. Following 4 weeks of oral administration of vehicle, PPI-1011 or PPI-1040 to deficient mice, plasma and tissue levels were tested for plasmalogen levels. Pex7 hypomorphic/null animals treated with vehicle had significantly decreased levels of all plasmalogens measured, averaging approximately 25% of wild-type control levels. While in past studies PPI-1011 has demonstrated a modest ability to augment plasmalogen levels in animals, treatment with PPI-1011 at 50 mg/kg in the Pex7 hypomorph/null mice was ineffective at augmenting plasmalogen levels, with no change in the target plasmalogen or any other 16:0 plasmalogen species tested. PPI-1040 treatment however did effectively augment plasmalogen levels. In addition to normalizing the levels of the target 16:0/22:6 plasmalogen, re-organization at the sn-2 position occurred with increases in all 16:0 plasmalogens measured except 16:0/22:4, which represent a small proportion of the total 16:0 plasmalogen pool (FIG. 20). Plasmalogens containing 18:0 and 18:1 at sn-1 were also measured, but no augmentation was observed in those species as suspected. Finally, samples were analyzed for levels of vinyl-acyl and alkyl-acyl glycerols, which would be expected to increase if the phosphoethanolamine group at sn-3 was removed. None of the alkyl-acyl or vinyl-acyl glycerol species measured were increased in treated animals, matching the PPI-1040 PK data presented above.

Figure 12:
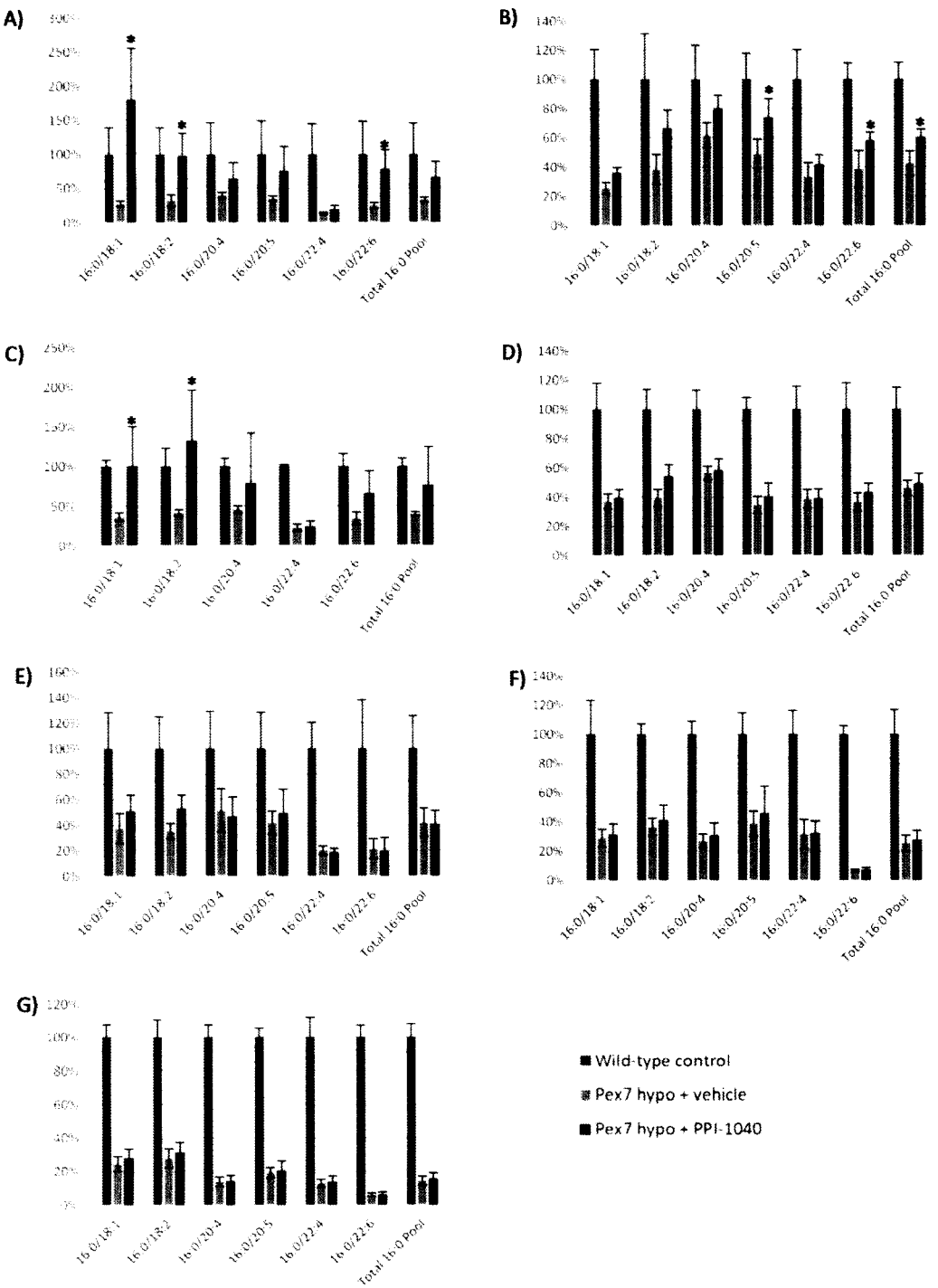
FIG. 12 shows plasmalogen levels in tissues from Pex7 hypomorphic/null mice treated with vehicle or PPI-1040. A) liver, B) skeletal muscle, C) small intestine, D) lung, E) kidney, F) cortex, G) cerebellum. All plasmalogen species were significantly below baseline in the vehicle and PPI-1011. Mean±SD, n=4-6 *-p<0.05 vs vehicle. Moving from left to right in each set of 3 bars shows, in the following order, Wild-type control, Pex7 hypo+vehicle, Pex7 hypo+PPI-1040. Wild-type and Pex7 hypomorphic mice orally treated with vehicle or PPI-1040 for 4 weeks (5 doses per week) are compared.

A variety of peripheral tissues, as well as brain tissues, were also analyzed for plasmalogen levels. As seen in the plasma, PPI-1011 did not increase the levels of any plasmalogen species in the liver (FIG. 20) or any of the tissues tested (data not shown). PPI-1040 was able to augment tissues to varying degrees in peripheral tissues with augmentation observed in the liver, skeletal muscle and small intestine. In the liver the levels of all plasmalogen species (except for 16:0/22:4) showed a trend towards increased levels with the 16:0/18:1. 16:0/18:2 and 16:0/22:6 species reaching statistical significance (FIG. 12A). Augmentation was also detectable in the skeletal muscle with the 16:0/20:5, 16:0/22:6 and total 16:0 plasmalogen pool levels statistically increased (FIG. 12B). Small intestine samples showed a high degree of inter-animal variation making interpretation more difficult. The levels of the 16:0/20:5 species were below the level of quantitation and therefore are not presented. The levels of a number of species appear to trend toward augmentation but only 16:0/18:1 and 16:0/18:2 reached significance (FIG. 12C) in this study. As reported for the plasma, plasmalogens with 18:0 and 18:1 at sn-1 were not augmented. In contrast, peripheral tissues lung and kidney did not display a significant level of augmentation in any plasmalogen species following treatment (FIG. 12 D, E). Finally, cortical and cerebellum tissue were tested and also did not show augmentation in PPI-1040 treated animals (FIG. 12 F, G).

Analysis of plasma and tissue plasmalogen levels following treatment clearly illustrated that PPI-1040 was a superior plasmalogen precursor for augmentation the plasmalogens in deficient individuals than an equal dose of PPI-1011.

Behavioural Assessments of Pex7 Hypomorph/Null Mice

Figure 21:
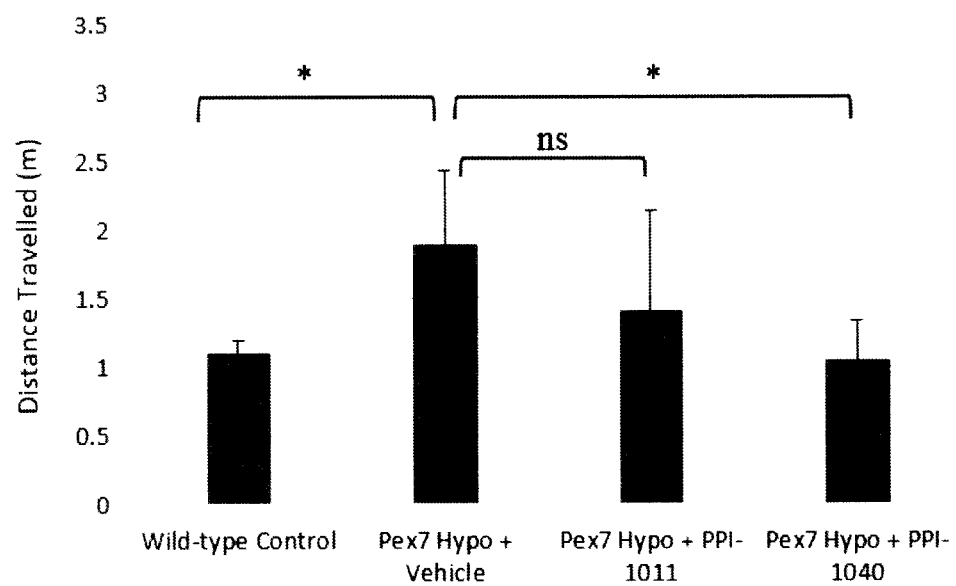
FIG. 21 shows activity level of Pex7 hypomorphic/null animals treated with vehicle, PPI-1011 or PPI-1040 relative to control in the open field test (PPI-1040 data is also shown in FIG. 13).
Figure 21:
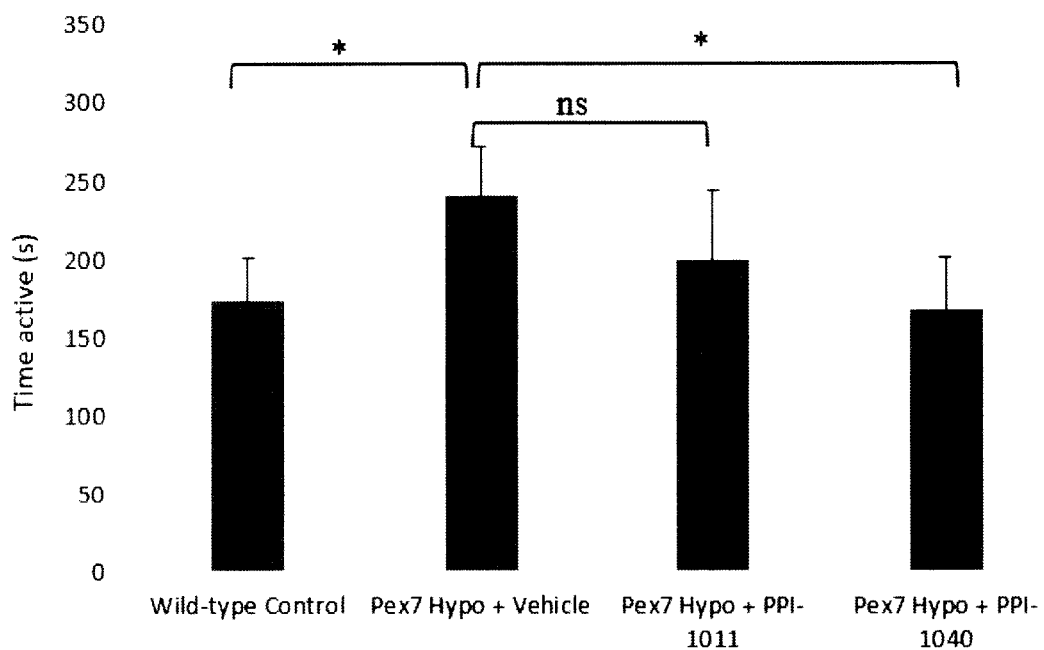

Pex7 hypomorph/null mice were tracked within an open field to assess the level of activity as measured by total distance traveled (meters) and time active (seconds). Vehicle treated animals displayed a significant level of hyperactivity relative to controls as assessed by either time or distance. Treatment with PPI-1011 did not result in a decrease in activity levels as assessed by either measurement. In contrast, treatment with PPI-1040 resulted in a significant decrease in activity and normalization of the hyperactive phenotype as assessed by both time active and distance travelled (FIG. 21).

Figure 13:
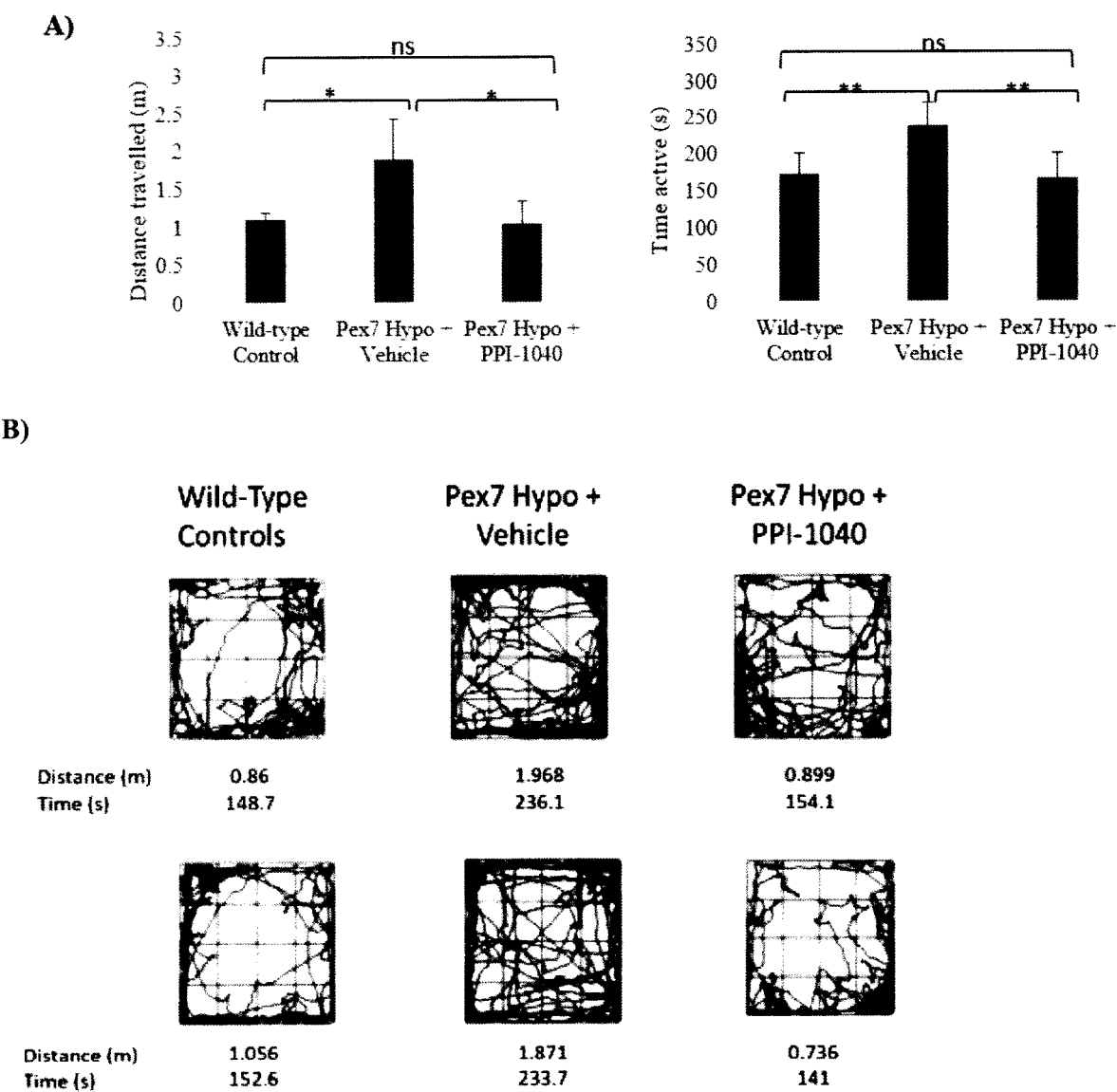
FIG. 13 shows results of the open field behavioral tests. A) Bar graphs of the distance measured and time mobile data from wild-type controls and Pex7 hypomorphic/null treated with vehicle or PPI-1040. B) Representative tracking data of animals' movement in the open field. C) Shows correlation of plasma plasmalogen levels to activity level of Pex7 hypomorphic/null animals treated with vehicle, PPI-1040 relative to control in an open field test. Correlation graphs of plasma PlsEtn 16:0/22:6 to distance travelled ($R^2$=0.36, F=7.93, p=0.014) and time active ($R^2$=0.54, F=16.37, p=0.0012) as well as total 16:0 PlsEtn levels to distance travelled ($R^2$=0.37, F=8.37, p=0.011) or time active ($R^2$=0.55, F=17.28, p=0.00096). n=4-6, *-p<0.05, ** p<0.01 are shown.
Figure 13:
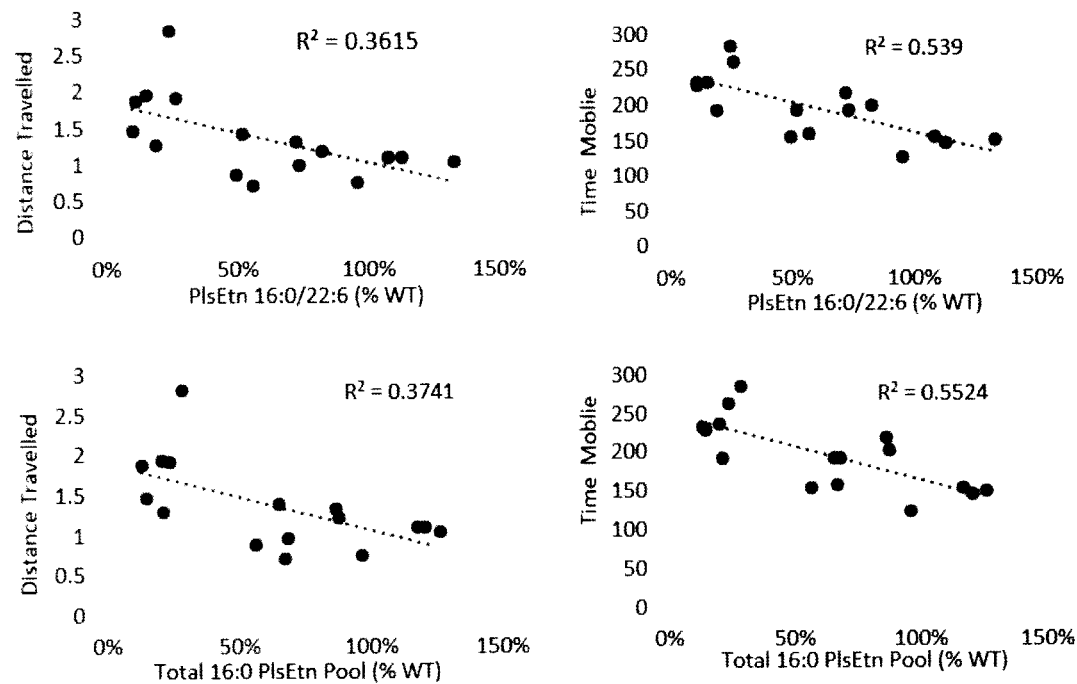

Comparing the control, vehicle and PPI-1040 animals, plasma plasmalogen levels correlated with the behavioral phenotype. Plasma levels of the target 16:0/22:6 plasmalogen correlated with both distance traveled ($R^2=0.36$, $F=7.93$, $p=0.014$) and time active ($R^2=0.54$, $F=16.37$, $p=0.0012$) (FIG. 13C). Total 16:0 pool in the plasma was used to evaluate the total effect of plasmalogen augmentation and was also shown to strongly correlate with both distance traveled ($R^2=0.37$, $F=8.37$, $p=0.011$) and time active ($R^2=0.55$, $F=17.28$, $p=0.00096$) (FIG. 21). The correlation of plasmalogen level with behavioral phenotype supports a hypothesis that plasmalogen augmentation may be a viable therapeutic target. The superior observed ability of PPI-1040 to augment plasmalogen levels may be particularly notable from a therapeutic perspective.

One or more illustrative embodiments have been described by way of example. It will be understood to persons skilled in the art that a number of variations and modifications may be made without departing from the scope of the invention as defined in the claims.

REFERENCES

1. Farooqui A A, Horrocks L A (2001) Plasmalogens: workhorse lipids of membranes in normal and injured neurons and glia. Neuroscientist 7: 232-245.
2. Braverman N E, Moser A B (2012) Functions of plasmalogen lipids in health and disease. Biochim Biophys Acta 1822: 1442-1452.
3. Braverman N, Chen L, Lin P, Obie C, Steel G, et al. (2002) Mutation analysis of PEX7 in 60 probands with rhizomelic chondrodysplasia punctata and functional correlations of genotype with phenotype. Hum Mutat 20: 284-297.
4. Itzkovitz B, Jiralerspong S, Nimmo G, Loscalzo M, Horovitz D D, et al. (2012) Functional characterization of novel mutations in GNPAT and AGPS, causing rhizomelic chondrodysplasia punctata (RCDP) types 2 and 3. Hum Mutat 33: 189-197.
5. Goodenowe D B, Cook L L, Liu J, Lu Y, Jayasinghe D A, et al. (2007) Peripheral ethanolamine plasmalogen deficiency: a logical causative factor in Alzheimer's disease and dementia. J Lipid Res 48: 2485-2498.
6. Han X, Holtzman D M, McKeel D W, Jr. (2001) Plasmalogen deficiency in early Alzheimer's disease subjects and in animal models: molecular characterization using electrospray ionization mass spectrometry. J Neurochem 77: 1168-1180.
7. Kou J, Kovacs G G, Hoftberger R, Kulik W, Brodde A, et al. (2011) Peroxisomal alterations in Alzheimer's disease. Acta Neuropathol 122: 271-283.
8. Fabelo N, Martin V, Santpere G, Marin R, Torrent L, et al. (2011) Severe alterations in lipid composition of frontal cortex lipid rafts from Parkinson's disease and incidental Parkinson's disease. Mol Med 17: 1107-1118.
9. Dragonas C, Bertsch T, Sieber C C, Brosche T (2009) Plasmalogens as a marker of elevated systemic oxidative stress in Parkinson's disease. Clin Chem Lab Med 47: 894-897.
10. Murphy E J, Schapiro M B, Rapoport S I, Shetty H U (2000) Phospholipid composition and levels are altered in Down syndrome brain. Brain Res 867: 9-18.
11. Moraitou M, Dimitriou E, Dekker N, Monopolis I, Aerts J, et al. (2014) Gaucher disease: plasmalogen levels in relation to primary lipid abnormalities and oxidative stress. Blood Cells Mol Dis 53: 30-33.
12. Braverman N, Steel G, Obie C, Moser A, Moser H, et al. (1997) Human PEX7 encodes the peroxisomal PTS2 receptor and is responsible for rhizomelic chondrodysplasia punctata. Nat Genet 15: 369-376.
13. Motley A M, Hettema E H, Hogenhout E M, Brites P, ten Asbroek A L, et al. (1997) Rhizomelic chondrodysplasia punctata is a peroxisomal protein targeting disease caused by a non-functional PTS2 receptor. Nat Genet 15: 377-380.
14. Purdue P E, Zhang J W, Skoneczny M, Lazarow P B (1997) Rhizomelic chondrodysplasia punctata is caused by deficiency of human PEX7, a homologue of the yeast PTS2 receptor. Nat Genet 15: 381-384.
15. Wanders R J, Schumacher H, Heikoop J, Schutgens R B, Tager J M (1992) Human dihydroxyacetonephosphate acyltransferase deficiency: a new peroxisomal disorder. J Inherit Metab Dis 15: 389-391.
16. Wanders R J, Dekker C, Hovarth V A, Schutgens R B, Tager J M, et al. (1994) Human alkyldihydroxyacetonephosphate synthase deficiency: a new peroxisomal disorder. J Inherit Metab Dis 17: 315-318.
17. White A L, Modaff P, Holland-Morris F, Pauli R M (2003) Natural history of rhizomelic chondrodysplasia punctata. Am J Med Genet A 118A: 332-342.
18. Braverman N, Zhang R, Chen L, Nimmo G, Scheper S, et al. (2010) A Pex7 hypomorphic mouse model for plasmalogen deficiency affecting the lens and skeleton. Mol Genet Metab 99: 408-416.
19. Brites P, Ferreira A S, da Silva T F, Sousa V F, Malheiro A R, et al. (2011) Alkyl-glycerol rescues plasmalogen levels and pathology of ether-phospholipid deficient mice. PLoS One 6: e28539.
20. Das A K, Holmes R D, Wilson G N, Hajra A K (1992) Dietary ether lipid incorporation into tissue plasmalogens of humans and rodents. Lipids 27: 401-405.

21. Holmes R D, Wilson G N, Hajra A K (1987) Oral ether lipid therapy in patientes with peroxisomal disorders. J Inherit Metab Dis 10: 239-241.
22. Braverman N E, Moser A E, Steinberg S J (2012) Rhizomelic chondrodysplasia punctata type 1. In: Pagon R A, Adam M P, Bird T D, R. D C, Fong C T, editors. GeneReviews. University of Washington, Seattle.
23. Stoll C, Dott B, Roth M P, Alembik Y (1989) Birth prevalence rates of skeletal dysplasias. Clin Genet 35: 88-92.
24. White A L, Modaff P, Holland-Morris F, Pauli R M (2003) Natural history of rhizomelic chondrodysplasia punctata. Am J Med Genet A 118A: 332-342.
25. Braverman N, Steel G, Obie C, Moser A, Moser H, et al. (1997) Human PEX7 encodes the peroxisomal PTS2 receptor and is responsible for rhizomelic chondrodysplasia punctata. Nat Genet 15: 369-376.
26. Motley A M, Hettema E H, Hogenhout E M, Brites P, ten Asbroek A L, et al. (1997) Rhizomelic chondrodysplasia punctata is a peroxisomal protein targeting disease caused by a non-functional PTS2 receptor. Nat Genet 15: 377-380.
27. Purdue P E, Zhang J W, Skoneczny M, Lazarow P B (1997) Rhizomelic chondrodysplasia punctata is caused by deficiency of human PEX7, a homologue of the yeast PTS2 receptor. Nat Genet 15: 381-384.
28. Wanders R J, Dekker C, Hovarth V A, Schutgens R B, Tager J M, et al. (1994) Human alkyldihydroxyacetone-phosphate synthase deficiency: a new peroxisomal disorder. J Inherit Metab Dis 17: 315-318.
29. Wanders R J, Schumacher H, Heikoop J, Schutgens R B, Tager J M (1992) Human dihydroxyacetonephosphate acyltransferase deficiency: a new peroxisomal disorder. J Inherit Metab Dis 15: 389-391.
30. Braverman N, Chen L, Lin P, Obie C, Steel G, et al. (2002) Mutation analysis of PEX7 in 60 probands with rhizomelic chondrodysplasia punctata and functional correlations of genotype with phenotype. Hum Mutat 20: 284-297.
31. Itzkovitz B, Jiralerspong S, Nimmo G, Loscalzo M, Horovitz D D, et al. (2012) Functional characterization of novel mutations in GNPAT and AGPS, causing rhizomelic chondrodysplasia punctata (RCDP) types 2 and 3. Hum Mutat 33: 189-197.
32. Braverman N E, Moser A B (2012) Functions of plasmalogen lipids in health and disease. Biochim Biophys Acta 1822: 1442-1452.
33. Goodenowe D B, Cook L L, Liu J, Lu Y, Jayasinghe D A, et al. (2007) Peripheral ethanolamine plasmalogen deficiency: a logical causative factor in Alzheimer's disease and dementia. J Lipid Res 48: 2485-2498.
34. Han X, Holtzman D M, McKeel D W, Jr. (2001) Plasmalogen deficiency in early Alzheimer's disease subjects and in animal models: molecular characterization using electrospray ionization mass spectrometry. J Neurochem 77: 1168-1180.
35. Kou J, Kovacs G G, Hoftberger R, Kulik W, Brodde A, et al. (2011) Peroxisomal alterations in Alzheimer's disease. Acta Neuropathol 122: 271-283.
36. Wood P L, Mankidy R, Ritchie S, Heath D, Wood J A, et al. (2010) Circulating plasmalogen levels and Alzheimer Disease Assessment Scale-Cognitive scores in Alzheimer patients. J Psychiatry Neurosci 35: 59-62.
37. Fabelo N, Martin V, Santpere G, Marin R, Torrent L, et al. (2011) Severe alterations in lipid composition of frontal cortex lipid rafts from Parkinson's disease and incidental Parkinson's disease. Mol Med 17: 1107-1118.
38. Dragonas C, Bertsch T, Sieber C C, Brosche T (2009) Plasmalogens as a marker of elevated systemic oxidative stress in Parkinson's disease. Clin Chem Lab Med 47: 894-897.
39. Kaddurah-Daouk R, McEvoy J, Baillie R, Zhu H, J K Y, et al. (2012) Impaired plasmalogens in patients with schizophrenia. Psychiatry Res 198: 347-352.
40. Murphy E J, Schapiro M B, Rapoport S I, Shetty H U (2000) Phospholipid composition and levels are altered in Down syndrome brain. Brain Res 867: 9-18.
41. Moraitou M, Dimitriou E, Dekker N, Monopolis I, Aerts J, et al. (2014) Gaucher disease: plasmalogen levels in relation to primary lipid abnormalities and oxidative stress. Blood Cells Mol Dis 53: 30-33.
42. Brites P, Motley A M, Gressens P, Mooyer P A, Ploegaert I, et al. (2003) Impaired neuronal migration and endochondral ossification in Pex7 knockout mice: a model for rhizomelic chondrodysplasia punctata. Hum Mol Genet 12: 2255-2267.
43. Braverman N, Zhang R, Chen L, Nimmo G, Scheper S, et al. (2010) A Pex7 hypomorphic mouse model for plasmalogen deficiency affecting the lens and skeleton. Mol Genet Metab 99: 408-416.
44. Brites P, Ferreira A S, da Silva T F, Sousa V F, Malheiro A R, et al. (2011) Alkyl-glycerol rescues plasmalogen levels and pathology of ether-phospholipid deficient mice. PLoS One 6: e28539.
45. Wood P L, Khan M A, Smith T, Ehrmantraut G, Jin W, et al. (2011) In vitro and in vivo plasmalogen replacement evaluations in rhizomelic chrondrodysplasia punctata and Pelizaeus-Merzbacher disease using PPI-1011, an ether lipid plasmalogen precursor. Lipids Health Dis 10: 182.
46. Wood P L, Smith T, Lane N, Khan M A, Ehrmantraut G, et al. (2011) Oral bioavailability of the ether lipid plasmalogen precursor, PPI-1011, in the rabbit: a new therapeutic strategy for Alzheimer's disease. Lipids Health Dis 10: 227.
47. Thai T P, Rodemer C, Jauch A, Hunziker A, Moser A, et al. (2001) Impaired membrane traffic in defective ether lipid biosynthesis. Hum Mol Genet 10: 127-136.
48. Brodde A, Teigler A, Brugger B, Lehmann W D, Wieland F, et al. (2012) Impaired neurotransmission in ether lipid-deficient nerve terminals. Hum Mol Genet 21: 2713-2724.
49. Koffie R M, Hyman B T, Spires-Jones T L (2011) Alzheimer's disease: synapses gone cold. Mol Neurodegener 6: 63.
50. Han X, Holtzman D M, McKeel D W, Jr. (2001) Plasmalogen deficiency in early Alzheimer's disease subjects and in animal models: molecular characterization using electrospray ionization mass spectrometry. J Neurochem 77: 1168-1180.
51. Goodenowe D B, Cook L L, Liu J, Lu Y, Jayasinghe D A, et al. (2007) Peripheral ethanolamine plasmalogen deficiency: a logical causative factor in Alzheimer's disease and dementia. J Lipid Res 48: 2485-2498.
52. Wood P L, Khan A M, Mankidy R, Smith T, Goodenowe D (2011) Plasmalogen Deficit: A New and Testable Hypothesis for the Etiology of Alzheimer's Disease. In: De La Monte S, editor Alzheimer's Disease Pathogenesis-Core Concepts, Shifting Paradigms and Therapeutic Targets: InTech.
53. Tajima Y, Ishikawa M, Maekawa K, Murayama M, Senoo Y, et al. (2013) Lipidomic analysis of brain tissues and plasma in a mouse model expressing mutated human amyloid precursor protein/tau for Alzheimer's disease. Lipids Health Dis 12: 68.
54. Wood P L, Barnette B L, Kaye J A, Quinn J F, Woltjer R L (2015) Non-targeted lipidomics of CSF and frontal cortex grey and white matter in control, mild cognitive impairment, and Alzheimer's disease subjects. Acta Neuropsychiatr 27: 270-278.
55. Dragonas C, Bertsch T, Sieber C C, Brosche T (2009) Plasmalogens as a marker of elevated systemic oxidative stress in Parkinson's disease. Clin Chem Lab Med 47: 894-897.

56. Fabelo N, Martin V, Santpere G, Marin R, Torrent L, et al. (2011) Severe alterations in lipid composition of frontal cortex lipid rafts from Parkinson's disease and incidental Parkinson's disease. Mol Med 17: 1107-1118.
57. Marin R, Fabelo N, Martin V, Garcia-Esparcia P, Ferrer I, et al. (2017) Anomalies occurring in lipid profiles and protein distribution in frontal cortex lipid rafts in dementia with Lewy bodies disclose neurochemical traits partially shared by Alzheimer's and Parkinson's diseases. Neurobiol Aging 49: 52-59.
58. Guedes L C, Chan R B, Gomes M A, Conceicao V A, Machado R B, et al. (2017) Serum lipid alterations in GBA-associated Parkinson's disease. Parkinsonism Relat Disord.59. Goodenowe D B, Cook L L, Liu J, Lu Y, Jayasinghe D A, et al. (2007) Peripheral ethanolamine plasmalogen deficiency: a logical causative factor in Alzheimer's disease and dementia. J Lipid Res 48: 2485-2498.
60. Han X, Holtzman D M, McKeel D W, Jr. (2001) Plasmalogen deficiency in early Alzheimer's disease subjects and in animal models: molecular characterization using electrospray ionization mass spectrometry. J Neurochem 77: 1168-1180.
61. Kou J, Kovacs G G, Hoftberger R, Kulik W, Brodde A, et al. (2011) Peroxisomal alterations in Alzheimer's disease. Acta Neuropathol 122: 271-283.
62. Wood P L, Mankidy R, Ritchie S, Heath D, Wood J A, et al. (2010) Circulating plasmalogen levels and Alzheimer Disease Assessment Scale-Cognitive scores in Alzheimer patients. J Psychiatry Neurosci 35: 59-62.
63. Fabelo N, Martin V, Santpere G, Marin R, Torrent L, et al. (2011) Severe alterations in lipid composition of frontal cortex lipid rafts from Parkinson's disease and incidental Parkinson's disease. Mol Med 17: 1107-1118.
64. Dragonas C, Bertsch T, Sieber C C, Brosche T (2009) Plasmalogens as a marker of elevated systemic oxidative stress in Parkinson's disease. Clin Chem Lab Med 47: 894-897.
65. Kaddurah-Daouk R, McEvoy J, Baillie R, Zhu H, J K Y, et al. (2012) Impaired plasmalogens in patients with schizophrenia. Psychiatry Res 198: 347-352.
66. Murphy E J, Schapiro M B, Rapoport S I, Shetty H U (2000) Phospholipid composition and levels are altered in Down syndrome brain. Brain Res 867: 9-18.
67. Moraitou M, Dimitriou E, Dekker N, Monopolis I, Aerts J, et al. (2014) Gaucher disease: plasmalogen levels in relation to primary lipid abnormalities and oxidative stress. Blood Cells Mol Dis 53: 30-33.
68. Baroy, T., et al. (2015). "A novel type of rhizomelic chondrodysplasia punctata, RCDP5, is caused by loss of the PEX5 long isoform." Hum Mol Genet 24(20): 5845-5854.
69. Braverman, N. E., et al. (2016). "Peroxisome biogenesis disorders in the Zellweger spectrum: An overview of current diagnosis, clinical manifestations, and treatment guidelines." Mol Genet Metab 117(3): 313-321.
70. Buchert, R., et al. (2014). "A peroxisomal disorder of severe intellectual disability, epilepsy, and cataracts due to fatty acyl-CoA reductase 1 deficiency." Am J Hum Genet 95(5): 602-610.

All references cited in this section and elsewhere in the specification are hereby incorporated by reference in their entirety.

What is claimed is:

1. A method of elevating at least one plasmalogen level in a subject in need thereof, said method comprising:
administering in vivo to said subject a therapeutically effective amount of at least one compound of formula A or formula A':

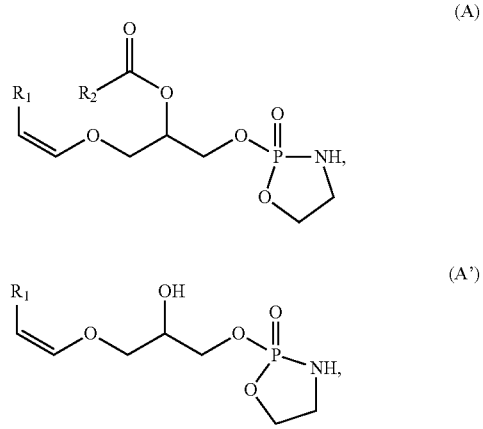

or a pharmaceutically acceptable salt or solvate thereof, wherein $R_1$ and $R_2$ are each, independently, a saturated, unsaturated, or polyunsaturated, optionally substituted hydrocarbon group,
wherein following administration, said compound of formula A of formula A' is converted to at least one plasmalogen species, thereby elevating the plasmalogen level in the subject.

2. The method according to claim 1, wherein $R_1$, $R_2$, or both, are optionally substituted $C_1$-$C_{28}$ hydrocarbon groups.

3. The method according to claim 1, wherein $R_1$, $R_2$, or both, each independently comprise up to 6 double bonds.

4. The method according to claim 1, wherein $R_1$, $R_2$, or both, are hydrocarbon chains of a fatty alcohol or fatty acid.

5. The method according to claim 1, wherein the subject suffers from a plasmalogen deficiency.

6. The method according to claim 1, wherein the subject suffers from a peroxisomal biogenesis disorder.

7. The method according to claim 1, wherein the subject has rhizomelic chondrodysplasia punctata (RCDP) or Zellweger spectrum disorder.

8. The method according to claim 1, wherein the at least one compound of formula A comprises one or more of:

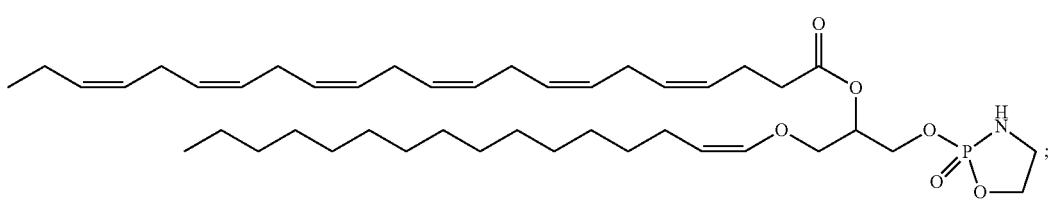

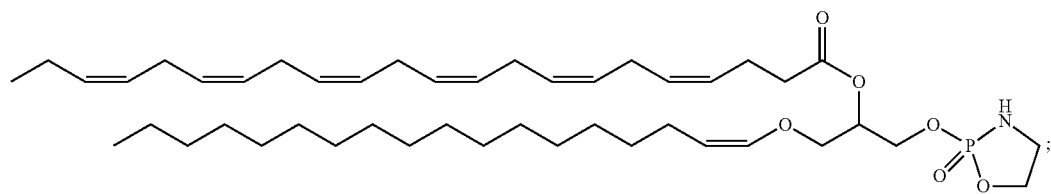
PPI-1054
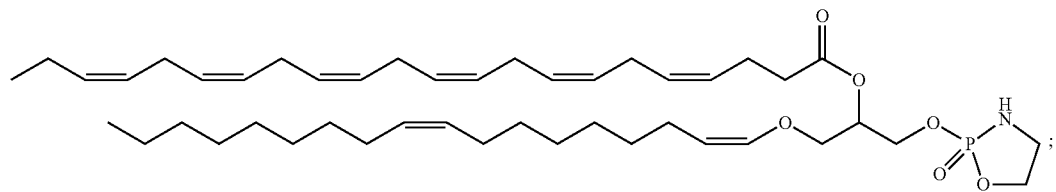
PPI-1056
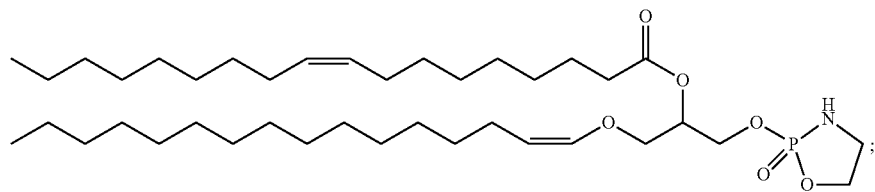
PPI-1063
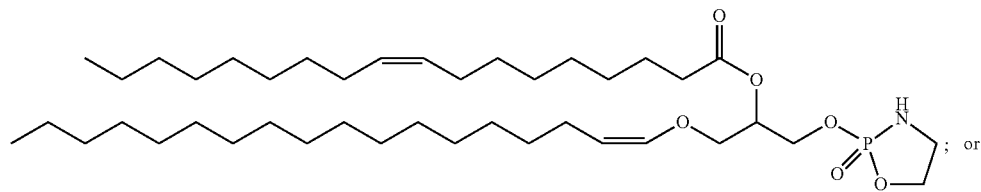
; or
PPI-1045
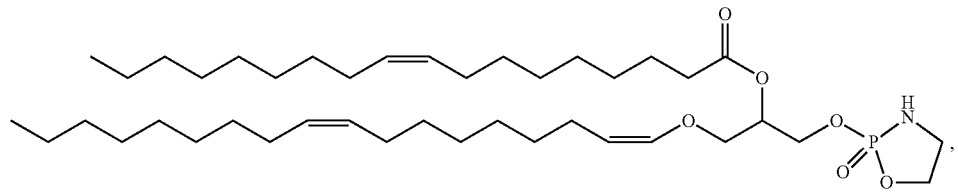
PPI-1046
or a pharmaceutically acceptable salt or solvate thereof.
9. The method of claim 1, wherein the subject has Alzheimer's disease or Parkinson's disease.
* * * * *